United States Patent
Gregory et al.

(10) Patent No.: US 9,458,205 B2
(45) Date of Patent: *Oct. 4, 2016

(54) MODIFIED DNA-BINDING PROTEINS AND USES THEREOF

(71) Applicant: Sangamo BioSciences, Inc., Richmond, CA (US)

(72) Inventors: Philip D. Gregory, Orinda, CA (US); Jeffrey C Miller, San Leandro, CA (US); David Paschon, Oakland, CA (US); Edward J. Rebar, San Francisco, CA (US); Siyuan Tan, Lexington, MA (US); Fyodor Urnov, Richmond, CA (US); Lei Zhang, Davis, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 243 days.

This patent is subject to a terminal disclaimer.

(21) Appl. No.: 13/679,684

(22) Filed: Nov. 16, 2012

(65) Prior Publication Data

US 2013/0196373 A1  Aug. 1, 2013

Related U.S. Application Data

(60) Provisional application No. 61/560,630, filed on Nov. 16, 2011, provisional application No. 61/694,710, filed on Aug. 29, 2012.

(51) Int. Cl.
| | |
|---|---|
| *C07K 14/195* | (2006.01) |
| *C12N 15/90* | (2006.01) |
| *C12N 5/071* | (2010.01) |
| *C12N 9/10* | (2006.01) |
| *C12N 15/63* | (2006.01) |
| *C12N 1/16* | (2006.01) |
| *C12N 9/22* | (2006.01) |
| *C12N 5/04* | (2006.01) |
| *C12P 19/34* | (2006.01) |

(52) U.S. Cl.
CPC ............. *C07K 14/195* (2013.01); *C12N 1/16* (2013.01); *C12N 5/04* (2013.01); *C12N 5/0602* (2013.01); *C12N 9/1007* (2013.01); *C12N 9/22* (2013.01); *C12N 15/902* (2013.01); *C12N 15/907* (2013.01); *C12P 19/34* (2013.01); *C12Y 301/21004* (2013.01); *C07K 2319/80* (2013.01); *C12N 15/63* (2013.01)

(58) Field of Classification Search
None
See application file for complete search history.

(56) References Cited

U.S. PATENT DOCUMENTS

| | | |
|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,689,558 B2 | 2/2004 | Case |
| 6,794,136 B1 | 9/2004 | Eisenberg et al. |
| 6,903,185 B2 | 6/2005 | Kim et al. |
| 7,070,934 B2 | 7/2006 | Cox, III et al. |
| 7,153,949 B2 | 12/2006 | Kim et al. |
| 7,163,824 B2 | 1/2007 | Cox, III et al. |
| 7,262,054 B2 | 8/2007 | Jamieson et al. |
| 8,420,782 B2 | 4/2013 | Bonas et al. |
| 8,440,431 B2 | 5/2013 | Voytas et al. |
| 8,440,432 B2 | 5/2013 | Voytas et al. |
| 8,450,107 B1 | 5/2013 | Zhang et al. |
| 8,450,471 B2 | 5/2013 | Voytas et al. |
| 8,697,853 B2 * | 4/2014 | Voytas et al. ............... 536/23.4 |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |

(Continued)

FOREIGN PATENT DOCUMENTS

| | | |
|---|---|---|
| EP | 2206723 A1 * | 7/2010 |
| GB | 2338237 | 12/1999 |

(Continued)

OTHER PUBLICATIONS

Morbitzer et al. Regulation of selected genome loci using de novo-engineered transcription activator-like effector (TALE)-type transcription factors. Proceedings of the National Academy of Sciences, USA, vol. 107, pp. 21617-21622, Nov. 24, 2010, including pp. 1/7-7/7 of Supporting Information.*

(Continued)

*Primary Examiner* — Jennifer Dunston

(74) *Attorney, Agent, or Firm* — Pasternak Patent Law; Susan Abrahamson

(57) ABSTRACT

Disclosed herein are enhanced polypeptides, polynucleotides encoding these polypeptides, cells and organisms comprising novel DNA-binding domains, including TALE DNA-binding domains. Also disclosed are methods of using these novel DNA-binding domains for modulation of gene expression and/or genomic editing of endogenous cellular sequences.

25 Claims, 17 Drawing Sheets

(56) References Cited

U.S. PATENT DOCUMENTS

| | | |
|---|---|---|
| 2005/0267061 A1 | 12/2005 | Martin |
| 2006/0063231 A1 | 3/2006 | Li et al. |
| 2006/0188987 A1 | 8/2006 | Guschin et al. |
| 2007/0134796 A1 | 6/2007 | Holmes et al. |
| 2007/0218528 A1 | 9/2007 | Miller |
| 2008/0015164 A1 | 1/2008 | Collingwood |
| 2008/0131962 A1 | 6/2008 | Miller |
| 2008/0159996 A1 | 7/2008 | Ando et al. |
| 2008/0182332 A1 | 7/2008 | Cai |
| 2009/0054985 A1 | 2/2009 | Anderson |
| 2009/0205083 A1 | 8/2009 | Gupta et al. |
| 2009/0305346 A1 | 12/2009 | Miller |
| 2009/0311787 A1 | 12/2009 | Miller |
| 2010/0047805 A1 | 2/2010 | Wang |
| 2011/0014616 A1 | 1/2011 | Holmes et al. |
| 2011/0145940 A1 | 6/2011 | Voytas et al. |
| 2011/0201055 A1 | 8/2011 | Doyon et al. |
| 2011/0239314 A1 | 9/2011 | Ahn et al. |
| 2011/0301073 A1 | 12/2011 | Gregory et al. |
| 2012/0064620 A1 | 3/2012 | Boch et al. |
| 2012/0110685 A1 | 5/2012 | Bonas et al. |
| 2012/0122205 A1 | 5/2012 | Boch et al. |
| 2012/0178131 A1 | 7/2012 | Bogdanove et al. |
| 2012/0214228 A1 | 8/2012 | Bogdanove et al. |
| 2013/0097734 A1 | 4/2013 | Kamoun et al. |
| 2013/0117869 A1 | 5/2013 | Duchateau et al. |
| 2013/0122581 A1 | 5/2013 | Voytas et al. |

FOREIGN PATENT DOCUMENTS

| | | |
|---|---|---|
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 2007/014275 A2 | 2/2007 |
| WO | WO 2007/139982 A2 | 12/2007 |
| WO | WO 03/016496 A2 | 2/2008 |
| WO | WO 2009/042163 A2 | 4/2009 |
| WO | WO 2010/079430 A1 | 7/2010 |
| WO | WO 2010117464 A1 * | 10/2010 |
| WO | 2011072246 A2 | 6/2011 |
| WO | 2011146121 A1 | 11/2011 |

OTHER PUBLICATIONS

Athinuwat et al. Xanthomonas axonopodis pv. glycines soybean cultivar virulence specificity is determined by avrBs3 homolog avrXgl. Phytopathology, vol. 99, No. 8, pp. 996-1004, Aug. 2009.*
Beerli, et al., "Engineering Polydactyl Zinc-Finger Transcription Factors," *Nat. Biotechnol.* 20:135-141 (2002).
Bitinaite, et al., "FokI Dimerization Is Required for DNA Cleavage," *Proc. Natl. Acad. Sci.* 95(18): 326(5959):1509-1512 (2009).
Boch, et al., "Breaking the Code of DNA Binding Specificity of Tal-Type III Effectors," *Science* 326(5959):1509-1512 (2009).
Boch, et al., "Xanthomonas AVRBS3 Family-Type III Effectors: Discovery and Function," *Annual Review of Phytopatholo* 48:419-436 (2010).
Bonas, et al., "Genetic and Structural Characterization of the Avirulence Gene AVRBS3 From Xanthomonas Campestris Pv. Vesicatoria," *Mol. Gen. Genet.* 218(1):127-136 (1989).
Cermak, et al., "Efficient Design and Assembly of Custom Talen and Other Tal Effector-Based Constructs for DNA Targeting," *Nucleic Acid Res.* 39:E82 (2011).
Choo, et al., "Advances in Zinc Finger Engineering," *Curr. Opin. Struct. Biol.* 10:411-416 (2000).
Christian, et al., "Targeting DNA Double-Strand Breaks With Tal Effector Nucleases," *Genetics* 186(2):757-761 (2010).
Doyon, et al., Enhancing zinc-finger-nuclease activity with improved obligate heterodimeric architecthures. Nature Methods 8(1):74-79, 2011.
Guo, et al., "Directed Evolution of an Enhanced and Highly Efficient Foki Cleavage Domain for Zinc Finger Nucleases," *J. Mol. Biol.* 400:96-107 (2010).
Gurelebeck, et al. "Dimerization of the Bacterial Effector Protein AVRBS3 in the Plant Cell Cytoplasm Prior to Nuclear Import," *Plant J.* 42(2):175-187 (2009).
Guschin, et al., "A Rapid and General Assay for Monitoring Endogenous Gene Modification," *Meth. Mol. Biol.* 649:247-256 (2010).
Heuer, et al., "Repeat Domain Diversity of AVRBS3-Like Genes in Ralstonia Solanacearum Strains and Association With Host Preferences in the Field," *Appl. Environ. Microbiol.* 73(13):4379-4384 (2007).
Hockemeyer, et al., "Genetic Engineering of Human Pluripotent Cells Using Tale Nucleases," *Nat. Biotech.* 29:731-734 (2011).
Holt, et al., "Human Hematopoietic Stem/Progenitor Cells Modified by Zinc-Finger Nucleases Targeted to CCR5 Control HIV-1 in Vivo," *Nat. Biotech.* 28:839-847 (2010).
Huang, et al., "Heritable Gene Targeting in Zebrafish Using Customized Talens," *Nature Biotech.* 29:699-700 (2011).
Isalan, et al., "A Rapid, Generally Applicable Method to Engineer Zinc Fingers Illustrated by Targeting the HIV-1 Promoter," *Nat. Biotechnol.* 19(7):656-660 (2001).
Kay, et al., "A Bacterial Effector Acts As a Plant Transcription Factor and Induces a Cell Size Regulator," *Science* 318(5850):648-651(2007).
Kim, et al., "Chimeric Restriction Endonuclease," *Proc. Natl. Acad. Sci.* 91:883-887 (1994).
Kim, et al. "Targeted Genome Editing in Human Cells With Zinc Finger Nucleases Constructed Via Modular Assembly," *Genome Res.* 19:1279-1288 (2009).
Kim, et al., "Insertion and Deletion Mutants of Foki Restriction Endonuclease," *J. Biol. Chem.*, 269(50):31,978-31,982 (1994).
Kim, et al., "Hybrid Restriction Enzymes: Zinc Finger Fusions to Fok I Cleavage Domain," *Proc. Natl. Acad. Sci.* 93(31:1156-1160 (1996).
Li, et al., "Functional Domains in Fok I Restriction Endonuclease," *Proc. Natl. Acad. Sci.* 89:42754279 (1992).
Li, et al., "Alteration of Tile Cleavage Distance of Fok I Restriction Endonuclease by Insertion Mutagenesis," *Proc. Natl. Acad. Sci.* 90:2764-2768 (1993).
Li, et al , "Tal Nucelases (TALNS): Hybrid Proteins Composed of Tal Effectors and Fok1 DNA-Cleavage Domain," *Nucleic Acids Research* 39(1):359-372 Epub Aug. 10, 2010 (2010).
Li, et al , "Modularly Assembled Designer Tal Effector Nucleases for Targeted Gene Knockout and Gene Replacement in Eukaryotes," *Nucleic Acids Research* epub doi:0.1093/nar/gkrl88 (2011).
Mapp, et al., "Activation of Gene Expression by Small Molecule Transcription Factors," *PNAS USA* 97:3930-3935 (2000).
Miller, et al., "A Tale Nuclease Architecture for Efficient Genome Editing," *Nature Biotechnology* 29(2):143-150 (2011).
Moscou, et al., "A Simple Cipher Governs DNA Recognition by Tal Effectors," *Science* 326(5959):1501 (2009).
Perez, et al., "Establishment of HIV-1 Resistance in CD4+ T Cells by Genome Editing Using Zinc-Finger Nucleases," *Nat. Biotech.* 26:808-816 (2008).
Pabo, et al., "Design and Selection of Novel CYS2HIS2 Zinc Finger Proteins," *Ann. Rev. Biochem.* 70:313-340 (2001).
Rebar, "Development of Pro-Angiogenic Engineered Transcription Factors for the Treatment of Cardiovascular Disease," *Expert Opin. Investig. Drugs* 13:829-839 (2004).
Roberts, et al., "Rebase: Restriction Enzymes and Methyltransferases," *Nucl. Acids. Res.* 31:418-420 (2003).

(56) References Cited

OTHER PUBLICATIONS

Romer, et al., "Recognition of AVRBS3-Like Proteins Is Mediated by Specific Binding to Promoters of Matching Pepper BS3 Alleles," *Plant Physiol.* 150(4):1697-1712 (2009).

Santiago, et al., "Targeted Gene Knockout in Mammalian Cells by Using Engineered Zinc Finger Nucleases," *PNAS USA* 105:5809-5814 (2008).

Scholze, et al., "Tal Effector-DNA Specificity," *Virulence* 105:428-432 (2010).

Schomack, et al., "Gene-For-Gene-Mediated Recognition of Nuclear-Targeted AVRBS3-Like Bacterial Effector Proteins," *J. Plant Physiol.* 163(3):256-272 (2006).

Segal, et al., "Custom DNA-Binding Proteins Come of Age: Polydactyl Zinc-Finger Proteins," *Curr. Opin. Biotechnol.* 12:632-637 (2001).

Stephens, et al., "Dating the Origin of the CCR5-D32 AIDS-Resistance Allele by the Coalescence of Haplotypes," *Am. J. Human Genet.* 62:1507-1515 (1998).

Yang, et al., "Three-Amino Acid Extension Loop Homeodomain Proteins MEIS2 and TGIF Differentially Regulate Transcription," *J. Biol. Chem.* 275:20734-20741 (2000).

Yang, et al., "The Virulence Factor AVRXA7 of Xanthomonas Oryzae Pv. Oryzae Is a Type III Secretion Pathway-Dependent Nuclear-Localized Double-Stranded DNA-Binding Protein," *PNAS* 97(17):9807-9812 (2009).

Zaremba, et al., "Generation of the BFII Restriction Endonuclease From the Fusion of a DNA Recognition Domain to a Non-Specific Nuclease From the Phospholipase D Superfamily," *J. Mol. Biol.* 336:81-92 (2004).

Zhu, et al., "AVRXA10 Contains an Acidic Transcriptional Activation Domain in the Functionally Conserved C Terminus," *MPMI* 11(8): 824-832 (1998).

Zhang, et al., "Efficient Construction of Sequence-Specific Tal Effectors for Modulating Mammalian Transcription," Nature Biotechnology 29(2):149-153 (2011).

\* cited by examiner

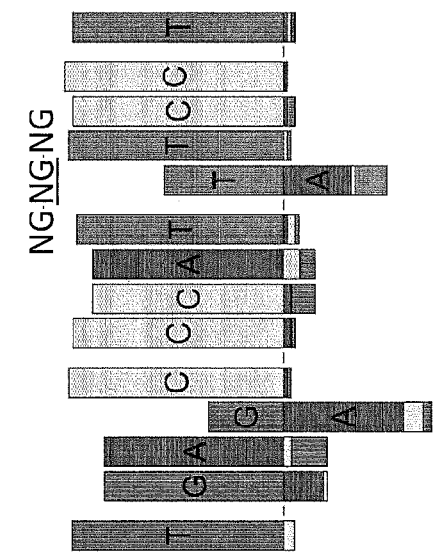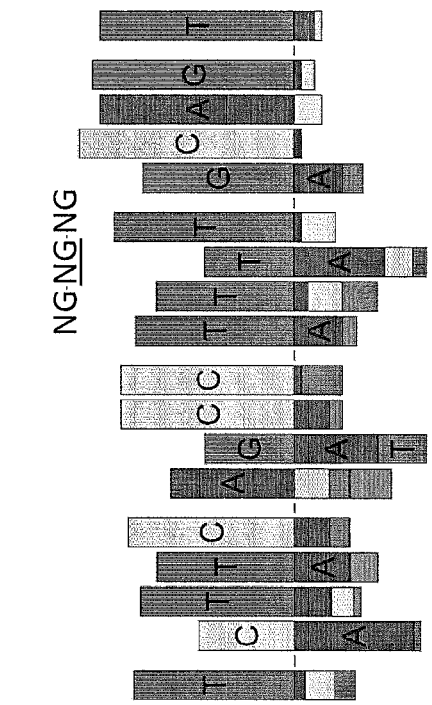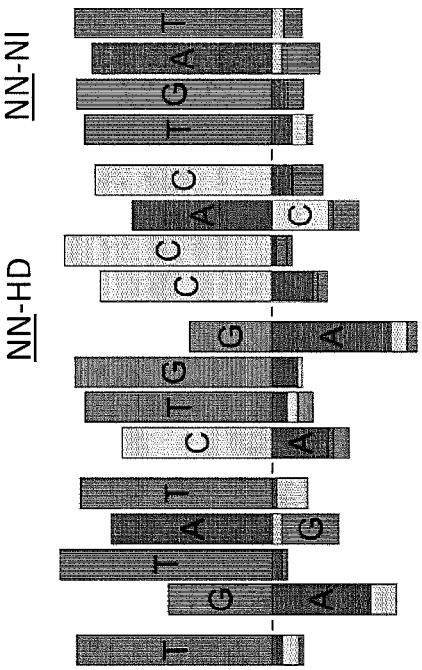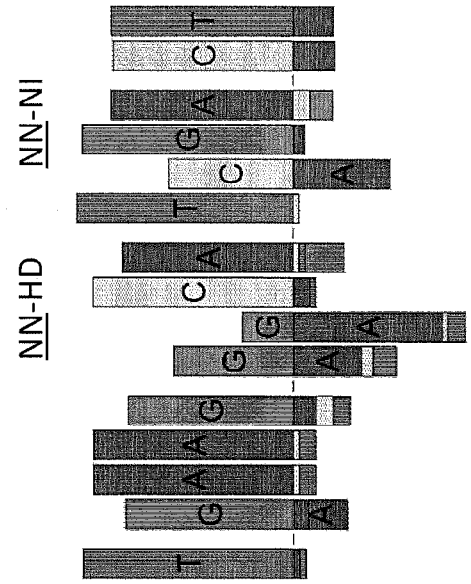
Figure 3

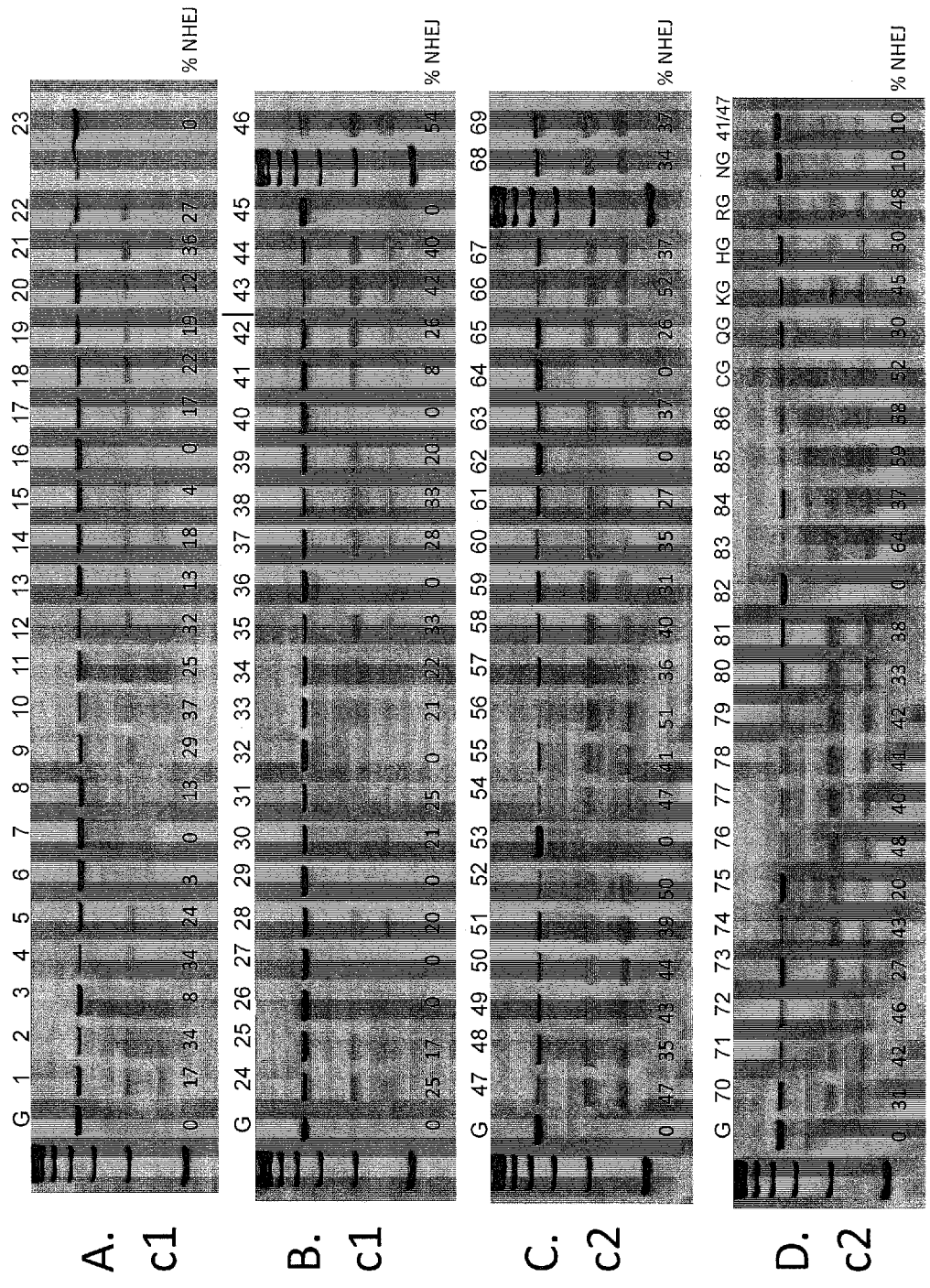
Figure 6, conditions 1 and 2

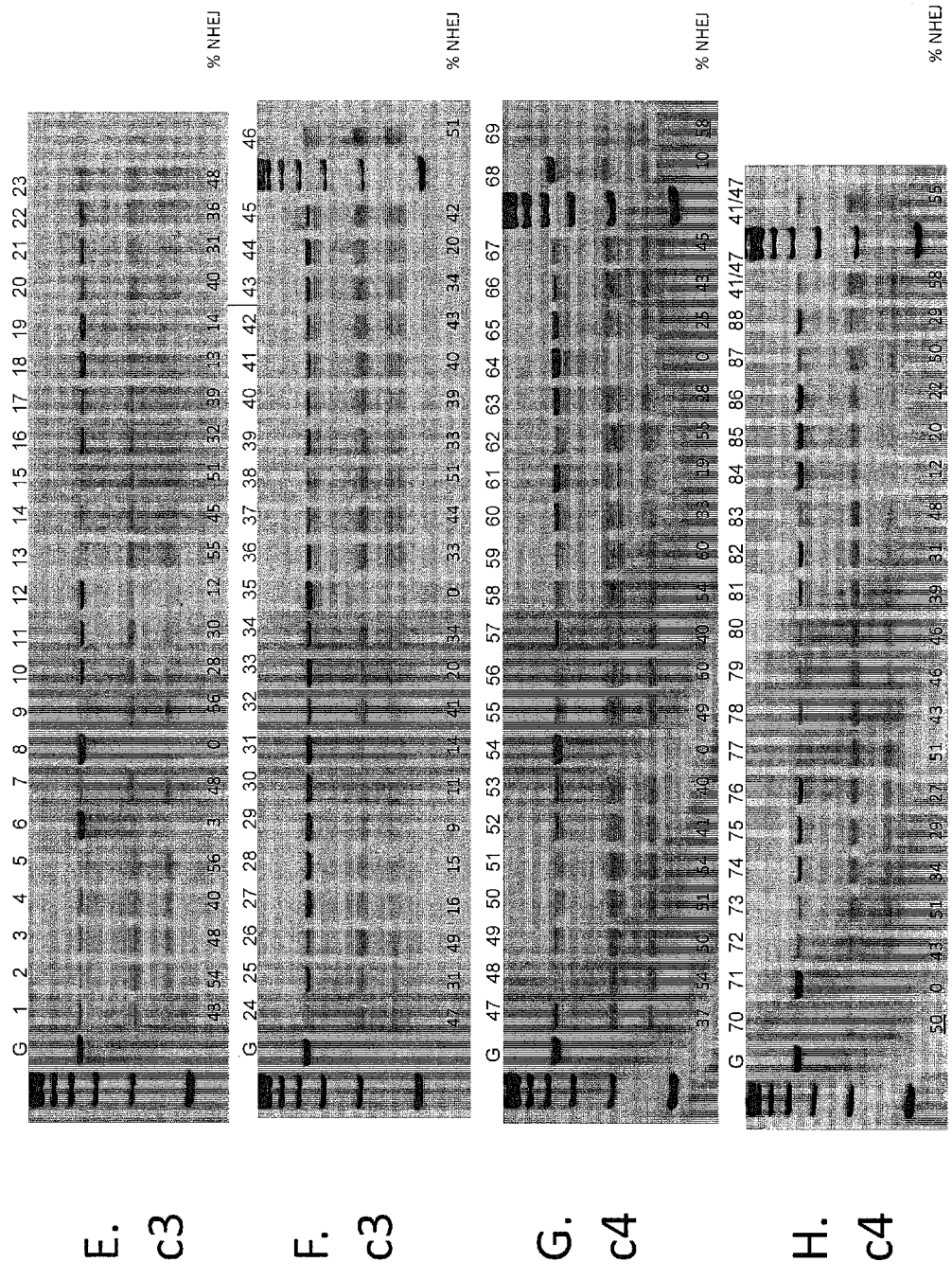
Figure 6, conditions 3 and 4

Figure 10b

| # | TALE101043-BfiI | TALE101047-BfiI |
|---|---|---|
| 133 | AAAGAAGGTCTTCATTACACCTGCAGCTCTCAGCTCTCATTTTCCATACAGTCAGTATCAGTATCAATTCAATTCTGGAAGAATTTCCAGACATTAAA |
| 58 | AAAGAAGGTCTTCATTACACCTGCAGCTCTCAGCTCTCATTTTCCATTTTCCATA::::CAGTATCAATTCAATTCTGGAAGAATTCCAGACATTAAA |
| 46 | AAAGAAGGTCTTCATTACACCTGCAGCTCTCAGCTCTCATTTTCCATTTTCCATA::::AGTATCAATTCAATTCTGGAAGAATTCCAGACATTAAA |
| 43 | AAAGAAGGTCTTCATTACACCTGCAGCTCTCAGCTCTCATTTTCCATTTTCCAT::::AGTATCAATTCAATTCTGGAAGAATTCCAGACATTAAA |
| 29 | AAAGAAGGTCTTCATTACACCTGCAGCTCTCAGCTCTCATTTTCCATTTTCCATTTCC::::ATCAATTCAATTCTGGAAGAATTCCAGACATTAAA |
| 31 | AAAGAAGGTCTTCATTACACCTGCAGCTCTCAGCTCTCATTTTCCATTTTCCATAC::TCAGTATCAATTCAATTCTGGAAGAATTCCAGACATTAAA |
| 26 | AAAGAAGGTCTTCATTACACCTGCAGCTCTCAGCTCTCATTTTCCATTTTCCATACA::AGTATCAATTCAATTCTGGAAGAATTCCAGACATTAAA |
| 27 | AAAGAAGGTCTTCATTACACCTGCAGCTCTCAGCTCTCATTTTCCATTTTCCA::::TCAGTATCAATTCAATTCTGGAAGAATTCCAGACATTAAA |
| 27 | AAAGAAGGTCTTCATTACACCTGCAGCTCTCAGCTCTCATTTTCCATTTTCCATA::::AGTATCAATTCAATTCTGGAAGAATTCCAGACATTAAA |
| 17 | AAAGAAGGTCTTCATTACACCTGCAGCTCTCAGCTCTCATT::CCATACAGTCAGTATCAATTCAATTCTGGAAGAATTCCAGACATTAAA |
| 17 | AAAGAAGGTCTTCATTACACCTGCAGCTCTCAGCTCTCA::::TCAATTCAATTCTGGAAGAATTCCAGACATTAAA |
| 18 | AAAGAAGGTCTTCATTACACCTGCAGCTCTCAGCTCTCATTTTCCATA::::TCAGTATCAATTCAATTCTGGAAGAATTCCAGACATTAAA |
| 19 | AAAGAAGGTCTTCATTACACCTGCAGCTCTCAGCTCTCATTTTCCATACAG::GTATCAATTCAATTCTGGAAGAATTCCAGACATTAAA |
| 18 | AAAGAAGGTCTTCATTACACCTGCAGCTCTCAGCTCTCATTTTCCAT::::::ATCAATTCAATTCTGGAAGAATTCCAGACATTAAA |
| 13 | AAAGAAGGTCTTCATTACACCTGCAGCTCTCAGCTCTCATTTTCCATTTTCCATACAG::::TCAATTCAATTCTGGAAGAATTCCAGACATTAAA |
| 11 | AAAGAAGGTCTTCATTACACCTGCAGCTCTCAGCTCTCATTTTCCATTTTCCAT::::::::AATTTCCAGACATTAAA |
| 12 | AAAGAAGGTCTTCATTACACCTGCAGCTCTCAGCTCTCATTTTCCATTTTCCAT::AGTCAGTATCAATTCAATTCTGGAAGAATTCCAGACATTAAA |
| 12 | AAAGAAGGTCTTCATTACACCTGCAGCTCTCAGCTCTCATTTTCCATTTTCCAT::GTCAGTATCAATTCAATTCTGGAAGAATTCCAGACATTAAA |
| 22 | AAAGAAGGTCTTCATTACACCTGCAGCTCTCAGCTCTCATTTTCCATTTTCCATAaa::::CAGTATCAATTCAATTCTGGAAGAATTCCAGACATTAAA |
| 15 | AAAGAAGGTCTTCATTACACCTGCAGCTCTCAGCTCTCATTTTCCATTTTCCATA::::TATCAATTCAATTCTGGAAGAATTCCAGACATTAAA |
| 10 | AAAGAAGGTCTTCATTACACCTGCAGCTCTCAGCTCTCATTTTCCATTTTCCA::::GTCAGTATCAATTCAATTCTGGAAGAATTCCAGACATTAAA |
| 12 | AAAGAAGGTCTTCATTACACCTGCAGCTCTCAGCTCTCATTTTCCATTTTCCATAC::::GTATCAATTCAATTCTGGAAGAATTCCAGACATTAAA |

Figure 12

SEQUENCE LISTING

```
<160> NUMBER OF SEQ ID NOS: 170

<210> SEQ ID NO 1
<211> LENGTH: 35
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (1)..(11)
<223> OTHER INFORMATION: Any amino acid and this region may encompass 1
      to 11 residues
<220> FEATURE:
<221> NAME/KEY: MOD_RES
```

```
<222> LOCATION: (12)..(13)
<223> OTHER INFORMATION: Any amino acid
<220> FEATURE:
<221> NAME/KEY: MOD_RES
<222> LOCATION: (14)..(35)
<223> OTHER INFORMATION: Any amino acid and this region may encompass 20
      to 22 residues
<220> FEATURE:
<223> OTHER INFORMATION: see specification as filed for detailed
      description of substitutions and preferred embodiments

<400> SEQUENCE: 1

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa
        35

<210> SEQ ID NO 2
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Leu Asp Thr Gly Gln Leu Leu Lys Ile Ala Lys Arg Gly Gly Val Thr
1               5                   10                  15

Ala Val Glu Ala Val His Ala Trp Arg Asn Ala Leu Thr Gly Ala Pro
                20                  25                  30

Leu Asn

<210> SEQ ID NO 3
<211> LENGTH: 35
<212> TYPE: PRT
<213> ORGANISM: Xanthomonas oryzae

<400> SEQUENCE: 3

Ala Thr His Glu Ala Ile Val Gly Val

```
<400> SEQUENCE: 5

Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 6
<211> LENGTH: 35
<212> TYPE: PRT
<213> ORGANISM: Xanthomonas oryzae

<400> SEQUENCE: 6

Ala Thr His Glu Asp Ile Val Gly Val Gly Lys Gln Leu Ser Gly Ala
1               5                   10                  15

Arg Ala Leu Glu Ala Leu Leu Thr Lys Ala Gly Glu Leu Arg Gly Pro
            20                  25                  30

Pro Leu Gln
        35

<210> SEQ ID NO 7
<211> LENGTH: 34
<212> TYPE: PRT
<213> ORGANISM: Xanthomonas oryzae

<400> SEQUENCE: 7

Leu Asp Thr Gly Gln Leu Leu Lys Ile Ala Arg Arg Gly Gly Val Thr
1               5                   10                  15

Ala Val Glu Ala Val

-continued

```
<211> LENGTH: 34
<212> TYPE: PRT
<213> ORGANISM: Ralstonia solanacearum

<400> SEQUENCE to 21 residues

<400> SEQUENCE: 13

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 14
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any amino acid and this region may encompass 3
      to 4 residues
<220> FEATURE:
<221> NAME/KEY: MOD_RES
<222> LOCATION: (5)..(5)
<223> OTHER INFORMATION: Ala or Thr
<220> FEATURE:
<221> NAME/KEY: MOD_RES
<222> LOCATION: (6)..(22)
<223> OTHER INFORMATION: Any amino acid and this region may encompass 16
      to 17 residues

<400> SEQUENCE: 14

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 15
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Any amino acid and this region may encompass 4
      to 5 residues
<220> FEATURE:
<221> NAME/KEY: MOD_RES
<222> LOCATION: (6)..(6)
<223> OTHER INFORMATION: Leu or Val
<220> FEATURE:
<221> NAME/KEY: MOD_RES
<222> LOCATION: (7)..(22)
<223> OTHER INFORMATION: Any amino acid and this region may encompass 15
      to 16 residues

<400> SEQUENCE: 15

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Thr Gly Glu Lys Pro
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Gly Gly Gln Arg Pro
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Gly Gln Lys Pro
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Gly Ser Gln Lys Pro
1               5

<210> SEQ ID NO 20
<211> LENGTH: 17
<212> TYPE: DNA
<213> ORGANISM: Homo sapiens

<400> SEQUENCE: 20
tcattacacc tgcagct                                                  17

<210> SEQ ID NO 21
<211> LENGTH: 79
<212> TYPE: DNA
<213> ORGANISM: Homo sapiens

<400> SEQUENCE: 21
aaaaagaagg tcttcattac acctgcagct ctcattttcc atacagtcag tatcaattct   60
ggaagaattt ccagacatt                                                79

<210> SEQ ID NO 22
<211> LENGTH: 17
<212> TYPE: DNA
<213> ORGANISM: Homo sapiens

<400> SEQUENCE: 22
cttccagaat tgatact                                                                17

<210> SEQ ID NO 23
<211> LENGTH: 583
<212> TYPE: PRT
<213> ORGANISM: Planomicrobium okeanokoites

<400> SEQUENCE: 23

```
Met Phe Leu Ser Met Val Ser Lys Ile Arg Thr Phe Gly Trp Val Gln
1               5                   10                  15

Asn Pro Gly Lys Phe Glu Asn Leu Lys Arg Val Val Gln Val Phe Asp
            20                  25                  30

Arg Asn Ser Lys Val His Asn Glu Val Lys Asn Ile Lys Ile Pro Thr
        35                  40                  45

Leu Val Lys Glu Ser Lys Ile Gln Lys Glu Leu Val Ala Ile Met Asn
    50                  55                  60

Gln His Asp Leu Ile Tyr Thr Tyr Lys Glu Leu Val Gly Thr Gly Thr
65                  70                  75                  80

Ser Ile Arg Ser Glu Ala Pro Cys Asp Ala Ile Ile Gln Ala Thr Ile
                85                  90                  95

Ala Asp Gln Gly Asn Lys Lys Gly Tyr Ile Asp Asn Trp Ser Ser Asp
            100                 105                 110

Gly Phe Leu Arg Trp Ala His Ala Leu Gly Phe Ile Glu Tyr Ile Asn
        115                 120                 125

Lys Ser Asp Ser Phe Val Ile Thr Asp Val Gly Leu Ala Tyr Ser Lys
    130                 135                 140

Ser Ala Asp Gly Ser Ala Ile Glu Lys Glu Ile Leu Ile Glu Ala Ile
145                 150                 155                 160

Ser Ser Tyr Pro Pro Ala Ile Arg Ile Leu Thr Leu Leu Glu Asp Gly
                165                 170                 175

Gln His Leu Thr Lys Phe Asp Leu Gly Lys Asn Leu Gly Phe Ser Gly
            180                 185                 190

Glu Ser Gly Phe Thr Ser Leu Pro Glu Gly Ile Leu Leu Asp Thr Leu
        195                 200                 205

Ala Asn Ala Met Pro Lys Asp Lys Gly Glu Ile Arg Asn Asn Trp Glu
    210                 215                 220

Gly Ser Ser Asp Lys Tyr Ala Arg Met Ile Gly Gly Trp Leu Asp Lys
225                 230                 235                 240

Leu Gly Leu Val Lys Gln Gly Lys Lys Glu Phe Ile Ile Pro Thr Leu
                245                 250                 255

Gly Lys Pro Asp Asn Lys Glu Phe Ile Ser His Ala Phe Lys Ile Thr
            260                 265                 270

Gly Glu Gly Leu Lys Val Leu Arg Arg Ala Lys Gly Ser Thr Lys Phe
        275                 280                 285

Thr Arg Val Pro Lys Arg Val Tyr Trp Glu Met Leu Ala Thr Asn Leu
    290                 295                 300

Thr Asp Lys Glu Tyr Val Arg Thr Arg Arg Ala Leu Ile Leu Glu Ile
305                 310                 315                 320

Leu Ile Lys Ala Gly Ser Leu Lys Ile Glu Gln Ile Gln Asp Asn Leu
                325                 330                 335

Lys Lys Leu Gly Phe Asp Glu Val Ile Glu Thr Ile Glu Asn Asp Ile
            340                 345                 350

Lys Gly Leu Ile Asn Thr Gly Ile Phe Ile Glu Ile Lys Gly Arg Phe
        355                 360                 365
```

```
Tyr Gln Leu Lys Asp His Ile Leu Gln Phe Val Ile Pro Asn Arg Gly
    370                 375                 380

Val Thr Lys Gln Leu Val Lys Ser Glu Leu Glu Glu Lys Lys Ser Glu
385                 390                 395                 400

Leu Arg His Lys Leu Lys Tyr Val Pro His Glu Tyr Ile Glu Leu Ile
                405                 410                 415

Glu Ile Ala Arg Asn Ser Thr Gln Asp Arg Ile Leu Glu Met Lys Val
            420                 425                 430

Met Glu Phe Phe Met Lys Val Tyr Gly Tyr Arg Gly Lys His Leu Gly
        435                 440                 445

Gly Ser Arg Lys Pro Asp Gly Ala Ile Tyr Thr Val Gly Ser Pro Ile
450                 455                 460

Asp Tyr Gly Val Ile Val Asp Thr Lys Ala Tyr Ser Gly Gly Tyr Asn
465                 470                 475                 480

Leu Pro Ile Gly Gln Ala Asp Glu Met Gln Arg Tyr Val Glu Glu Asn
                485                 490                 495

Gln Thr Arg Asn Lys His Ile Asn Pro Asn Glu Trp Trp Lys Val Tyr
            500                 505                 510

Pro Ser Ser Val Thr Glu Phe Lys Phe Leu Phe Val Ser Gly His Phe
        515                 520                 525

Lys Gly Asn Tyr Lys Ala Gln Leu Thr Arg Leu Asn His Ile Thr Asn
530                 535                 540

Cys Asn Gly Ala Val Leu Ser Val Glu Glu Leu Leu Ile Gly Gly Glu
545                 550                 555                 560

Met Ile Lys Ala Gly Thr Leu Thr Leu Glu Glu Val Arg Arg Lys Phe
                565                 570                 575

Asn Asn Gly Glu Ile Asn Phe
            580

<210> SEQ ID NO 24
<211> LENGTH: 579
<212> TYPE: PRT
<213> ORGANISM: Planomicrobium okeanokoites

<400> SEQUENCE: 24

Met Val Ser Lys Ile Arg Thr Phe Gly Trp Val Gln Asn Pro Gly Lys
1               5                   10                  15

Phe Glu Asn Leu Lys Arg Val Val Gln Val Phe Asp Arg Asn Ser Lys
            20                  25                  30

Val His Asn Glu Val Lys Asn Ile Lys Ile Pro Thr Leu Val Lys Glu
        35                  40                  45

Ser Lys Ile Gln Lys Glu Leu Val Ala Ile Met Asn Gln His Asp Leu
    50                  55                  60

Ile Tyr Thr Tyr Lys Glu Leu Val Gly Thr Gly Thr Ser Ile Arg Ser
65                  70                  75                  80

Glu Ala Pro Cys Asp Ala Ile Ile Gln Ala Thr Ile Ala Asp Gln Gly
                85                  90                  95

Asn Lys Lys Gly Tyr Ile Asp Asn Trp Ser Ser Asp Gly Phe Leu Arg
            100                 105                 110

Trp Ala His Ala Leu Gly Phe Ile Glu Tyr Ile Asn Lys Ser Asp Ser
        115                 120                 125

Phe Val Ile Thr Asp Val Gly Leu Ala Tyr Ser Lys Ser Ala Asp Gly
    130                 135                 140

Ser Ala Ile Glu Lys Glu Ile Leu Ile Glu Ala Ile Ser Ser Tyr Pro
145                 150                 155                 160
```

```
Pro Ala Ile Arg Ile Leu Thr Leu Leu Glu Asp Gly Gln His Leu Thr
            165                 170                 175

Lys Phe Asp Leu Gly Lys Asn Leu Gly Phe Ser Gly Glu Ser Gly Phe
        180                 185                 190

Thr Ser Leu Pro Glu Gly Ile Leu Leu Asp Thr Leu Ala Asn Ala Met
        195                 200                 205

Pro Lys Asp Lys Gly Glu Ile Arg Asn Asn Trp Glu Gly Ser Ser Asp
    210                 215                 220

Lys Tyr Ala Arg Met Ile Gly Gly Trp Leu Asp Lys Leu Gly Leu Val
225                 230                 235                 240

Lys Gln Gly Lys Lys Glu Phe Ile Ile Pro Thr Leu Gly Lys Pro Asp
                245                 250                 255

Asn Lys Glu Phe Ile Ser His Ala Phe Lys Ile Thr Gly Glu Gly Leu
            260                 265                 270

Lys Val Leu Arg Arg Ala Lys Gly Ser Thr Lys Phe Thr Arg Val Pro
        275                 280                 285

Lys Arg Val Tyr Trp Glu Met Leu Ala Thr Asn Leu Thr Asp Lys Glu
    290                 295                 300

Tyr Val Arg Thr Arg Arg Ala Leu Ile Leu Glu Ile Leu Ile Lys Ala
305                 310                 315                 320

Gly Ser Leu Lys Ile Glu Gln Ile Gln Asp Asn Leu Lys Lys Leu Gly
                325                 330                 335

Phe Asp Glu Val Ile Glu Thr Ile Glu Asn Asp Ile Lys Gly Leu Ile
            340                 345                 350

Asn Thr Gly Ile Phe Ile Glu Ile Lys Gly Arg Phe Tyr Gln Leu Lys
        355                 360                 365

Asp His Ile Leu Gln Phe Val Ile Pro Asn Arg Leu Gly Lys Pro Asp
    370                 375                 380

Leu Val Lys Ser Glu Leu Glu Glu Lys Lys Ser Glu Leu Arg His Lys
385                 390                 395                 400

Leu Lys Tyr Val Pro His Glu Tyr Ile Glu Leu Ile Glu Ile Ala Arg
                405                 410                 415

Asn Ser Thr Gln Asp Arg Ile Leu Glu Met Lys Val Met Glu Phe Phe
            420                 425                 430

Met Lys Val Tyr Gly Tyr Arg Gly Lys His Leu Gly Gly Ser Arg Lys
        435                 440                 445

Pro Asp Gly Ala Ile Tyr Thr Val Gly Ser Pro Ile Asp Tyr Gly Val
    450                 455                 460

Ile Val Asp Thr Lys Ala Tyr Ser Gly Gly Tyr Asn Leu Pro Ile Gly
465                 470                 475                 480

Gln Ala Asp Glu Met Gln Arg Tyr Val Glu Glu Asn Gln Thr Arg Asn
                485                 490                 495

Lys His Ile Asn Pro Asn Glu Trp Trp Lys Val Tyr Pro Ser Ser Val
            500                 505                 510

Thr Glu Phe Lys Phe Leu Phe Val Ser Gly His Phe Lys Gly Asn Tyr
        515                 520                 525

Lys Ala Gln Leu Thr Arg Leu Asn His Ile Thr Asn Cys Asn Gly Ala
    530                 535                 540

Val Leu Ser Val Glu Glu Leu Leu Ile Gly Gly Glu Met Ile Lys Ala
545                 550                 555                 560

Gly Thr Leu Thr Leu Glu Glu Val Arg Arg Lys Phe Asn Asn Gly Glu
                565                 570                 575
```

Ile Asn Phe

<210> SEQ ID NO 25
<211> LENGTH: 22
<212> TYPE: PRT
<213> ORGANISM: Planomicrobium okeanokoites

<400> SEQUENCE: 25

Gln Phe Val Ile Pro Asn Arg Gly Val Thr Lys Gln Leu Val Lys Ser
1               5                   10                  15

Glu Leu Glu Glu Lys Lys
            20

<210> SEQ ID NO 26
<211> LENGTH: 22
<212> TYPE: PRT
<213> ORGANISM: Planomicrobium okeanokoites

<400> SEQUENCE: 26

Gln Phe Val Ile Pro Asn Arg Leu Gly Lys Pro Asp Leu Val Lys Ser
1               5                   10                  15

Glu Leu Glu Glu Lys Lys
            20

<210> SEQ ID NO 27
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Leu Val Lys Ser Glu Leu Glu Glu Lys Lys Ser Glu Leu Arg His Lys
1               5                   10                  15

Leu Lys Tyr Val Pro His Glu Tyr Ile Glu Leu Ile Glu Ile Ala Arg
            20                  25                  30

Asn Ser Thr Gln Asp Arg Ile Leu Glu Met Lys Val Met Glu Phe Phe
        35                  40                  45

Met Lys Val Tyr Gly Tyr Arg Gly Lys His Leu Gly Gly Ser Arg Lys
    50                  55                  60

Pro Asp
65

<210> SEQ ID NO 28
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Val Lys Ser Glu Leu Glu Glu Lys Lys Ser Glu Leu Arg His Lys Leu
1               5                   10                  15

Lys Tyr Val Pro His Glu Tyr Ile Glu Leu Ile Glu Ile Ala Arg Asn
            20                  25                  30

Ser Thr Gln Asp Arg Ile Leu Glu Met Lys Val Met Glu Phe Phe Met
        35                  40                  45

Lys Val Tyr Gly Tyr Arg Gly Lys His Leu Gly Gly Ser Arg Lys Pro
    50                  55                  60

Asp
65

<210> SEQ ID NO 29
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Lys Ser Glu Leu Glu Glu Lys Lys Ser Glu Leu Arg His Lys Leu Lys
1               5                   10                  15

Tyr Val Pro His Glu Tyr Ile Glu Leu Ile Glu Ile Ala Arg Asn Ser
            20                  25                  30

Thr Gln Asp Arg Ile Leu Glu Met Lys Val Met Glu Phe Phe Met Lys
        35                  40                  45

Val Tyr Gly Tyr Arg Gly Lys His Leu Gly Gly Ser Arg Lys Pro Asp
    50                  55                  60

<210> SEQ ID NO 30
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser Glu Leu Glu Glu Lys Lys Ser Glu Leu Arg His Lys Leu Lys Tyr
1               5                   10                  15

Val Pro His Glu Tyr Ile Glu Leu Ile Glu Ile Ala Arg Asn Ser Thr
            20                  25                  30

Gln Asp Arg Ile Leu Glu Met Lys Val Met Glu Phe Phe Met Lys Val
        35                  40                  45

Tyr Gly Tyr Arg Gly Lys His Leu Gly Gly Ser Arg Lys Pro Asp
    50                  55                  60

<210> SEQ ID NO 31
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Leu Glu Glu Lys Lys Ser Glu Leu Arg His Lys Leu Lys Tyr Val
1               5                   10                  15

Pro His Glu Tyr Ile Glu Leu Ile Glu Ile Ala Arg Asn Ser Thr Gln
            20                  25                  30

Asp Arg Ile Leu Glu Met Lys Val Met Glu Phe Phe Met Lys Val Tyr
        35                  40                  45

Gly Tyr Arg Gly Lys His Leu Gly Gly Ser Arg Lys Pro Asp
    50                  55                  60

<210> SEQ ID NO 32
<211> LENGTH: 61
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 32

Leu Glu Glu Lys Lys Ser Glu Leu Arg His Lys Leu Lys Tyr Val Pro
1               5                   10                  15

His Glu Tyr Ile Glu Leu Ile Glu Ile Ala Arg Asn Ser Thr Gln Asp
            20                  25                  30

Arg Ile Leu Glu Met Lys Val Met Glu Phe Phe Met Lys Val Tyr Gly
        35                  40                  45

Tyr Arg Gly Lys His Leu Gly Gly Ser Arg Lys Pro Asp
    50                  55                  60

<210> SEQ ID NO 33
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Glu Lys Lys Ser Glu Leu Arg His Lys Leu Lys Tyr Val Pro His
1               5                   10                  15

Glu Tyr Ile Glu Leu Ile Glu Ile Ala Arg Asn Ser Thr Gln Asp Arg
            20                  25                  30

Ile Leu Glu Met Lys Val Met Glu Phe Phe Met Lys Val Tyr Gly Tyr
        35                  40                  45

Arg Gly Lys His Leu Gly Gly Ser Arg Lys Pro Asp
    50                  55                  60

<210> SEQ ID NO 34
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Lys Lys Ser Glu Leu Arg His Lys Leu Lys Tyr Val Pro His Glu
1               5                   10                  15

Tyr Ile Glu Leu Ile Glu Ile Ala Arg Asn Ser Thr Gln Asp Arg Ile
            20                  25                  30

Leu Glu Met Lys Val Met Glu Phe Phe Met Lys Val Tyr Gly Tyr Arg
        35                  40                  45

Gly Lys His Leu Gly Gly Ser Arg Lys Pro Asp
    50                  55

<210> SEQ ID NO 35
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Lys Lys Ser Glu Leu Arg His Lys Leu Lys Tyr Val Pro His Glu
1               5                   10                  15

Tyr Ile Glu Leu Ile Glu Ile Ala Arg Asn Ser Thr Gln Asp Arg Ile
            20                  25                  30

Leu Glu Met Lys Val Met Glu Phe Phe Met Lys Val Tyr Gly Tyr Arg
            35                  40                  45

Gly Lys His Leu Gly Gly Ser Arg Lys Pro Asp
    50                  55

<210> SEQ ID NO 36
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Lys Lys Ser Glu Leu Arg His Lys Leu Lys Tyr Val Pro His Glu Tyr
1               5                   10                  15

Ile Glu Leu Ile Glu Ile Ala Arg Asn Ser Thr Gln Asp Arg Ile Leu
            20                  25                  30

Glu Met Lys Val Met Glu Phe Phe Met Lys Val Tyr Gly Tyr Arg Gly
        35                  40                  45

Lys His Leu Gly Gly Ser Arg Lys Pro Asp
    50                  55

<210> SEQ ID NO 37
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Lys Ser Glu Leu Arg His Lys Leu Lys Tyr Val Pro His Glu Tyr Ile
1               5                   10                  15

Glu Leu Ile Glu Ile Ala Arg Asn Ser Thr Gln Asp Arg Ile Leu Glu
            20                  25                  30

Met Lys Val Met Glu Phe Phe Met Lys Val Tyr Gly Tyr Arg Gly Lys
        35                  40                  45

His Leu Gly Gly Ser Arg Lys Pro Asp
    50                  55

<210> SEQ ID NO 38
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser Glu Leu Arg His Lys Leu Lys Tyr Val Pro His Glu Tyr Ile Glu
1               5                   10                  15

Leu Ile Glu Ile Ala Arg Asn Ser Thr Gln Asp Arg Ile Leu Glu Met
            20                  25                  30

Lys Val Met Glu Phe Phe Met Lys Val Tyr Gly Tyr Arg Gly Lys His
        35                  40                  45

Leu Gly Gly Ser Arg Lys Pro Asp
    50                  55

<210> SEQ ID NO 39
<211> LENGTH: 55
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 39

Glu Leu Arg His Lys Leu Lys Tyr Val Pro His Glu Tyr Ile Glu Leu
1               5                   10                  15

Ile Glu Ile Ala Arg Asn Ser Thr Gln Asp Arg Ile Leu Glu Met Lys
            20                  25                  30

Val Met Glu Phe Phe Met Lys Val Tyr Gly Tyr Arg Gly Lys His Leu
        35                  40                  45

Gly Gly Ser Arg Lys Pro Asp
    50                  55

<210> SEQ ID NO 40
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Leu Arg His Lys Leu Lys Tyr Val Pro His Glu Tyr Ile Glu Leu Ile
1               5                   10                  15

Glu Ile Ala Arg Asn Ser Thr Gln Asp Arg Ile Leu Glu Met Lys Val
            20                  25                  30

Met Glu Phe Phe Met Lys Val Tyr Gly Tyr Arg Gly Lys His Leu Gly
        35                  40                  45

Gly Ser Arg Lys Pro Asp
    50

<210> SEQ ID NO 41
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Arg His Lys Leu Lys Tyr Val Pro His Glu Tyr Ile Glu Leu Ile Glu
1               5                   10                  15

Ile Ala Arg Asn Ser Thr Gln Asp Arg Ile Leu Glu Met Lys Val Met
            20                  25                  30

Glu Phe Phe Met Lys Val Tyr Gly Tyr Arg Gly Lys His Leu Gly Gly
        35                  40                  45

Ser Arg Lys Pro Asp
    50

<210> SEQ ID NO 42
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

His Lys Leu Lys Tyr Val Pro His Glu Tyr Ile Glu Leu Ile Glu Ile
1               5                   10                  15

Ala Arg Asn Ser Thr Gln Asp Arg Ile Leu Glu Met Lys Val Met Glu
            20                  25                  30

Phe Phe Met Lys Val Tyr Gly Tyr Arg Gly Lys His Leu Gly Gly Ser
        35                  40                  45

Arg Lys Pro Asp
    50

<210> SEQ ID NO 43
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Lys Leu Lys Tyr Val Pro His Glu Tyr Ile Glu Leu Ile Glu Ile Ala
1               5                   10                  15

Arg Asn Ser Thr Gln Asp Arg Ile Leu Glu Met Lys Val Met Glu Phe
            20                  25                  30

Phe Met Lys Val Tyr Gly Tyr Arg Gly Lys His Leu Gly Gly Ser Arg
        35                  40                  45

Lys Pro Asp
    50

<210> SEQ ID NO 44
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Leu Lys Tyr Val Pro His Glu Tyr Ile Glu Leu Ile Glu Ile Ala Arg
1               5                   10                  15

Asn Ser Thr Gln Asp Arg Ile Leu Glu Met Lys Val Met Glu Phe Phe
            20                  25                  30

Met Lys Val Tyr Gly Tyr Arg Gly Lys His Leu Gly Gly Ser Arg Lys
        35                  40                  45

Pro Asp
    50

<210> SEQ ID NO 45
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Lys Tyr Val Pro His Glu Tyr Ile Glu Leu Ile Glu Ile Ala Arg Asn
1               5                   10                  15

Ser Thr Gln Asp Arg Ile Leu Glu Met Lys Val Met Glu Phe Phe Met
            20                  25                  30

Lys Val Tyr Gly Tyr Arg Gly Lys His Leu Gly Gly Ser Arg Lys Pro
        35                  40                  45

Asp

<210> SEQ ID NO 46

```
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Tyr Val Pro His Glu Tyr Ile Glu Leu Ile Glu Ile Ala Arg Asn Ser
1               5                   10                  15

Thr Gln Asp Arg Ile Leu Glu Met Lys Val Met Glu Phe Phe Met Lys
            20                  25                  30

Val Tyr Gly Tyr Arg Gly Lys His Leu Gly Gly Ser Arg Lys Pro Asp
        35                  40                  45

<210> SEQ ID NO 47
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Val Pro His Glu Tyr Ile Glu Leu Ile Glu Ile Ala Arg Asn Ser Thr
1               5                   10                  15

Gln Asp Arg Ile Leu Glu Met Lys Val Met Glu Phe Phe Met Lys Val
            20                  25                  30

Tyr Gly Tyr Arg Gly Lys His Leu Gly Gly Ser Arg Lys Pro Asp
        35                  40                  45

<210> SEQ ID NO 48
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Phe Val Ile Pro Asn Arg Gly Val Thr Lys Gln Leu Val Lys Ser
1               5                   10                  15

Glu Leu Glu Glu Lys Lys
            20

<210> SEQ ID NO 49
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Phe Val Ile Pro Asn Arg Leu Gly Lys Pro Asp Leu Val Lys Ser
1               5                   10                  15

Glu Leu Glu Glu Lys Lys
            20

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
```

```
                         peptide

<400> SEQUENCE: 50

Gly Val Thr Lys Gln Leu Val Ser Glu Leu Glu Glu Lys Lys
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Thr Lys Gln Leu Val Ser Glu Leu Glu Glu Lys Lys
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Lys Gln Leu Val Ser Glu Leu Glu Glu Lys Lys
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Gln Leu Val Ser Glu Leu Glu Glu Lys Lys
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Leu Gly Lys Pro Asp Leu Val Ser Glu Leu Glu Glu Lys Lys
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Lys Pro Asp Leu Val Ser Glu Leu Glu Glu Lys Lys
1               5                   10

<210> SEQ ID NO 56
```

-continued

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Pro Asp Leu Val Ser Glu Leu Glu Glu Lys Lys
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Pro Asp Leu Val Ser Glu Leu Glu Glu Lys Lys
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Leu Val Ser Glu Leu Glu Glu Lys Lys
1               5                   10

<210> SEQ ID NO 59
<211> LENGTH: 35
<212> TYPE: PRT
<213> ORGANISM: Xanthomonas oryzae

<400> SEQUENCE: 59

Ala Thr His Glu Asp Ile Val Gly Val Gly Lys Gln Leu Ser Gly Ala
1               5                   10                  15

Arg Ala Leu Glu Ala Leu Leu Thr Lys Ala Gly Glu Leu Arg Gly Pro
            20                  25                  30

Pro Leu Gln
        35

<210> SEQ ID NO 60
<211> LENGTH: 35
<212> TYPE: PRT
<213> ORGANISM: Ralstonia solanacearum

<400> SEQUENCE: 60

Leu Thr Arg Ala His Ile Val Asp Ile Ala Arg Gln Arg Ser Gly Asp
1               5                   10                  15

Leu Ala Leu Gln Ala Leu Leu Pro Val Ala Thr Ala Leu Thr Ala Ala
            20                  25                  30

Pro Leu Arg
        35

<210> SEQ ID NO 61
<211> LENGTH: 35
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 61

Ala Thr His Glu Ala Ile Val Gly Val Gly Lys Gln Phe Ser Gly Ala
1               5                   10                  15

Arg Ala Leu Glu Ala Leu Leu Thr Val Ala Gly Glu Leu Arg Gly Pro
            20                  25                  30

Pro Leu Gln
        35

<210> SEQ ID NO 62
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Thr His Glu Ala Ile Val Gly Val Gly Lys Gln His Ser Gly Ala
1               5                   10                  15

Arg Ala Leu Glu Ala Leu Leu Thr Val Ala Gly Glu Leu Arg Gly Pro
            20                  25                  30

Pro Leu Gln
        35

<210> SEQ ID NO 63
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Ala Thr His Glu Ala Ile Val Gly Val Gly Lys Gln Ile Ser Gly Ala
1               5                   10                  15

Arg Ala Leu Glu Ala Leu Leu Thr Val Ala Gly Glu Leu Arg Gly Pro
            20                  25                  30

Pro Leu Gln
        35

<210> SEQ ID NO 64
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ala Thr His Glu Ala Ile Val Gly Val Gly Lys Gln Lys Ser Gly Ala
1               5                   10                  15

Arg Ala Leu Glu Ala Leu Leu Thr Val Ala Gly Glu Leu Arg Gly Pro
            20                  25                  30

Pro Leu Gln
        35

<210> SEQ ID NO 65
<211> LENGTH: 35
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 65

Ala Thr His Glu Ala Ile Val Gly Val Gly Lys Gln Leu Ser Gly Ala
1               5                   10                  15

Arg Ala Leu Glu Ala Leu Leu Thr Val Ala Gly Glu Leu Arg Gly Pro
            20                  25                  30

Pro Leu Gln
        35

<210> SEQ ID NO 66
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Ala Thr His Glu Ala Ile Val Gly Val Gly Lys Gln Asn Ser Gly Ala
1               5                   10                  15

Arg Ala Leu Glu Ala Leu Leu Thr Val Ala Gly Glu Leu Arg Gly Pro
            20                  25                  30

Pro Leu Gln
        35

<210> SEQ ID NO 67
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Ala Thr His Glu Ala Ile Val Gly Val Gly Lys Gln Gln Ser Gly Ala
1               5                   10                  15

Arg Ala Leu Glu Ala Leu Leu Thr Val Ala Gly Glu Leu Arg Gly Pro
            20                  25                  30

Pro Leu Gln
        35

<210> SEQ ID NO 68
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Thr His Glu Ala Ile Val Gly Val Gly Lys Gln Arg Ser Gly Ala
1               5                   10                  15

Arg Ala Leu Glu Ala Leu Leu Thr Val Ala Gly Glu Leu Arg Gly Pro
            20                  25                  30

Pro Leu Gln
        35

<210> SEQ ID NO 69
<211> LENGTH: 35
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Thr His Glu Ala Ile Val Gly Val Gly Lys Gln Val Ser Gly Ala
1               5                  10                  15

Arg Ala Leu Glu Ala Leu Leu Thr Val Ala Gly Glu Leu Arg Gly Pro
            20                  25                  30

Pro Leu Gln
        35

<210> SEQ ID NO 70
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Thr His Glu Ala Ile Val Gly Val Gly Lys Gln Tyr Ser Gly Ala
1               5                  10                  15

Arg Ala Leu Glu Ala Leu Leu Thr Val Ala Gly Glu Leu Arg Gly Pro
            20                  25                  30

Pro Leu Gln
        35

<210> SEQ ID NO 71
<211> LENGTH: 34
<212> TYPE: PRT
<213> ORGANISM: Xanthomonas oryzae

<400> SEQUENCE: 71

Leu Asp Thr Gly Gln Leu Leu Lys Ile Ala Arg Arg Gly Gly Val Thr
1               5                  10                  15

Ala Val Glu Ala Val His Ala Trp Arg Asn Ala Leu Thr Gly Ala Pro
            20                  25                  30

Leu Asn

<210> SEQ ID NO 72
<211> LENGTH: 34
<212> TYPE: PRT
<213> ORGANISM: Ralstonia solanacearum

<400> SEQUENCE: 72

Leu Ser Ala Ser Gln Ile Ala Thr Val Ala Gln Tyr Gly Glu Arg Pro
1               5                  10                  15

Ala Ile Gln Ala Leu Tyr Arg Leu Arg Arg Lys Leu Thr Arg Ala Pro
            20                  25                  30

Leu His

<210> SEQ ID NO 73
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73
```

```
Leu Asp Thr Gly Gln Leu Leu Lys Ile Ala Lys Arg Ile Gly Gly Val
1               5                   10                  15

Thr Ala Val Glu Ala Val His Ala Trp Arg Asn Ala Leu Thr Gly Ala
            20                  25                  30

Pro Leu Asn
        35

<210> SEQ ID NO 74
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Leu Asp Thr Gly Gln Leu Leu Lys Ile Ala Lys Arg Asp Gly Gly Val
1               5                   10                  15

Thr Ala Val Glu Ala Val His Ala Trp Arg Asn Ala Leu Thr Gly Ala
            20                  25                  30

Pro Leu Asn
        35

<210> SEQ ID NO 75
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Leu Asp Thr Gly Gln Leu Leu Lys Ile Ala Lys Arg Asn Gly Gly Val
1               5                   10                  15

Thr Ala Val Glu Ala Val His Ala Trp Arg Asn Ala Leu Thr Gly Ala
            20                  25                  30

Pro Leu Asn
        35

<210> SEQ ID NO 76
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Leu Asp Thr Gly Gln Leu Leu Lys Ile Ala Lys Arg Ser Gly Gly Val
1               5                   10                  15

Thr Ala Val Glu Ala Val His Ala Trp Arg Asn Ala Leu Thr Gly Ala
            20                  25                  30

Pro Leu Asn
        35

<210> SEQ ID NO 77
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 77

Ala Thr His Glu Ala Ile Val Gly Val Gly Lys Gln Leu Ser Gly Ala
1               5                   10                  15

Arg Ala Leu Glu Ala Leu Leu Thr Val Ala Gly Glu Leu Arg Gly Pro
            20                  25                  30

Pro Leu Gln
        35

<210> SEQ ID NO 78
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Leu Asp Thr Gly Gln Leu Leu Lys Ile Ala Lys Arg Ile Gly Gly Val
1               5                   10                  15

Thr Ala Val Glu Ala Val His Ala Trp Arg Asn Ala Leu Thr Gly Ala
            20                  25                  30

Pro Leu Asn
        35

<210> SEQ ID NO 79
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Leu Asp Thr Gly Gln Leu Leu Lys Ile Ala Lys Arg Asp Gly Gly Val
1               5                   10                  15

Thr Ala Val Glu Ala Val His Ala Trp Arg Asn Ala Leu Thr Gly Ala
            20                  25                  30

Pro Leu Asn
        35

<210> SEQ ID NO 80
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Leu Asp Thr Gly Gln Leu Leu Lys Ile Ala Lys Arg Asn Gly Gly Val
1               5                   10                  15

Thr Ala Val Glu Ala Val His Ala Trp Arg Asn Ala Leu Thr Gly Ala
            20                  25                  30

Pro Leu Asn
        35

<210> SEQ ID NO 81
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 81

Leu Asp Thr Gly Gln Leu Leu Lys Ile Ala Lys Arg His Gly Val
1               5                   10                  15

Thr Ala Val Glu Ala Val His Ala Trp Arg Asn Ala Leu Thr Gly Ala
            20                  25                  30

Pro Leu Asn
        35

<210> SEQ ID NO 82
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ttgacaatcc t                                                              11

<210> SEQ ID NO 83
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ttgaccatcc t                                                              11

<210> SEQ ID NO 84
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ttgacgatcc t                                                              11

<210> SEQ ID NO 85
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ttgactatcc t                                                              11

<210> SEQ ID NO 86
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Thr His Glu Ala Ile Val Gly Val Gly Lys Gln Trp Ser Gly Ala
1               5                   10                  15

Arg Ala Leu Glu Ala Leu Leu Thr Val Ala Gly Glu Leu Arg Gly Pro 20                  25                  30

Pro Leu Gln
        35

<210> SEQ ID NO 87
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: a, c, t, g, unknown or other

<400> SEQUENCE: 87
actgggnnnn n                                                              11

<210> SEQ ID NO 88
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other

<400> SEQUENCE: 88 nnnncccagt                                                                10

<210> SEQ ID NO 89
<211> LENGTH: 1002
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Arg Gly Val Pro Met Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

```
Glu Ala Val His Ala Trp Arg Asn Ala Leu Thr Gly Ala Pro Leu Asn
                165                 170                 175

Leu Thr Pro Asp Gln Val Val Ala Ile Ala Ser Asn Gly Gly Gly Lys
            180                 185                 190

Gln Ala Leu Glu Thr Val Gln Arg Leu Leu Pro Val Leu Cys Gln Asp
        195                 200                 205

His Gly Leu Thr Pro Glu Gln Val Val Ala Ile Ala Ser His Asp Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Ser Asn
            245                 250                 255

Ile Gly Gly Lys Gln Ala Leu Glu Thr Val Gln Arg Leu Leu Pro Val
        260                 265                 270

Leu Cys Gln Ala His Gly Leu Thr Pro Ala Gln Val Val Ala Ile Ala
    275                 280                 285

Ser Asn Gly Gly Gly Lys Gln Ala Leu Glu Thr Val Gln Arg Leu Leu
    290                 295                 300

Pro Val Leu Cys Gln Asp His Gly Leu Thr Pro Asp Gln Val Val Ala
305                 310                 315                 320

Ile Ala Ser Asn Gly Gly Gly Lys Gln Ala Leu Glu Thr Val Gln Arg
            325                 330                 335

Leu Leu Pro Val Leu Cys Gln Asp His Gly Leu Thr Pro Glu Gln Val
        340                 345                 350

Val Ala Ile Ala Ser Asn Ile Gly Gly Lys Gln Ala Leu Glu Thr Val
    355                 360                 365

Gln Arg Leu Leu Pro Val Leu Cys Gln Ala His Gly Leu Thr Pro Asp
    370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
            405                 410                 415

Pro Ala Gln Val Val Ala Ile Ala Ser Asn Ile Gly Gly Lys Gln Ala
        420                 425                 430

Leu Glu Thr Val Gln Arg Leu Leu Pro Val Leu Cys Gln Asp His Gly
    435                 440                 445

Leu Thr Pro Asp Gln Val Val Ala Ile Ala Ser His Asp Gly Gly Lys
    450                 455                 460

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Ser His Asp Gly
            485                 490                 495

Gly Lys Gln Ala Leu Glu Thr Val Gln Arg Leu Leu Pro Val Leu Cys
        500                 505                 510

Gln Ala His Gly Leu Thr Pro Asp Gln Val Val Ala Ile Ala Ser Asn
    515                 520                 525

Gly Gly Gly Lys Gln Ala Leu Glu Thr Val Gln Arg Leu Leu Pro Val
    530                 535                 540

Leu Cys Gln Ala His Gly Leu Thr Pro Ala Gln Val Val Ala Ile Ala
545                 550                 555                 560

Asn Asn Asn Gly Gly Lys Gln Ala Leu Glu Thr Val Gln Arg Leu Leu
            565                 570                 575
```

```
Pro Val Leu Cys Gln Asp His Gly Leu Thr Pro Asp Gln Val Val Ala
            580                 585                 590
Ile Ala Ser His Asp Gly Gly Lys Gln Ala Leu Glu Thr Val Gln Arg
        595                 600                 605
Leu Leu Pro Val Leu Cys Gln Asp His Gly Leu Thr Pro Glu Gln Val
    610                 615                 620
Val Ala Ile Ala Ser Asn Ile Gly Gly Lys Gln Ala Leu Glu Thr Val
625                 630                 635                 640
Gln Arg Leu Leu Pro Val Leu Cys Gln Ala His Gly Leu Thr Pro Asp
            645                 650                 655
Gln Val Val Ala Ile Ala Asn Asn Gly Gly Lys Gln Ala Leu Glu
        660                 665                 670
Thr Val Gln Arg Leu Leu Pro Val Leu Cys Gln Ala His Gly Leu Thr
    675                 680                 685
Pro Ala Gln Val Val Ala Ile Ala Ser His Asp Gly Gly Lys Gln Ala
690                 695                 700
Leu Glu Thr Val Gln Arg Leu Leu Pro Val Leu Cys Gln Asp His Gly
705                 710                 715                 720
Leu Thr Pro Glu Gln Val Val Ala Ile Ala Ser Asn Gly Gly Gly Arg
            725                 730                 735
Pro Ala Leu Glu Ser Ile Val Ala Gln Leu Ser Arg Pro Asp Pro Ala
        740                 745                 750
Leu Ala Ala Leu Thr Asn Asp His Leu Val Ala Leu Ala Cys Leu Gly
    755                 760                 765
Gly Arg Pro Ala Leu Asp Ala Val Lys Lys Gly Leu Pro His Ala Pro
770                 775                 780
Ala Leu Ile Lys Arg Thr Asn Arg Arg Ile Pro Glu Arg Thr Ser His
785                 790                 795                 800
Arg Val Ala Gly Ser Asn Phe Phe Ser Leu His Pro Asn Val Tyr Ala
            805                 810                 815
Thr Gly Arg Pro Lys Gly Leu Ile Gly Met Leu Glu Asn Val Trp Val
        820                 825                 830
Ser Asn His Thr Pro Gly Glu Gly Thr Leu Tyr Leu Ile Ser Gly Phe
    835                 840                 845
Ser Asn Tyr Asn Gly Gly Val Arg Phe Tyr Glu Thr Phe Thr Glu His
850                 855                 860
Ile Asn Gln Gly Gly Arg Val Ile Ala Ile Leu Gly Gly Ser Thr Ser
865                 870                 875                 880
Gln Arg Leu Ser Ser Arg Gln Val Val Glu Glu Leu Leu Asn Arg Gly
            885                 890                 895
Val Glu Val His Ile Ile Asn Arg Lys Arg Ile Leu His Ala Lys Leu
        900                 905                 910
Tyr Gly Thr Ser Asn Asn Leu Gly Glu Ser Leu Val Val Ser Ser Gly
    915                 920                 925
Asn Phe Thr Gly Pro Gly Met Ser Gln Asn Ile Glu Ala Ser Leu Leu
930                 935                 940
Leu Asp Asn Asn Thr Thr Gln Ser Met Gly Phe Ser Trp Asn Asp Met
945                 950                 955                 960
Ile Ser Glu Met Leu Asn Gln Asn Trp His Ile His Asn Met Thr Asn
            965                 970                 975
Ala Thr Asp Ala Ser Pro Gly Trp Asn Leu Leu Tyr Asp Glu Arg Thr
        980                 985                 990
Thr Asn Leu Thr Leu Asp Glu Thr  Arg Ser
```

<210> SEQ ID NO 90
<211> LENGTH: 3015
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

```
atggactaca aagaccatga cggtgattat aaagatcatg acatcgatta caaggatgac      60
gatgacaaga tggccccccaa gaagaagagg aaggtgggca ttcaccgcgg ggtacctatg     120
gtggacttga ggacactcgg ttattcgcaa cagcaacagg agaaaatcaa gcctaaggtc     180
aggagcaccg tcgcgcaaca ccacgaggcg cttgtggggc atggcttcac tcatgcgcat     240
attgtcgcgc tttcacagca ccctgcggcg cttgggacgg tggctgtcaa ataccaagat     300
atgattgcgg ccctgcccga agccacgcac gaggcaattg taggggtcgg taaacagtgg     360
tcgggagcgc gagcacttga ggcgctgctg actgtggcgg gtgagcttag ggggcctccg     420
ctccagctcg acaccgggca gctgctgaag atcgcgaaga gaggggagt aacagcggta     480
gaggcagtgc acgcctggcg caatgcgctc accggggccc ccttgaacct gaccccagac     540
caggtagtcg caatcgcgtc gaatggcggg ggaaagcaag ccctggaaac cgtgcaaagg     600
ttgttgccgg tcctttgtca agaccacggc cttacaccgg agcaagtcgt ggccattgca     660
tcacatgacg gtggcaaaca ggctcttgag acggttcaga gacttctccc agttctctgt     720
caagcccacg ggctgactcc cgatcaagtt gtagcgattg cgagcaacat cggagggaaa     780
caagcattgg agactgtcca acggctcctt cccgtgttgt gtcaagccca cggtttgacg     840
cctgcacaag tggtcgccat cgcctccaac ggtggcggta agcaggcgct ggaaacagta     900
cagcgcctgc tgcctgtact gtgccaggat catggactca ccccagacca ggtagtcgca     960
atcgcgtcga atggcgggg aaagcaagcc ctggaaaccg tgcaaaggtt gttgccggtc    1020
ctttgtcaag accacggcct tacaccggag caagtcgtgg ccattgcatc aaatatcggt    1080
ggcaaacagg ctcttgagac ggttcagaga cttctcccag ttctctgtca agcccacggg    1140
ctgactcccg atcaagttgt agcgattgcg agccatgatg gagggaaaca agcattggag    1200
actgtccaac ggctccttcc cgtgttgtgt caagcccacg gtttgacgcc tgcacaagtg    1260
gtcgccatcg cctccaatat tggcggtaag caggcgctgg aaacagtaca gcgcctgctg    1320
cctgtactgt gccaggatca tgggctgacc ccagaccagg tagtcgcaat cgcgtcgcat    1380
gacggggga agcaagccct ggaaaccgtg caaaggttgt tgccggtcct ttgtcaagac    1440
cacgccctta caccggagca agtcgtggcc attgcatcac atgacggtgg caaacaggct    1500
cttgagacgg ttcagagact tctcccagtt ctctgtcaag cccacgggct gactcccgat    1560
caagttgtag cgattgcgag caatgggga gggaaacaag cattggagac tgtccaacgg    1620
ctccttcccg tgttgtgtca agcccacggt ttgacgcctg cacaagtggt cgccatcgcc    1680
aacaacaacg gcggtaagca ggcgctggaa acagtacagc gcctgctgcc tgtactgtgc    1740
caggatcatg gtttgacccc agaccaggta gtcgcaatcg cgtcgcatga cgggggaaag    1800
caagccctgg aaaccgtgca aaggttgttg ccggtccttt gtcaagacca cggccttaca    1860
ccggagcaag tcgtggccat tgcatcaaat atcggtggca aacaggctct tgagacggtt    1920
cagagacttc tcccagttct ctgtcaagcc cacgggctga ctcccgatca agttgtagcg    1980
```

```
attgcgaata caatggagg gaaacaagca ttggagactg tccaacggct ccttcccgtg    2040
ttgtgtcaag cccacggttt gacgcctgca caagtggtcg ccatcgcctc ccacgacggc    2100
ggtaagcagg cgctggaaac agtacagcgc ctgctgcctg tactgtgcca ggatcatggc    2160
ctgacacccg aacaggtggt cgccattgct agcaacgggg gaggacggcc agccttggag    2220
tccatcgtag cccaattgtc caggcccgat cccgcgttgg ctgcgttaac gaatgaccat    2280
ctggtggcgt tggcatgtct tggtggacga cccgcgctcg atgcagtcaa aaagggtctg    2340
cctcatgctc ccgcattgat caaaagaacc aaccggcgga ttcccgagag aacttcccat    2400
cgagtcgcgg gatcccagct ggtgaagagc gagctggagg agaagaagtc cgagctgcgg    2460
cacaagctga agtacgtgcc ccacgagtac atcgagctga tcgagatcgc caggaacagc    2520
acccaggacc gcatcctgga gatgaaggtg atggagttct tcatgaaggt gtacggctac    2580
aggggaaagc acctgggcgg aagcagaaag cctgacggcg ccatctatac agtgggcagc    2640
cccatcgatt acggcgtgat cgtggacaca aaggcctaca gcggcggcta caatctgcct    2700
atcggccagg ccgacgagat gcagagatac gtggaggaga accagacccg gaataagcac    2760 atcaaccca acgagtggtg gaaggtgtac cctagcagcg tgaccgagtt caagttcctg    2820
ttcgtgagcg gccacttcaa gggcaactac aaggcccagc tgaccaggct gaaccacatc    2880
accaactgca atggcgccgt gctgagcgtg gaggagctgc tgatcggcgg cgagatgatc    2940
aaagccggca ccctgacact ggaggaggtg cggcgcaagt tcaacaacgg cgagatcaac    3000
ttcagatctt gataa                                                    3015
```

<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 91
gtcagacgct ggcactcc                                                  18

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 92
gtgtatctgg ccactgatga                                                20

<210> SEQ ID NO 93
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 93
ctgaagggca tcgacttc                                                  18

<210> SEQ ID NO 94
<211> LENGTH: 17
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 94
ctgagcccat ttcctcg                                                        17

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ctcttcagcc ttttgcagtt t                                                   21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
cttcattaca cctgcagctc t                                                   21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
ttcttccaga attgatactg a                                                   21

<210> SEQ ID NO 98
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tcattacacc tgcagc                                                         16

<210> SEQ ID NO 99
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
cttccagaat tgatac                                                         16

<210> SEQ ID NO 100
<211> LENGTH: 35
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 100

Leu Asp Thr Gly Gln Leu Leu Lys Ile Ala Lys Arg His Gly Val
1               5                   10                  15

Thr Ala Val Glu Ala Val His Ala Trp Arg Asn Ala Leu Thr Gly Ala
            20                  25                  30

Pro Leu Asn
        35

<210> SEQ ID NO 101
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Leu Asp Thr Gly Gln Leu Leu Lys Ile Ala Lys Arg Ser Gly Val
1               5                   10                  15

Thr Ala Val Glu Ala Val His Ala Trp Arg Asn Ala Leu Thr Gly Ala
            20                  25                  30

Pro Leu Asn
        35

<210> SEQ ID NO 102
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
tcagacgctg gcact                                                    15

<210> SEQ ID NO 103
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
tctgcttgga cattctat                                                 18

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tctgggctct cccat                                                    15

<210> SEQ ID NO 105
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 105
ttttgcagat atacactt                                                    18

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
tttgtctttg cctcctttt                                                   18

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
tgccgttctt ctgcttgt                                                    18

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tcgagcttcc ccttcatt                                                    18

<210> SEQ ID NO 109
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ttcattgcct gccatgt                                                     17

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ctgaccctgc ctgctcct                                                    18

<210> SEQ ID NO 111
<211> LENGTH: 18
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 111
tgtcctcctc taactgct                                                18

<210> SEQ ID NO 112
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tggcccttgc agccgt                                                  16

<210> SEQ ID NO 113
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ttcctgccca gctccat                                                 17

<210> SEQ ID NO 114
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ttcagtgttg ttctggt                                                 17

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tgctgtagtc agcaatct                                                18

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tcccaatgct gccatcat                                                18

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 117
tccccattct acagcagt                                                        18

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
ttgcaaagat tgctgact                                                        18

<210> SEQ ID NO 119
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tgtgggcaac atgct                                                           15

<210> SEQ ID NO 120
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
tggtcatcct catcct                                                          16

<210> SEQ ID NO 121
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
tgatactgac tgtat                                                           15

<210> SEQ ID NO 122
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ttcccttctg ggcagt                                                          16

<210> SEQ ID NO 123
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ttcatctttg ccaacgt                                                    17

<210> SEQ ID NO 124
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tcacagatat atctgt                                                     16

<210> SEQ ID NO 125
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tgtaagctct cctccat                                                    17

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
ttgggaggtg gtcctgtt                                                   18

<210> SEQ ID NO 127
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
taatgacatc ctgaagct                                                   18

<210> SEQ ID NO 128
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
taacggcaga cttct                                                      15

<210> SEQ ID NO 129
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 129
tggtgcacct gactcct                                                  17

<210> SEQ ID NO 130
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
tgccccacag ggcagt                                                   16

<210> SEQ ID NO 131
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tgccccacag ggcagt                                                   16

<210> SEQ ID NO 132
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
tcccctccac cccacagt                                                 18

<210> SEQ ID NO 133
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
ttttctgtca ccaatcct                                                 18

<210> SEQ ID NO 134
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
tcctggggca caagct                                                   16

<210> SEQ ID NO 135
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
```

```
tatagacgtt gtggct                                                    16

<210> SEQ ID NO 136
<211> LENGTH: 15
<212> TYPE: DNA
<213> ORGANISM: Homo sapiens

<400> SEQUENCE: 136
tacacctgca gctct                                                     15

<210> SEQ ID NO 137
<211> LENGTH: 18
<212> TYPE: DNA
<213> ORGANISM: Homo sapiens

<400> SEQUENCE: 137
tacacctgca gctctcat                                                  18

<210> SEQ ID NO 138
<211> LENGTH: 77
<212> TYPE: DNA
<213> ORGANISM: Homo sapiens

<400> SEQUENCE: 138
aaaaagaagg tcttcattac acctgcagct ctcattttcc atacagtcag tatcaattct    60
ggaagaattt ccagaca                                                   77

<210> SEQ ID NO 139
<211> LENGTH: 18
<212> TYPE: DNA
<213> ORGANISM: Homo sapiens

<400> SEQUENCE: 139
tcttccagaa ttgatact                                                  18

<210> SEQ ID NO 140
<211> LENGTH: 16
<212> TYPE: DNA
<213> ORGANISM: Homo sapiens

<400> SEQUENCE: 140
ttcttccaga attgat                                                    16

<210> SEQ ID NO 141
<211> LENGTH: 18
<212> TYPE: DNA
<213> ORGANISM: Homo sapiens

<400> SEQUENCE: 141
ttcattacac ctgcagct                                                  18

<210> SEQ ID NO 142
<211> LENGTH: 69
<212> TYPE: DNA
<213> ORGANISM: Homo sapiens

<400> SEQUENCE: 142
aaaaagaagg tcttcattac acctgcagct ctcattttcc atacagtcag tatcaattct    60
ggaagaatt                                                            69

<210> SEQ ID NO 143
```

```
<211> LENGTH: 13
<212> TYPE: DNA
<213> ORGANISM: Homo sapiens

<400> SEQUENCE: 143
tgatactgac tgt                                                       13

<210> SEQ ID NO 144
<211> LENGTH: 969
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144
```

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Arg Gly Val Pro Met Val Asp Leu Arg Thr Leu Gly Tyr
            35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Asp Gln Val Val Ala Ile Ala Ser Asn Ile Gly Gly Lys
            180                 185                 190

Gln Ala Leu Glu Thr Val Gln Arg Leu Leu Pro Val Leu Cys Gln Asp
        195                 200                 205

His Gly Leu Thr Pro Glu Gln Val Val Ala Ile Ala Ser His Asp Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Asp Gln Val Val Ala Ile Ala Asn Asn
                245                 250                 255

Asn Gly Gly Lys Gln Ala Leu Glu Thr Val Gln Arg Leu Leu Pro Val
            260                 265                 270

Leu Cys Gln Ala His Gly Leu Thr Pro Ala Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Asp His Gly Leu Thr Pro Asp Gln Val Val Ala
305                 310                 315                 320

-continued

```
Ile Ala Ser His Asp Gly Gly Lys Gln Ala Leu Glu Thr Val Gln Arg
            325                 330                 335

Leu Leu Pro Val Leu Cys Gln Asp His Gly Leu Thr Pro Asp Gln Val
        340                 345                 350

Val Ala Ile Ala Asn Asn Asn Gly Gly Lys Gln Ala Leu Glu Thr Val
    355                 360                 365

Gln Arg Leu Leu Pro Val Leu Cys Gln Ala His Gly Leu Thr Pro Asp
370                 375                 380

Gln Val Val Ala Ile Ala Ser Asn Gly Gly Lys Gln Ala Leu Glu
385                 390                 395                 400

Thr Val Gln Arg Leu Leu Pro Val Leu Cys Gln Ala His Gly Leu Thr
            405                 410                 415

Pro Ala Gln Val Val Ala Ile Ala Asn Asn Asn Gly Gly Lys Gln Ala
        420                 425                 430

Leu Glu Thr Val Gln Arg Leu Leu Pro Val Leu Cys Gln Asp His Gly
    435                 440                 445

Leu Thr Pro Asp Gln Val Val Ala Ile Ala Asn Asn Asn Gly Gly Lys
450                 455                 460

Gln Ala Leu Glu Thr Val Gln Arg Leu Leu Pro Val Leu Cys Gln Asp
465                 470                 475                 480

His Gly Leu Thr Pro Glu Gln Val Val Ala Ile Ala Ser Asn Ile Gly
            485                 490                 495

Gly Lys Gln Ala Leu Glu Thr Val Gln Arg Leu Leu Pro Val Leu Cys
        500                 505                 510

Gln Ala His Gly Leu Thr Pro Ala Gln Val Val Ala Ile Ala Ser Asn
    515                 520                 525

Ile Gly Gly Lys Gln Ala Leu Glu Thr Val Gln Arg Leu Leu Pro Val
530                 535                 540

Leu Cys Gln Asp His Gly Leu Thr Pro Asp Gln Val Val Ala Ile Ala
545                 550                 555                 560

Ser Asn Ile Gly Gly Lys Gln Ala Leu Glu Thr Val Gln Arg Leu Leu
            565                 570                 575

Pro Val Leu Cys Gln Asp His Gly Leu Thr Pro Asp Gln Val Val Ala
        580                 585                 590

Ile Ala Asn Asn Asn Gly Gly Lys Gln Ala Leu Glu Thr Val Gln Arg
    595                 600                 605

Leu Leu Pro Val Phe Cys Gln Ala His Gly Leu Thr Pro Asp Gln Val
610                 615                 620

Val Ala Ile Ala Asn Asn Asn Gly Gly Lys Gln Ala Leu Glu Thr Val
625                 630                 635                 640

Gln Arg Leu Leu Pro Val Leu Cys Gln Ala His Gly Leu Thr Pro Ala
            645                 650                 655

Gln Val Val Ala Ile Ala Ser His Asp Gly Gly Lys Gln Ala Leu Glu
        660                 665                 670

Thr Val Gln Arg Leu Leu Pro Val Leu Cys Gln Asp His Gly Leu Thr
    675                 680                 685

Pro Glu Gln Val Val Ala Ile Ala Ser His Asp Gly Gly Arg Pro Ala
690                 695                 700

Leu Glu Ser Ile Val Ala Gln Leu Ser Arg Pro Asp Pro Ala Leu Ala
705                 710                 715                 720

Ala Leu Thr Asn Asp His Leu Val Ala Leu Ala Cys Leu Gly Gly Arg
            725                 730                 735

Pro Ala Leu Asp Ala Val Lys Lys Gly Leu Pro His Ala Pro Ala Leu
```

```
            740                 745                 750
Ile Lys Arg Thr Asn Arg Arg Ile Pro Glu Arg Thr Ser His Arg Val
            755                 760                 765

Ala Gly Ser Gln Leu Val Lys Ser Glu Leu Glu Glu Lys Lys Ser Glu
        770                 775                 780

Leu Arg His Lys Leu Lys Tyr Val Pro His Glu Tyr Ile Glu Leu Ile
785                 790                 795                 800

Glu Ile Ala Arg Asn Ser Thr Gln Asp Arg Ile Leu Glu Met Lys Val
                805                 810                 815

Met Glu Phe Phe Met Lys Val Tyr Gly Tyr Arg Gly Lys His Leu Gly
            820                 825                 830

Gly Ser Arg Lys Pro Asp Gly Ala Ile Tyr Thr Val Gly Ser Pro Ile
        835                 840                 845

Asp Tyr Gly Val Ile Val Asp Thr Lys Ala Tyr Ser Gly Gly Tyr Asn
850                 855                 860

Leu Pro Ile Gly Gln Ala Asp Glu Met Gln Arg Tyr Val Glu Glu Asn
865                 870                 875                 880

Gln Thr Arg Asn Lys His Ile Asn Pro Asn Glu Trp Trp Lys Val Tyr
                885                 890                 895

Pro Ser Ser Val Thr Glu Phe Lys Phe Leu Phe Val Ser Gly His Phe
            900                 905                 910

Lys Gly Asn Tyr Lys Ala Gln Leu Thr Arg Leu Asn His Ile Thr Asn
        915                 920                 925

Cys Asn Gly Ala Val Leu Ser Val Glu Glu Leu Leu Ile Gly Gly Glu
        930                 935                 940

Met Ile Lys Ala Gly Thr Leu Thr Leu Glu Glu Val Arg Arg Lys Phe
945                 950                 955                 960

Asn Asn Gly Glu Ile Asn Phe Arg Ser
                965

<210> SEQ ID NO 145
<211> LENGTH: 901
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Arg Gly Val Pro Met Val Asp Leu Arg Thr Leu Gly Tyr
            35                  40                  45

Ser Gln Gln Gln Gln Glu Lys Ile Lys Pro Lys Val Arg Ser Thr Val
        50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
                100                 105                 110

Ile Val Gly Val Gly Lys Gln Trp Ser Gly Ala Arg Ala Leu Glu Ala
            115                 120                 125
```

```
Leu Leu Thr Val Ala Gly Glu Leu Arg Gly Pro Pro Leu Gln Leu Asp
    130                 135                 140
Thr Gly Gln Leu Leu Lys Ile Ala Lys Arg Gly Gly Val Thr Ala Val
145                 150                 155                 160
Glu Ala Val His Ala Trp Arg Asn Ala Leu Thr Gly Ala Pro Leu Asn
                    165                 170                 175
Leu Thr Pro Asp Gln Val Val Ala Ile Ala Ser His Asp Gly Gly Lys
                180                 185                 190
Gln Ala Leu Glu Thr Val Gln Arg Leu Leu Pro Val Leu Cys Gln Asp
            195                 200                 205
His Gly Leu Thr Pro Asp Gln Val Val Ala Ile Ala Asn Asn Asn Gly
    210                 215                 220
Gly Lys Gln Ala Leu Glu Thr Val Gln Arg Leu Leu Pro Val Leu Cys
225                 230                 235                 240
Gln Ala His Gly Leu Thr Pro Asp Gln Val Val Ala Ile Ala Asn Asn
                    245                 250                 255
Asn Gly Gly Lys Gln Ala Leu Glu Thr Val Gln Arg Leu Leu Pro Val
                260                 265                 270
Leu Cys Gln Ala His Gly Leu Thr Pro Ala Gln Val Val Ala Ile Ala
            275                 280                 285
Asn Asn Asn Gly Gly Lys Gln Ala Leu Glu Thr Val Gln Arg Leu Leu
    290                 295                 300
Pro Val Leu Cys Gln Asp His Gly Leu Thr Pro Asp Gln Val Val Ala
305                 310                 315                 320
Ile Ala Asn Asn Asn Gly Gly Lys Gln Ala Leu Glu Thr Val Gln Arg
                    325                 330                 335
Leu Leu Pro Val Leu Cys Gln Asp His Gly Leu Thr Pro Glu Gln Val
                340                 345                 350
Val Ala Ile Ala Ser Asn Ile Gly Gly Lys Gln Ala Leu Glu Thr Val
            355                 360                 365
Gln Arg Leu Leu Pro Val Leu Cys Gln Ala His Gly Leu Thr Pro Asp
    370                 375                 380
Gln Val Val Ala Ile Ala Ser Asn Gly Gly Gly Lys Gln Ala Leu Glu
385                 390                 395                 400
Thr Val Gln Arg Leu Leu Pro Val Leu Cys Gln Ala His Gly Leu Thr
                    405                 410                 415
Pro Ala Gln Val Val Ala Ile Ala Asn Asn Asn Gly Gly Lys Gln Ala
                420                 425                 430
Leu Glu Thr Val Gln Arg Leu Leu Pro Val Leu Cys Gln Asp His Gly
            435                 440                 445
Leu Thr Pro Asp Gln Val Val Ala Ile Ala Ser Asn Ile Gly Gly Lys
    450                 455                 460
Gln Ala Leu Glu Thr Val Gln Arg Leu Leu Pro Val Leu Cys Gln Asp
465                 470                 475                 480
His Gly Leu Thr Pro Glu Gln Val Val Ala Ile Ala Ser Asn Gly Gly
                    485                 490                 495
Gly Lys Gln Ala Leu Glu Thr Val Gln Arg Leu Leu Pro Val Leu Cys
                500                 505                 510
Gln Ala His Gly Leu Thr Pro Asp Gln Val Val Ala Ile Ala Ser His
            515                 520                 525
Asp Gly Gly Lys Gln Ala Leu Glu Thr Val Gln Arg Leu Leu Pro Val
    530                 535                 540
Leu Cys Gln Ala His Gly Leu Thr Pro Ala Gln Val Val Ala Ile Ala
```

|     |     |     |     | 545 |     |     |     |     | 550 |     |     |     |     | 555 |     |     |     |     | 560 |
| --- | --- | --- | --- | --- | --- | --- | --- | --- | --- | --- | --- | --- | --- | --- | --- | --- | --- | --- | --- |

Ser Asn Gly Gly Gly Lys Gln Ala Leu Glu Thr Val Gln Arg Leu Leu
                565                  570                  575

Pro Val Leu Cys Gln Asp His Gly Leu Thr Pro Asp Gln Val Val Ala
        580                  585                  590

Ile Ala Ser Asn Ile Gly Gly Lys Gln Ala Leu Glu Thr Val Gln Arg
           595                  600                605

Leu Leu Pro Val Leu Cys Gln Asp His Gly Leu Thr Pro Glu Gln Val
        610                  615                  620

Val Ala Ile Ala Ser His Asp Gly Gly Arg Pro Ala Leu Glu Ser Ile
625                630                  635                640

Val Ala Gln Leu Ser Arg Pro Asp Pro Ala Leu Ala Ala Leu Thr Asn
                645                  650                655

Asp His Leu Val Ala Leu Ala Cys Leu Gly Gly Arg Pro Ala Leu Asp
        660                  665                  670

Ala Val Lys Lys Gly Leu Pro His Ala Pro Ala Leu Ile Lys Arg Thr
           675                  680                685

Asn Arg Arg Ile Pro Glu Arg Thr Ser His Arg Val Ala Gly Ser Gln
690                695                  700

Leu Val Lys Ser Glu Leu Glu Glu Lys Lys Ser Glu Leu Arg His Lys
705                710                  715                720

Leu Lys Tyr Val Pro His Glu Tyr Ile Glu Leu Ile Glu Ile Ala Arg
           725                  730                735

Asn Ser Thr Gln Asp Arg Ile Leu Glu Met Lys Val Met Glu Phe Phe
        740                  745                  750

Met Lys Val Tyr Gly Tyr Arg Gly Lys His Leu Gly Gly Ser Arg Lys
           755                  760                765

Pro Asp Gly Ala Ile Tyr Thr Val Gly Ser Pro Ile Asp Tyr Gly Val
        770                  775                  780

Ile Val Asp Thr Lys Ala Tyr Ser Gly Gly Tyr Asn Leu Pro Ile Gly
785                790                  795                800

Gln Ala Asp Glu Met Gln Arg Tyr Val Glu Glu Asn Gln Thr Arg Asn
                805                  810                815

Lys His Ile Asn Pro Asn Glu Trp Trp Lys Val Tyr Pro Ser Ser Val
        820                  825                  830

Thr Glu Phe Lys Phe Leu Phe Val Ser Gly His Phe Lys Gly Asn Tyr
           835                  840                845

Lys Ala Gln Leu Thr Arg Leu Asn His Ile Thr Asn Cys Asn Gly Ala
        850                  855                  860

Val Leu Ser Val Glu Glu Leu Leu Ile Gly Gly Glu Met Ile Lys Ala
865                870                  875                880

Gly Thr Leu Thr Leu Glu Glu Val Arg Arg Lys Phe Asn Asn Gly Glu
                885                  890                895

Ile Asn Phe Arg Ser
        900

<210> SEQ ID NO 146
<211> LENGTH: 10
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 146
ttcatatcct                                                                10

<210> SEQ ID NO 147
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ttgaccagct                                                                10

<210> SEQ ID NO 148
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
aaagaaggtc ttcattacac ctgcagctct cattttccat acagtcagta tcaattctgg         60
aagaatttcc agacattaaa                                                     80

<210> SEQ ID NO 149
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
aaagaaggtc ttcattacac ctgcagctct cattttccat acagtatcaa ttctggaaga         60
atttccagac attaaa                                                         76

<210> SEQ ID NO 150
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
aaagaaggtc ttcattacac ctgcagctct cattttccat acagagtatc aattctggaa         60
gaatttccag acattaaa                                                       78

<210> SEQ ID NO 151
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
aaagaaggtc ttcattacac ctgcagctct cattttccat agtatcaatt ctggaagaat         60
ttccagacat taaa                                                           74

<210> SEQ ID NO 152
<211> LENGTH: 69
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 152
aaagaaggtc ttcattacac ctgcagctct cattttccat caattctgga agaatttcca    60
gacattaaa                                                            69

<210> SEQ ID NO 153
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
aaagaaggtc ttcattacac ctgcagctct cattttccat actcagtatc aattctggaa    60
gaatttccag acattaaa                                                  78

<210> SEQ ID NO 154
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
aaagaaggtc ttcattacac ctgcagctct cattttccat acaagtatca attctggaag    60
aatttccaga cattaaa                                                   77

<210> SEQ ID NO 155
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
aaagaaggtc ttcattacac ctgcagctct cattttccat cagtatcaat tctggaagaa    60
tttccagaca ttaaa                                                     75

<210> SEQ ID NO 156
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
aaagaaggtc ttcattacac ctgcagctct cattttccat aagtatcaat tctggaagaa    60
tttccagaca ttaaa                                                     75

<210> SEQ ID NO 157
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 157
aaagaaggtc ttcattacac ctgcagctct cattccatac agtcagtatc aattctggaa    60
gaatttccag acattaaa    78

<210> SEQ ID NO 158
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
aaagaaggtc ttcattacac ctgcagctct catcaattct ggaagaattt ccagacatta    60
aa    62

<210> SEQ ID NO 159
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
aaagaaggtc ttcattacac ctgcagctct cattttccat atcagtatca attctggaag    60
aatttccaga cattaaa    77

<210> SEQ ID NO 160
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
aaagaaggtc ttcattacac ctgcagctct cattttccat acaggtatca attctggaag    60
aatttccaga cattaaa    77

<210> SEQ ID NO 161
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
aaagaaggtc ttcattacac ctgcagctct cattttccat aatcaattct ggaagaattt    60
ccagacatta aa    72

<210> SEQ ID NO 162
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
aaagaaggtc ttcattacac ctgcagctct cattttccat tcagtatcaa ttctggaaga    60

-continued atttccagac attaaa                                                    76

<210> SEQ ID NO 163
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
aaagaaggtc ttcattacac ctgcagctct cattttccat acagtcaatt ctggaagaat    60
ttccagacat taaa                                                      74

<210> SEQ ID NO 164
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
aaagaaggtc ttcattacac ctgcagctct cattttccat aatttccaga cattaaa       57

<210> SEQ ID NO 165
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
aaagaaggtc ttcattacac ctgcagctct cattttccat agtcagtatc aattctggaa    60
gaatttccag acattaaa                                                  78

<210> SEQ ID NO 166
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
aaagaaggtc ttcattacac ctgcagctct cattttccat gtcagtatca attctggaag    60
aatttccaga cattaaa                                                   77

<210> SEQ ID NO 167
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
aaagaaggtc ttcattacac ctgcagctct cattttccat aaacagtatc aattctggaa    60
gaatttccat taaa                                                      74

<210> SEQ ID NO 168
<211> LENGTH: 73

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
aaagaaggtc ttcattacac ctgcagctct cattttccat atatcaattc tggaagaatt     60
tccagacatt aaa                                                        73

<210> SEQ ID NO 169
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
aaagaaggtc ttcattacac ctgcagctct cattttccag tcagtatcaa ttctggaaga     60
atttccagac attaaa                                                     76

<210> SEQ ID NO 170
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
aaagaaggtc ttcattacac ctgcagctct cattttccat acgtatcaat tctggaagaa     60
tttccagaca ttaaa                                                      75
```

MODIFIED DNA-BINDING PROTEINS AND USES THEREOF

CROSS-REFERENCE TO RELATED APPLICATIONS

The present application claims the benefit of U.S. Provisional Application Nos. 61/560,630, filed Nov. 16, 2011 and 61/694,710, filed Aug. 29, 2011, the disclosures of which are hereby incorporated by reference in their entireties.

FIELD OF THE INVENTION

The present invention provides methods and compositions for increasing the activity and/or specificity of novel DNA binding proteins useful in genetic modifications and regulation of expression status of endogenous genes and other genomic loci.

BACKGROUND OF THE INVENTION

Transcription Activator Effector-like proteins (TALEs) are proteins that are encoded by phytopathogenic bacteria of the genus *Xanthomonas* and *Ralstonia* to influence the gene expression of host plant cells during bacterial infection. These proteins comprise a DNA binding region and an N-terminal domain that appears to interact with the bacterial transport machinery for introducing the protein into the plant cell. The C-terminal domain of the TALE protein seems to interact with the plant host's transcriptional machinery to induce expression of sets of plant genes that are beneficial to the invading bacteria. The DNA binding portion of the proteins is found in the middle section of the protein and is made of an array of repeat units, each approximately 33-35 amino acids in length, which have been shown to be responsible for interacting with the target DNA.

TALE proteins have been under investigation for several years. The bacteria that harbor such proteins are important pathogens for many important crop species and thus the scientific field has sought to understand the mechanisms these bacteria utilize during a successful plant infection. See, e.g., Zhu et al (1998) *MPMI* 11(8):824-832), Yang et al (2000) *J. Biol. Chem.* 275(27):20734-41; Boch et al (see *Science*, (2009) 326 p. 1509) and Moscou and Bogdanove (*Science*, (2009) 326, p. 1501)

TALE proteins have now been utilized to make fusion proteins with a nuclease catalytic domain to allow engineering of target specific nucleases (termed TALE-nucleases or TALENs). Activity of the proteins within the fusion has been increased by truncation of the C-terminal domain of the TALE (see co-owned U.S. Patent Publication 20110301073 as well as Miller et al. (2010) *Nature Biotechnology* 29(8): 731-734 and WO2010079430). Additionally, the TALE DNA binding domains have been fused to transcription activation and repression domains, and these TALE transcription factors (TALE TFs) have been demonstrated to be capable of regulating the expression of an endogenous target gene. Thus, since the DNA binding domains of these proteins can be engineered to recognize a specific sequence and can be fused to a nuclease domain or transcriptional domain, these engineered proteins hold a great deal of interest and promise for genome editing.

A major area of interest in genome biology, especially in light of the determination of the complete nucleotide sequences of a number of genomes, is the targeted alteration of genome sequences by genome editing. Such targeted cleavage events can be used, for example, to induce targeted mutagenesis, induce targeted deletions of cellular DNA sequences, and facilitate targeted recombination at a predetermined chromosomal locus. See, for example, United States Patent Publications 20030232410; 20050208489; 20050026157; 20050064474; 20060188987; 2008015996, and International Publication WO 2007/014275, the disclosures of which are incorporated by reference in their entireties for all purposes. See, also, Santiago et al. (2008) *Prot Natl Acad Sci USA* 105:5809-5814; Perez et al. (2008) *Nat Biotechnol* 26:808-816 (2008).

There remains a need for engineered DNA binding domains comprising TALEs with increased activity and/or specificity. Enhancements in activity and/or specificity of these proteins will increase their scope and usefulness for a variety of applications including engineered transcription factors for regulation of endogenous genes in a variety of cell types, and engineered nucleases that can be similarly used in numerous models, diagnostic and therapeutic systems, and all manner of genome engineering and editing applications.

SUMMARY OF THE INVENTION

The present invention provides for methods and compositions for designing TALE fusion proteins with enhanced activity and specificity. In some aspects, the polypeptide includes the at least one TALE repeat unit linked to additional TALE protein sequences, for efficient and specific function at endogenous target DNA. These additional sequences, which are linked to the N- and optionally the C-termini of the TALE repeat domain, are also referred to as the "N-cap" and "C-cap" sequences. Thus, the invention provides polypeptides comprising one or more (e.g., 1, 2, 3, 4, 5, 6, 7, 8, 9, 10, 11, 12, 13, 14, 15, 20 or more) TALE repeat and/or half-repeat units wherein these polypeptides demonstrate increased activity and increased specificity of binding in comparison with standard TALE proteins.

Thus, in one aspect, provided herein is a TALE DNA-binding polypeptide comprising at least one TALE repeat unit (e.g., 1, 2, 3, 4, 5, 6, 7, 8, 9, 10, 11, 12, 13, 14, 15, 16, 17, 18, 19, 20 or more repeat unit(s)). Each repeat unit includes a repeat variable di-residue (RVD") involved in binding DNA at positions 12 and 13 of the repeat unit. In certain embodiments, the TALE DNA-binding polypeptides described herein comprise 2 or more (e.g., 2, 3, 4, 5, 6, 7 or more) non-canonical RVDs. In other embodiments, the TALE DNA-binding polypeptides comprise 6 distinct (different canonical, non-canonical and/or atypical diresidue sequences) of which 3 or more (1, 2, 3, 4, 5, 6, 7, 8 or more) may be non-canonical or atypical. In other embodiments, the TALE DNA-binding polypeptide comprises a plurality of TALE-repeat units, each TALE-repeat unit comprising a repeat variable di-residue (RVD), wherein at least 2 (e.g., 2, 3, 4, 5, 6, 7, 8) of the TALE repeat units comprise at least 2 distinct non-canonical RVDs. The TALE DNA-binding proteins as described herein can further exhibits enhanced specificity or activity as compared to a TALE DNA binding protein comprising only canonical RVDs. The TALE DNA-binding polypeptide typically includes an N-cap sequence (polypeptide) of any length that supports DNA-binding function of the TALE repeat(s) or functional activity of the TALE fusion protein. Optionally, the polypeptide may also include a C-cap sequence (polypeptide), for example a C-cap sequence of less than approximately 250 amino acids (C+230 C-cap; from residue C-20 to residue C+230). The TALE repeat unit may be a wild-type domain isolated from *Xanthomonas, Ralstonia* or another related bacteria and/or may be engineered in some manner (e.g., altered to be non-canonical and/or atypical). In certain embodiments, at least one TALE repeat unit is engineered (e.g., non-naturally occurring, atypical, codon optimized, combinations thereof, etc.). In certain aspects, the TALE repeat is engineered to increase its binding of a target nucleotide. In other aspects, the TALE repeat is part of a set of TALE repeats that have all been characterized to increase the binding to target for all TALE repeats in the set. In some embodiments, the TALE repeats at the beginning of the DNA binding domain (e.g., R-1, R0 and R1) are engineered to alter their binding activity. In some instances, just the R-1 repeat is engineered for alteration of binding activity. In other instances, the R0 repeat is engineered for alteration of binding activity, and in yet further instances, the R1 repeat is engineered for binding activity alteration. In some embodiments, the TALE protein comprises combinations of two or three of the R-1, R0 or R1 repeats engineered for binding activity alteration. In other embodiments, the half repeat, or R1/2, at the C-terminal end of the DNA binding domain is engineered to alter its binding activity. In some aspects, the TALE repeat is engineered to increase its binding specificity to a target nucleotide. In other aspects, the TALE repeat is part of a set of TALE repeats that have all been engineered to increase the specificity for all TALE repeats in the DNA binding domain. In some embodiments, the TALE repeats at the beginning of the DNA binding domain (R-1, R0 and R1) are engineered to alter their specificity. In some instances, just the R-1 repeat is engineered for alteration of specificity. In other instances, the R0 repeat is engineered for alteration of specificity, and in yet further instances, the R1 repeat is engineered for specificity alteration. In some embodiments, the TALE protein comprises combinations of two or three of the R-1, R0 or R1 repeats engineered for specificity alteration. In other embodiments, the half repeat, or R1/2, at the C-terminal end of the DNA binding domain is engineered to alter its specificity. Preferred non-canonical or atypical (also referred to as engineered) RVDs include the following: for recognition of an adenine (A) in the target DNA site, repeat units with RVDs comprising HI, CI, RI, KI, SI, AI, QI, YI, GI, VI, TI, DI, EI, or FI at positions 12 and 13 may be used. For recognition of a cytosine (C) in the target DNA site, repeat units with ND, AD, KD, RD, SD, CD, ID, or ED at positions 12 and 13 may be used. For recognition of a guanine (G) in the target DNA site, repeat units with RVDs comprising KN, EN, HN, SN, AN, CN, GN, FN, AK, CK, RH, KK, DH, WN, LN, VN, IN, NK, TN, DN, QN, RN, YN, QK, or HH may be used. For recognition of a thymine (T) in the target DNA, repeat units with HG, KG, MG, QG, RG, AA, QA, VA, CG, GG, AG, SG, VG, TG, SA or CP YG, YA, YP, WG, IG, or IS RVDs may be used.

In another embodiment, the invention provides TALENs comprising one or more repeat units in the DNA binding domain where the amino acid at position 11 in the repeat has been altered to increase cleavage activity and/or specificity of the TALEN. In some aspects, the amino acid alteration at position 11 is selected from the group of Alanine (A), Cysteine (C), Glycine (G), Histidine (H), Lysine (K), Methionine (M), Asparagine (N), Glutamine (Q), or Arginine (R). In some instances the alterations of the amino acid at position 11 acts to increase DNA binding or target specificity or a combination thereof.

In some embodiments, TALE proteins comprising several modified (engineered) TALE repeat units are provided. Combinations of naturally occurring and non-naturally occurring TALE repeat units are also provided. Additionally, combinations of naturally occurring, non-naturally occurring and TALE repeats with enhanced activity or specificity are provided. In a preferred embodiment, the TALE protein (wild-type or engineered) further comprises N-cap and optionally the C-cap sequences for efficient and specific function at endogenous target DNA. In some embodiments, the N-cap comprises residues N+1 to N+136, or any fragment thereof (see co-owned U.S. Patent Publication 20110301073 for a description of the numbering system). In other embodiments, the C-cap comprises residues C-20 to C+28, C-20 to C+39, C-20 to C+55, or C-20 to C+63 or any fragments of the full length TALE C-terminus thereof. In certain embodiments, the polypeptide comprising the TALE repeat domain, as well as an N-cap and optional C-cap sequences, further comprises a regulatory or functional domain, for example, a transcriptional activator, transcriptional repressor, nuclease, recombinase, transposase, integrase, methylase or the like.

In one aspect, provided herein are fusion proteins comprising one or more engineered TALE repeat units, engineered TALE repeats units with enhanced activity or specificity, an N-cap, and an optional C-cap sequence, operatively linked to one or more heterologous polypeptide domains, for example functional (regulatory) domains Libraries comprising modules of TALE repeats are provided as are optional structured or flexible linkers for connecting the engineered TALE repeats to the functional protein domain of interest. The functional protein domain (e.g., transcriptional activator, repressor, or nuclease) may be positioned at the C- or N-termini of the fusion protein. Methods of making fusion proteins as described herein are also provided.

Polynucleotides (e.g., DNA, RNA such as mRNA) encoding the proteins described herein are also provided, as are pharmaceutical compositions comprising the proteins and/or polynucleotides. In addition, the invention includes host cells, cell lines and transgenic organisms (e.g., plants, fungi, animals) comprising these proteins/polynucleotides and/or modified by these proteins (e.g., genomic modification that is passed onto the progeny). Exemplary cells and cell lines include animal cells (e.g., mammalian, including human, cells such as stem cells), plant cells, bacterial cells, protozoan cells, fish cells, or fungal cells. In another embodiment, the cell is a mammalian cell. Methods of making and using these proteins and/or polynucleotides are also provided.

The present invention also provides a method for enhancing entire TALE DNA binding domains for increased activity and/or specificity. In some embodiments, multimers of enhanced repeat units are utilized as a module where the module shows enhanced activity and/or specificity when the individual repeat units are linked together relative activity and/or specificity that might be expected based on their average individual properties. Multimers include 3 or more repeat units, for example 3 to 10 repeat units, more preferably 3, 4, 5 or 6 repeat units (e.g., trimers, tetramers, pentamers or hexamers). In other embodiments, several enhanced multimer modules are combined together such that the combination of these enhanced multimers provides a TALE protein with enhanced activity or specificity in comparison with the activity or specificity that might be expected based on their average individual properties. Additionally provided in this invention are novel (non-naturally occurring) sets of repeat units, differing from those found in nature, which are capable of recognizing nucleotide bases where these novel sets of repeat units display enhanced activity in comparison with the naturally occurring repeat units.

Also provided by the invention are methods and compositions to increase TALE-nuclease activity by deleting regions of the nuclease domain (e.g., FokI) of the TALEN. In certain embodiments, amino acids extending approximately 383 through 454, and subsets thereof, are deleted, where the numbering is relative to that of the native FokI protein. The invention also provides compositions and methods for altering the FokI sequence from approximately amino acids 373 to 383, numbered relative to the native FoId protein. The deletions result in a more active FokI nuclease domain and/or more specific TALENs to cleave DNA at the intended site as compared to a FokI domain without the deletions.

Also provided by the invention are methods for single-stranded cleavage (nicking) of a target sequence (e.g., double-stranded DNA such as genomic DNA). The invention provides TALEN proteins where the dimer comprises one partner with a TALE DNA binding domain linked to an active FokI catalytic domain, and a second partner with a TALE DNA binding domain linked to an inactive FokI catalytic domain such that when dimerization occurs, only one strand of the DNA backbone target is cleaved.

In another aspect, the invention provides a method for cleaving a target DNA with increased specificity through the use of two TALEN pairs, each pair capable of nicking a double stranded DNA molecule such that when the two introduced nicks (one by each TALEN pair) are on complementary strands of the DNA and are located sufficiently close to each other to the targeted DNA is separated (cleaved) into two fragments.

In another aspect, the present invention provides a vector for an engineered TALE DNA binding domain fusion wherein the vector comprises the TALE N-cap and C-cap sequences flanking the TALE repeat sequences as well as locations to allow for the cloning of multiple TALE repeat units, linker sequences, promoters, selectable markers, polyadenylation signal sites, functional protein domains and the like.

In yet another aspect, the invention provides compositions (linkers) for linking a nuclease domain to a TALE repeat domain as described herein, wherein the resulting fusion protein exhibits enhanced nuclease function. In some embodiments the linker sequence comprises sequence from native TALE C-terminal flanking sequence. In other embodiments, the linker sequence is derived from a sequence of amino acids known to exhibit a certain exemplary three dimensional structure. In some instances, the exemplary three dimensional structure is an alpha helix, while in other instances, the exemplary structure is a beta sheet, or a beta bend.

In any of the compositions or methods described herein, the enhanced TALE fusion protein may be encoded by a polynucleotide. In certain embodiments, the sequence encoding the TALE fusion protein is operably linked to a promoter. The TALE-fusion protein may be expressed from an expression vector such as a retroviral expression vector, an adenoviral expression vector, a DNA plasmid expression vector, or an AAV expression vector. In some embodiments, the expression vector is a lentiviral vector, and in some of these embodiments, the lentiviral vector is integrase-defective.

Also provided in the invention are enhanced TALENs (e.g., enhanced TALEN pairs) specific to any desired target locus (e.g., endogenous gene) in any cell type. Non-limiting examples include TALENs specific for NTF3, VEGF, CCR5, IL2Rγ, BAX, BAK, FUT8, GR, DHFR, CXCR4, GS, Rosa26, AAVS1 (PPP1R12C), MHC genes, PITX3, ben-1, Pou5F1 (OCT4), C1, RPD1, Factor VII, Factor VIII, Factor IX, Factor X, Factor XI, Factor XII, Bcl11A, albumin, HBB, HBD, HIV, CHO LDHA, Pitx3, rat IgM, rat PMP22, pig BMyHC, TRAC, TRBC, VCP, HPRT, LRRK2, PD1, Htt, TCR genes, CFTR etc.

In another aspect, described herein is a method for cleaving one or more genes of interest in a cell, the method comprising: (a) introducing, into the cell, one or more one or more TALEN protein(s) as described herein (or polynucleotides encoding the TALENs) that bind to a target site in the one or more genes under conditions such that the TALEN protein(s) is (are) expressed and the one or more genes are cleaved. In embodiments in which two or more TALEN proteins are introduced, one, some or all can be introduced as polynucleotides or as polypeptides. In some aspects, said gene cleavage results in the functional disruption of the targeted gene. Cleavage of the targeted DNA may be followed by NHEJ wherein small insertions or deletions (indels) are inserted at the site of cleavage. These indels then cause functional disruption through introduction of non-specific mutations at the cleavage location.

In yet another aspect, described herein is a method for introducing an exogenous sequence into the genome of a cell, the method comprising the steps of: (a) introducing, into the cell, one or more TALEN protein(s) as described herein (or polynucleotides encoding the TALEN protein(s)) that bind to a target site in a target gene under conditions such that the TALEN protein(s) is (are) expressed and the one or more target sites within the genes are cleaved; and (b) contacting the cell with an exogenous sequence; such that cleavage of the DNA target site(s) stimulates integration of the exogenous sequence into the genome by homologous recombination. In certain embodiments, the exogenous sequence is integrated physically into the genome. In other embodiments, the exogenous sequence is integrated into the genome by copying of the exogenous sequence into the host cell genome via specialized nucleic acid replication processes associated with homology-directed repair (HDR) of the double strand break. In yet other embodiments, integration into the genome occurs through non-homology dependent targeted integration (e.g. "end-capture"). In some embodiments, the exogenous sequence comprises a recombinase recognition site (e.g. loxP or FLP) for recognition by a cognate recombinase (e.g. Cre or FRT, respectively). In certain embodiments, the exogenous sequence is integrated into the genome of a small animal (e.g. rabbit or rodent such as mouse, rat, etc.). In one embodiment, the TALE-fusion protein comprises a transposase, recombinase or integrase, wherein the TALE-repeat domain has been engineered to recognize a specifically desired target sequence. In some embodiments, TALE polypeptides are used. In some aspects, the TALE-fusion protein comprises a transposase or integrase and is used for the development of a CHO-cell specific transposase/integrase system.

In some embodiments, the TALE-fusion protein comprises a methyltransferase wherein the TALE-repeat domain has been engineered to recognize a specifically desired target sequence where the specificity of recognition is greater than a TALE repeat domain made from standard TALE repeats.

In another aspect, described herein are compositions comprising one or more of the TALE-fusion proteins and/or polynucleotides described herein. In certain embodiments, the composition comprises one or more TALE-fusion proteins in combination with a pharmaceutically acceptable excipient. In some embodiments, the composition comprises a polynucleotide (e.g., DNA and/or RNA) encoding the TALE fusion protein and a pharmaceutically acceptable excipient. In certain embodiments, the compositions further comprise a nucleic acid donor molecule.

In another aspect, described herein is a TALE-fusion protein expression vector comprising a polynucleotide, encoding one or more enhanced TALE-fusion proteins described herein, operably linked to a promoter (e.g., constitutive, inducible, tissue-specific or the like).

In another aspect, described herein is a host cell comprising one or more enhanced TALE-fusion proteins and/or one or more polynucleotides (e.g., expression vectors encoding TALE-fusion proteins as described herein. In certain embodiments, the host cell further comprises one or more zinc finger proteins and/or ZFP encoding vectors. The host cell may be stably transformed or transiently transfected or a combination thereof with one or more of these protein expression vectors. In other embodiments, the one or more protein expression vectors express one or fusion proteins in the host cell. In another embodiment, the host cell may further comprise an exogenous polynucleotide donor sequence. Any prokaryotic or eukaryotic host cells can be employed, including, but not limited to, bacterial, plant, fish, yeast, algae, insect, worm or mammalian cells. In some embodiments, the host cell is a plant cell. In other aspects, the host cell is part of a plant tissue such as the vegetative parts of the plant, storage organs, fruit, flower and/or seed tissues. In further embodiments, the host cell is an algae cell. In other embodiments, the host cell is a fibroblast. In any of the embodiments, described herein, the host cell may comprise a stem cell, for example an embryonic stem cell. The stem cell may be a mammalian stem cell, for example, a hematopoietic stem cell, a mesenchymal stem cell, an embryonic stem cell, a neuronal stem cell, a muscle stem cell, a liver stem cell, a skin stem cell, an induced pluripotent stem cell and/or combinations thereof. In certain embodiments, the stem cell is a human induced pluripotent stem cells (hiPSC) or a human embryonic stem cell (hESC). In any of the embodiments, described herein, the host cell can comprise an embryo cell, for example one or more mouse, rat, rabbit or other mammal cell embryos.

In some aspects, stem cells or embryo cells are used in the development of transgenic animals, including for example animals with TALE-mediated genomic modifications that are integrated into the germline such that the mutations are heritable. In further aspects, these transgenic animals are used for research purposes, i.e. mice, rats, rabbits; while in other aspects, the transgenic animals are livestock animals, i.e. cows, chickens, pigs, sheep etc. In still further aspects, the transgenic animals are those used for therapeutic purposes, i.e. goats, cows, chickens, pigs; and in other aspects, the transgenic animals are companion animals, i.e. cats, dogs, horses, birds or fish.

Another aspect provided by the invention is a method for identifying a suitable nucleic acid target for TALE binding. In some embodiments, a target is selected that is not utilized by typical, naturally-occurring TALE proteins because the TALE proteins as described herein have been altered in such a way as to make them able to interact with an atypical target sequence. In some embodiments, this alteration involves the selection of atypical (non-naturally occurring or rare) RVD sequences. In further embodiments, the atypical RVD used are incorporated in the R-1, R0 or R1 repeat units, or in combinations thereof.

In one aspect, the invention provides compositions and methods for in vivo genomic manipulation. In certain embodiments, mRNAs encoding TALENs may be injected into gonads, ovum or embryos for introducing specific DSBs as desired. In some embodiments, donor nucleotides are co-delivered with the TALEN mRNAs to cause specific targeted integration in the organism.

In yet a further aspect, provided herein are kits comprising the enhanced TALE-domain proteins (and fusion proteins comprising these TALE-repeat proteins) of the invention. These kits may be used to facilitate genomic manipulation by the user and so can provide a TALEN, for example, that will cleave a desired target or a safe harbor locus within a genome. The TALEN may be provided either as nucleic acid (e.g. DNA or RNA) or may be provided as protein. In some instances, the protein may be formulated to increase stability, or may be provided in a dried form. In some instances, the kits are used for diagnostic purposes. In some instances, the TALE-fusion included in the kit is a transcriptional regulator. In some instances, the TALE-fusion comprises a reporter.

BRIEF DESCRIPTION OF THE DRAWINGS

FIG. 3 shows examples of variance of 'NN' and 'NG' RVDs as determined by SELEX analysis of four TALEN proteins. The plots on the left side of the figure (SBS 101082, target site shown in SEQ ID NO:92 and 101089, target site shown in SEQ ID NO:93) show the variability of base specificity for NN when adjoined by either HD or NI, and the plots on the right (SBS101051, target site shown in SEQ ID NO:94 and 101034, target site shown in SEQ ID NO:95) indicate the variability for NG when used between two neighboring NG RVDs.

FIG. 4, panels A and B, are illustrations of the design strategy used for the multimer (tetramer) shotgun experiment described in Example 1. FIG. 4A discloses SEQ ID NOS 98, 141, 138, 139, and 99, respectively, in order of appearance.

FIG. 5 discloses SEQ ID NOS: 141, 146, 147, 146, 147, and 141, respectively, in order of appearance.

FIG. 6, panels A to H, show gels showing the results of the Cel I assay for all the various conditions 1 through 4 (c1 through c4, as shown to the left of each gel) as described in Example 1. Lane identities are shown in Tables 4 through 7.

FIG. 10, panels A and B, show SELEX analysis of TALENs and demonstrates the variability of the HD or NG RVDs when located at the R1 position of the TALE DNA binding domain in comparison with HD at other positions in the domain. FIG. 10B shows the results for SBS101133 (target site shown in SEQ ID NO:109), SBS101049 (target site shown in SEQ ID NO:111), SBS101138 (target site shown in SEQ ID NO:110) and SBS101084 (target site shown in SEQ ID NO:112).

FIG. 12 depicts the sequences (SEQ ID NOs: 148 to 170 from top to bottom) obtained by deep sequencing of products following cleavage using BfiI-TALENs. Deletions are designated by (:). "#" indicates the number of times this event was detected.

DETAILED DESCRIPTION OF THE INVENTION

Introduction

Figure 1:
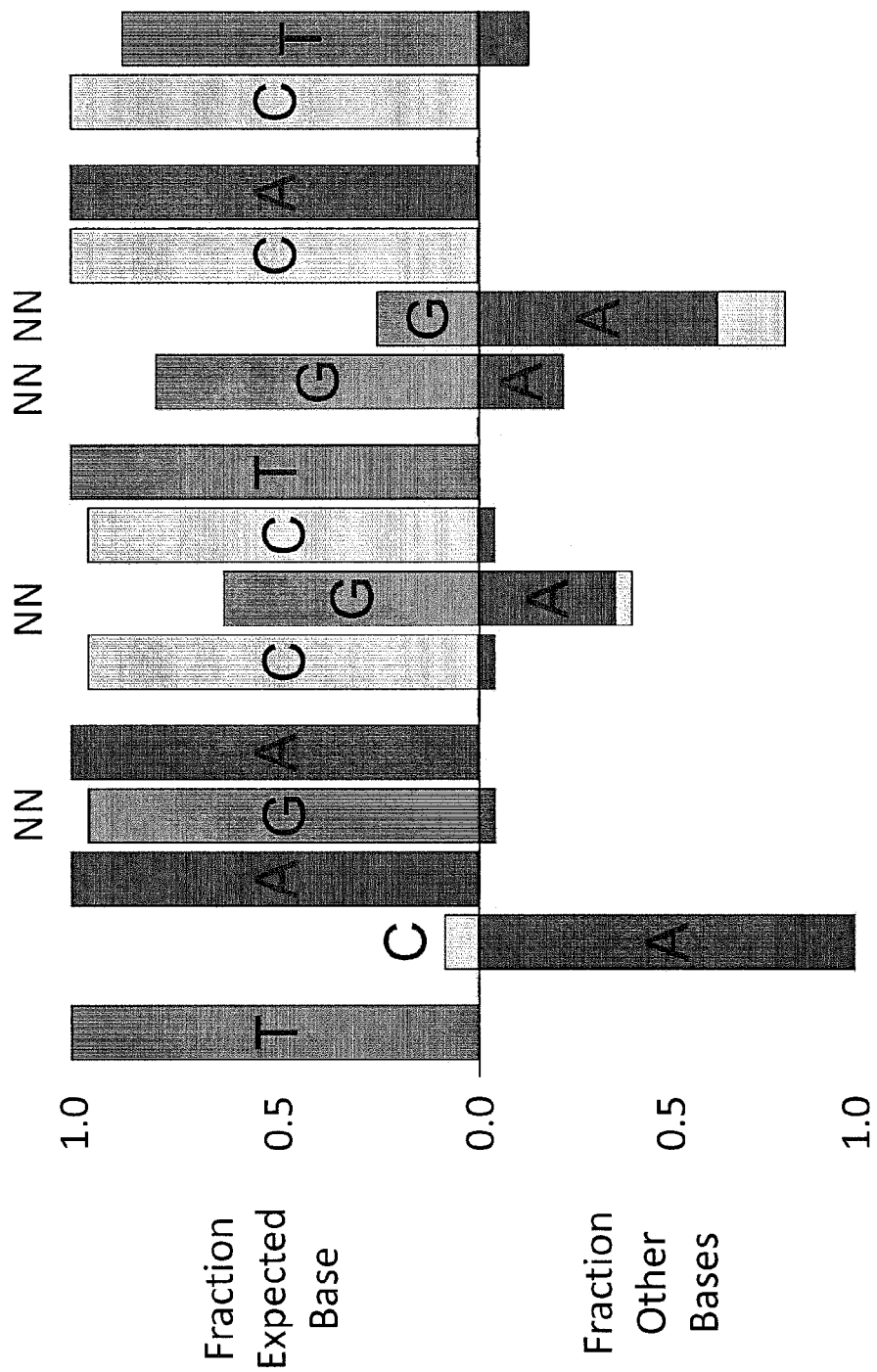
FIG. 1 depicts the results of a SELEX analysis of TALEN SBS101146 (target site shown in SEQ ID NO:91) where the DNA binding protein is probed with a library of potential targets, and the DNA fragments that bound are identified by sequence analysis. The bases 'expected' to bind to the TALEN according to the canonical code are indicated above the 0.0 line, and the bases that were detected that were not expected are indicated below the 0.0 line. The size of the bar or bar segment is proportional to the percent of that base detected.

The present application describes TALE DNA-binding polypeptides, fusion proteins comprising these TALE DNA-binding polypeptides and methods of using these fusion proteins, including enhancing one or more of the functions (e.g., DNA binding activity, nuclease cleavage activity and/ or DNA binding specificity) of these proteins. Thus, the invention provides TALE fusion proteins that are bind with increased specificity to a target site, and bind to only that target site in a genome with any significance. These proteins, when fused to a nuclease cleavage domain, exhibit increased cleavage activity in comparison with TALE fusion proteins made from wild-type TALE DNA binding domains (including wild-type repeat units organized in non-naturally occurring combinations) and wild type nuclease domains.

In some embodiments, the invention comprises methods for increasing the activity of TALE-) fusion proteins, for example TALE-nuclease fusion proteins (TALENs). Methods to increase TALE activity contemplated by this invention include alteration (optimization) of specific regions of the TALE structure such as the R-1, R0, and R1 repeat units on the N-terminal region of the DNA binding repeat array and/or alteration (optimization) of the R1/2 repeat on the C-terminal region of the repeat array. Cleavage activity is enhanced by identification and use of specific TALE RVDs that are differentially sensitive to methylation in the target DNA. TALE activity is also increased by the identification and optimization of context dependent rules for DNA recognition by TALE proteins and use of these rules in protein design. In some embodiments, TALE activity is increased by altering the amino acid at position 11 as compared to the wild-type residue, namely by selecting an atypical (non-wild-type) amino acid for position 11 in a repeat unit. In other embodiments, these methods and compositions are used to increase TALE activity in TALE-TF fusion proteins.

Specificity of TALEs interaction with their target can also be enhanced by the methods and compositions of the invention, including by use of a linker between the TALE portion of a TALEN fusion protein and the nuclease domain may that increases the stringency of interaction between the fusion protein and its intended DNA target. Current TALE fusions are able to act on sequences with a varied number of nucleotides in the gap between the target sites for each half of the TALEN pair. Thus, when the gap spacing between the two nuclease halves is restricted to a very controlled distance (spacing) via the linker, specificity is increased. In some embodiments, optimal linkers are used which influence the ordered protein structure in this region and give the protein increased rigidity. Alternately, modifications of the N-terminal end of the FokI domain result in an increase in DNA target binding and/or specificity.

In some embodiments, specificity of a TALE fusion protein is enhanced by increasing the potential for specifically binding, at the 5' and/or 3' ends of the target sequence, nucleotides other than T. Increasing the potential for specifically binding a nucleotide at the 5' of the target other than T may be accomplished by altering the amino acid of sequence of the N-cap, for example within the R-1 and R0 repeats. In some instances, alterations are made in the RVD region of the R-1 repeat unit. In other embodiments, alterations are made in the RVD region of the R0 repeat domains. In still further embodiments, alterations are made in both the R-1 and R0 repeat units. In any of the embodiments described herein, changes that alter the specificity for the DNA base immediately 5' of the base recognized by the R1 TALE repeat can be made. In some cases, the N-cap is then selectively able to interact with either A, or C or G, able to interact more selectively with a T, and in other instances, the N-cap is able to neutrally bind to any nucleotide or does not interact with any nucleotide. Increasing the potential for specifically binding nucleotides at the 3' end of the target sequence other than T is also accomplished by altering the amino acid sequence of the C-cap. In some instances alterations are made to the first 20 amino acids of the C-cap. In other instances, alterations are made to the first 83 amino acids of the C-cap.

The methods and compositions of the invention can be used to create a TALEN protein that acts as a "nickase" on the DNA, i.e., cleaves one strand of double-stranded DNA. In such "nicking" embodiments, one half of the nuclease dimer comprises a nuclease fusion partner that is inactive such that pairing of the inactive FokI half domain with another active FokI domain results in a cleavage protein that is only able to "nick" the DNA by cleaving only one strand. In some embodiments, two pairs of nickases are used to create dual DNA nicks on either strand of the target double-stranded DNA molecule. Use of the two nickase proteins enhances cleavage specificity at any chosen site, and also allows the user to design optimal overhangs on the DNA following cleavage.

The methods and compositions described herein allow for the development of TALENs and TALE TFs with increased specificity and/or activity for novel human and mammalian therapeutic applications, e.g., treatment of genetic diseases, cancer, fungal, protozoal, bacterial, and viral infection, ischemia, vascular disease, arthritis, immunological disorders, etc., as well as providing for functional genomics assays, and generating engineered cell lines for research and drug screening, and generate restriction enzymes to cleave DNA at any desired sites as a tool, and means for developing plants with altered phenotypes, including but not limited to, increased disease resistance, and altering fruit ripening characteristics, sugar and oil composition, yield, and color.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ M or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc-finger proteins have DNA-binding, RNA-binding and protein-binding activity.

A "TALE-repeat domain" (also "repeat array") is a sequence that is involved in the binding of the TALE to its cognate target DNA sequence and that comprises one or more TALE "repeat units." A single "repeat unit" (also referred to as a "repeat") is typically 33-35 amino acids in length and exhibits at least some sequence homology with other TALE repeat sequences within a naturally occurring TALE protein. A TALE repeat unit as described herein is generally of the form $(X)^{1\ to\ 11}\text{-}(X^{RVD})_2\text{-}(X)_{20\text{-}22}$ (SEQ ID NO:1) where $X^{RVD}$ (positions 12 and 13, where "RVD" refers to the repeat divariable residues at these positions) exhibit hypervariability in naturally occurring TALE proteins. Altering the identity of the RVD of each repeat (amino acids at positions 12 and 13) can alter the preference for the identity of the DNA nucleotide (or pair of complementary nucleotides in double-stranded DNA) with which the repeat unit interacts. There are four "canonical" RVDs (positions 12 and 13): NI (for binding to A), HD (for binding to C), NN (for binding to G) or NG (for binding to T). A "non-canonical" RVD includes any diresidue sequence other than the canonical NI, HD, NN, or NG. An "atypical" RVD is an RVD sequence (positions 12 and 13) that occurs infrequently or never in nature, for example, in less than 5% of naturally occurring TALE proteins, preferably in less than 2% of naturally occurring TALE proteins and even more preferably less than 1% of naturally occurring TALE proteins. An atypical RVD can also be non-naturally occurring. The terms "N-cap" polypeptide and "N-terminal sequence" are used to refer to an amino acid sequence (polypeptide) that flanks the N-terminal portion of the TALE repeat domain. The N-cap sequence can be of any length (including no amino acids), so long as the TALE-repeat domain(s) function to bind DNA. Thus, an N-cap sequence may be involved in supplying proper structural stabilization for the TALE repeat domain and/or nonspecific contacts with DNA. An N-cap sequence may be naturally occurring or non-naturally occurring, for example it may be derived from the N-terminal region of any full length TALE protein. The N-cap sequence is preferably a fragment (truncation) of a polypeptide found in full-length TALE proteins, for example any truncation of a N-terminal region flanking the TALE repeat domain in a naturally occurring TALE protein that is sufficient to support DNA-binding function of the TALE-repeat, domain or provide support for TALE fusion protein activity. When each TALE-repeat unit comprises a typical RVD and/or when the C-cap comprises a full-length naturally occurring C-terminal region of a TALE protein, the N-cap sequence does not comprise a full-length N-terminal region of a naturally occurring TALE protein. Thus, as noted above, this sequence is not necessarily involved in DNA recognition, but may enhance efficient and specific function at endogenous target DNA or efficient activity of the TALE fusion protein. The portion of the N-cap sequence closest to the N-terminal portion of the TALE repeat domain may bear some homology to a TALE repeat unit and is referred to as the "R0 repeat." Typically, the preferred nucleotide to the position immediately 5' of the target site is thymidine (T). It may be that the R0 repeat portion of the N-cap prefers to interact with a T (or the A base-paired to the T in double-stranded DNA) adjacent to the target sequence specified by the TALE repeats. Shown below is one example of an R0 sequence:

LDTGQLLKIAKRGGVTAVEAVHAWRNALTGAPLN (SEQ ID NO:2)

The region that is located adjacent to the R0 repeat on the N-terminal side can be referred to as the "R-1" region (or sequence) and the region located adjacent to the R0 repeat on the C-terminal side is referred to as the "R1" region (or sequence). Thus, both the R-1 and R0 repeats are within the N-cap. The R-1 region comprises a sequence of amino acids that display some characteristics resembling a regular TALE repeat unit, and thus may interact with the R0 repeat in a stabilizing manner or interact with a T (or the A base-paired to the T in double-stranded DNA) adjacent to the target sequence specified by the TALE repeats. An example of a R-1, R0 and R1 repeats from *Ralstonia* and a *Xanthomonas* TALE proteins are shown below where the underlined amino acids are in the RVD or RVD equivalent position:

Natural Xanthomonas variant (derived from TALE13; see co-owned U.S. Patent Publication 20110301073)

| | (SEQ ID NO: 3) |
|---|---|
| ATHEAIVGVGKQWSGARALEALLTVAGELRGPPLQ | R-1 TALE13 |

| | (SEQ ID NO: 4) |
|---|---|
| LDTGQLLKIAKR*GGVTAVEAVHAWRNALTGAPLN | R0 TALE13 |

| | (SEQ ID NO: 5) |
|---|---|
| LTPEQVVAIASNIGGKQALETVQRLLPVLCQAHG | R1 TALE13 |

Natural Xanthomonas variant (derived from Accession number AAQ79773.2)

| | (SEQ ID NO: 6) |
|---|---|
| ATHEDIVGVGKQLSGARALEALLTKAGELRGPPLQ | R-1 |

| | (SEQ ID NO: 7) |
|---|---|
| LDTGQLLKIARRG*GVTAVEAVHAWRNALTGAPLN | R0 |

| | (SEQ ID NO: 8) |
|---|---|
| LTPDQVVAIASNSGGKQALETVQRLLPVLCQDHG | R1 |

Ralstonia variant (derived from Accession number BAD42396.1)

| | (SEQ ID NO: 9) |
|---|---|
| LTRAHIVDIARQRSGDLALQALLPVATALTAAPLR | R-1 |

| | (SEQ ID NO: 10) |
|---|---|
| LSASQIATVAQYG*ERPAIQALYRLRRKLTRAPLH | R0 |

| | (SEQ ID NO: 11) |
|---|---|
| LTPQQVVAIASHDGGKPALEAVWAKLPVLRGVPYA | R1 |

The term "C-cap" or "C-terminal region" refers to optionally present amino acid sequences (polypeptides) that may be flanking the C-terminal portion of the TALE repeat domain. The C-cap can also comprise any part of a terminal C-terminal TALE repeat, including 0 residues, truncations of a TALE repeat or a full TALE repeat. The first 20 residues of the C-terminal region are typically homologous to the first 20 residues of a TALE repeat unit and may contain an RVD sequence capable of specifying the preference of nucleotides 3' of the DNA sequence specified by the TALE repeat domain. When present, this portion of the C-terminal region homologous to the first 20 residues of a TALE repeat is also referred to as the "half repeat." The numbering scheme of residues in the C-terminal region reflects this typical partial homology where the number scheme starts at C-20, increments to C-19, C-18, C-17, C-16, C-15, C-14, C-13, C-12, C-11, C-10, C-9, C-8, C-7, C-6, C-5, C-4, C-3, C-2, C-1, increments to C+1, and then increments to C+2, C+3, etc. towards the C-terminus of the polypeptide. A C+28 C-cap refers to the sequence from residue C-20 to residue C+28 (inclusive) and thus has a length of 48 residues. The C-cap sequences may be naturally occurring (e.g., fragments of naturally occurring proteins) or non-naturally occurring (e.g., a fragment of a naturally occurring protein comprising one or more amino acid deletions, substitutions and/or additions), or any other natural or non-natural sequence with the ability to act as a C cap. The C-terminal region is not absolutely required for the DNA-binding function of the TALE repeat domain(s), but, in some embodiments, a C-cap may interact with DNA and also may enhance the activity of functional domains, for example in a fusion protein comprising a nuclease at the C-terminal to the TALE repeat domain. See, also, U.S. Patent Publication No. 0110301073, incorporated by reference in its entirety herein.

A "zinc-finger DNA binding protein" (or binding domain) is a protein, or a domain within a larger protein, that binds DNA in a sequence-specific manner through one or more zinc-fingers, which are regions of amino acid sequence within the binding domain whose structure is stabilized through coordination of a zinc ion. The term zinc-finger DNA binding protein is often abbreviated as zinc-finger protein or ZFP.

A "selected" zinc-finger protein or protein comprising a TALE-repeat domain is a protein whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous sequence (i.e., donor polynucleotide sequence) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B D Hames and S. J. Higgins, (1985) Oxford; Washington, D.C.; IRL Press).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break (DSB) has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another. In some embodiments, two DSBs are introduced by the targeted nucleases described herein, resulting in the deletion of the DNA in between the DSBs. In some embodiments, the "donor" polynucleotides are inserted between these two DSBs.

Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

In any of the methods described herein, additional TALE-fusion proteins fused to nuclease domains as well as additional pairs of TALE-nucleases can be used for additional double-stranded cleavage of additional target sites within the cell. TALE-fusion proteins as described herein may also be used in combination with one more zinc finger nucleases (ZFNs).

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences (exogenous polynucleotide). The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage. "Nicking" refers to single-stranded cleavage specifically.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

"Double strand breaks" or "DSBs" are breaks in a DNA where both strands of the DNA molecule are broken. Those created by artificial nucleases have been used, for example, to induce targeted mutagenesis, induce targeted deletions of cellular DNA sequences, and facilitate targeted recombination at a predetermined chromosomal locus. See, for example, United States Patent Publications 20030232410; 20050208489; 20050026157; 20050064474; 20060188987; 20060063231; 20070218528; 20070134796; 20080015164 and International Publication Nos. WO 07/014,275 and WO 2007/139982, the disclosures of which are incorporated by reference in their entireties for all purposes. Thus, the ability to generate a DSB at a target genomic location allows for genomic editing of any genome. For example, zinc finger nuclease-mediated genome editing has been shown to modify the human genome at a specific location by (1) creation of a DSB in the genome of a living cell specifically at the target site for the desired modification, and by (2) allowing the natural mechanisms of DNA repair to "heal" this break.

There are two major and distinct pathways to repair DSBs-homologous recombination and non-homologous end joining (NHEJ). Homologous recombination requires the presence of a homologous sequence as a template (known as a "donor") to guide the cellular repair process and the results of the repair are error-free and predictable. In the absence of a template (or "donor") sequence for homologous recombination, the cell typically attempts to repair the DSB via the error-prone process of NHEJ.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474; 2007/0218528; 2008/0131962 and 2011/0201055, incorporated herein by reference in their entireties.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule. An exogenous molecule can also be a molecule normally found in another species, for example, a human sequence introduced into an animal's genome. An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAF-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional, endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a TALE-repeat domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA, shRNA, RNAi, miRNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

A "gap size" refers to the nucleotides between the two TALE targets sites on the nucleic acid target. Gaps can be any size, including but not limited to between 1 and 100 base pairs, or 5 and 30 base pairs, preferably between 10 and 25 base pairs, and more preferably between 12 and 21 base pairs. Thus, a preferable gap size may be 12, 13, 14, 15, 16, 17, 18, 19, 20, or 21 base pairs. The term. "spacer size" may be used interchangeable with the term "gap size".

"Modulation" of gene expression refers to a change in the activity of a gene. Modulation of expression can include, but is not limited to, gene activation and gene repression. Genome editing (e.g., cleavage, alteration, inactivation, donor integration, random mutation) can be used to modulate expression. Gene inactivation refers to any reduction in gene expression as compared to a cell that does not include a modifier as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a TALE-repeat domain is fused to a cleavage domain, the TALE-repeat domain and the cleavage domain are in operative linkage if, in the fusion polypeptide, the TALE-repeat domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same or has enhanced function as compared to the full-length protein, polypeptide or nucleic acid. Additionally, a functional fragment may have lesser function than the full-length protein, polypeptide or nucleic acid, but still have adequate function as defined by the user. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

TALE-repeat domains can be "engineered" to bind to a predetermined nucleotide sequence, for example via engineering (altering one or more amino acids) of the hypervariable diresidue region, for example positions 12 and/or 13 of a repeat unit within a TALE protein. In some embodiments, the amino acids at positions 4, 11, and 32 may be engineered. In other embodiments, atypical RVDs may be selected for use in an engineered TALE protein, enabling specification of a wider range of non-natural target sites. For example, a NK RVD may be selected for use in recognizing a G nucleotide in the target sequence. In other embodiments, amino acids in the repeat unit may be altered to change the characteristics (i.e. stability or secondary structure) of the repeat unit. Therefore, engineered TALE proteins are proteins that are non-naturally occurring. In some embodiments, the genes encoding TALE repeat domains are engineered at the DNA level such that the codons specifying the TALE repeat amino acids are altered, but the specified amino acids are not (e.g., via known techniques of codon optimization). Non-limiting examples of engineered TALE proteins are those obtained by design and/or selection. A designed TALE protein is a protein not occurring in nature whose design/composition results principally from rational criteria. Rational criteria for design include application of substitution rules and computerized algorithms for processing information in a database storing information of existing TALE designs and binding data. A "selected" TALE-repeat domain is a non-naturally occurring or atypical domain whose production results primarily from an empirical process such as phage display, interaction trap or hybrid selection.

A "multimerization domain" is a domain incorporated at the amino, carboxy or amino and carboxy terminal regions of a TALE-fusion protein. These domains allow for multimerization of multiple TALE-fusion protein units. Examples of multimerization domains include leucine zippers. Multimerization domains may also be regulated by small molecules wherein the multimerization domain assumes a proper conformation to allow for interaction with another multimerization domain only in the presence of a small molecule or external ligand. In this way, exogenous ligands can be used to regulate the activity of these domains.

The target sites useful in the above methods can be subject to evaluation by other criteria or can be used directly for design or selection (if needed) and production of a TALE-fusion protein specific for such a site. A further criterion for evaluating potential target sites is their proximity to particular regions within a gene. Target sites can be selected that do not necessarily include or overlap segments of demonstrable biological significance with target genes, such as regulatory sequences. Other criteria for further evaluating target segments include the prior availability of TALE-fusion proteins binding to such segments or related segments, and/or ease of designing new TALE-fusion proteins to bind a given target segment.

After a target segment has been selected, a TALE-fusion protein that binds to the segment can be provided by a variety of approaches. Once a TALE-fusion protein has been selected, designed, or otherwise provided to a given target segment, the TALE-fusion protein or the DNA encoding it are synthesized. Exemplary methods for synthesizing and expressing DNA encoding TALE-repeat domain-containing proteins are described below. The TALE-fusion protein or a polynucleotide encoding it can then be used for modulation of expression, or analysis of the target gene containing the target site to which the TALE-fusion protein binds.

TALE DNA Binding Domains

The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors "TALE" or "TAL-effectors") which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestris* pv. *Vesicatoria* (see Bonas et al (1989) *Mol Gen Genet* 218: 127-136 and WO2010079430). TALEs contain a centralized repeat domain that mediates DNA recognition, with each repeat unit containing approximately 33-35 amino acids specifying one target base. TALEs also contain nuclear localization sequences and several acidic transcriptional activation domains (see, e.g., Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

DNA-binding specificity of these TALEs depends on the sequences found in the tandem TALE repeat units. The repeated sequence comprises approximately 33-35 amino acids and the repeats are typically 91-100% homologous with each other (Bonas et al, ibid). There appears to be a one-to-one correspondence between the identity of the hypervariable diresidues at positions 12 and 13 with the identity of the contiguous nucleotides in the TALE's target sequence (see Moscou and Bogdanove, ibid and Boch et al ibid). These two adjacent amino acids are referred to as the Repeat Variable Diresidue (RVD). Experimentally, the natural code for DNA recognition of these TALEs has been determined such that an HD sequence at positions 12 and 13 leads to a binding to cytosine (C), NG binds to T, NI to A, NN binds to G or A, and NG binds to T. These TALE repeat units made up of canonical RVDs (HD, NG, NI and NN) have been assembled into proteins with new combinations of the natural TALE repeat units and altered numbers of repeats, to make variant TALE proteins. When in their native architecture, these variants are able to interact with new sequences and activate the expression of a reporter gene in plant cells (Boch et al., ibid.). However, these proteins maintain the native (full-length) TALE protein architecture and only the number and identity of the TALE repeat units within the construct were varied.

Entire or nearly entire TALE proteins have also been fused to a nuclease domain from the FokI protein to create a TALE-nuclease fusion protein ("TALEN"), and these TALENs have been shown to cleave an episomal reporter gene in yeast cells. (Christian et al. (2010) *Genetics* 186(2): 757-61; Li et al. (2011a) *Nucleic Acids Res.* 39(1):359-372); Li et al. (2011b) *Nucleic Acids Res.* epub doi:10.1093/nar/gkr188; Cermak et al. (2011) *Nucleic Acids Res.* epub doi:10.1093/nar/gkr218. However, the fact that a two step enrichment scheme was required to detect activity in plant and animal cells indicates that fusions between nearly entire TALE proteins and the nuclease domain from the FokI protein do not efficiently modify endogenous genes in plant and animal cells. In other words, the peptides used in these studies to link the TALE repeat array to the FokI cleavage domain does not appear to allow efficient cleavage by the FokI domain of endogenous genes in higher eukaryotes. These studies therefore highlight the need to develop compositions that can be used connect a TALE array (of repeat domains) with a nuclease domain for highly active cleavage of endogenous eukaryotic genes.

The polypeptides described herein comprise one or more (e.g., 1, 2, 3, 4, 5, 6, 7, 8, 9, 10, 11, 12, 13, 14, 15, 16, 17, 18, 19, 20 or even more) TALE-repeat units. See, also, U.S. Patent Publication No. 20110301073. In certain embodiments, the TALE DNA-binding polypeptide includes at least 6 distinct RVD sequences (i.e., 9 different diresidue sequences). The 6 distinct RVDs may be canonical, non-canonical and/or atypical. In other embodiments, the TALE DNA-binding proteins comprise 3 or more (3, 4, 5, 6, 7, 8 or more) non-canonical or atypical RVDs. TALE DNA binding domains, comprising multiple TALE-repeat units, have been studied to determine the sequences responsible for specificity. Within one organism, the TALE repeats typically are highly conserved (except for the RVD) but may not be well conserved across different species. A TALE-repeat unit as found in the polypeptides described herein is generally of the form: $X^1$-$X^2$-$X^3$-$X^4$-$X^5$-$X^6$-$X^7$-$X^8$-$X^9$-$X^{10}$-$X^{11}$-$(X^{RVD})_2$-$(X)_{20\text{-}22}$ (SEQ ID NO:12), where X is any amino acid and $X^{RVD}$ (positions 12 and 13) involved in DNA binding. Non-limiting exemplary embodiments of such domains include: embodiments in which $X^1$ comprises a leucine (L), or methionine (M) residue; embodiments in which $X^{10}$ comprises an alanine (A) residue or a valine (V) residue; embodiments in which $(X)_{20\text{-}22}$ comprises the sequence (Gly or Ser)-$(X)_{19\text{-}21}$ (SEQ ID NO:13); embodiments in which $(X)_{20\text{-}22}$ comprises the sequence $(X)_{3\text{-}4}$-(Ala or Thr)-$(X)_{16\text{-}17}$ (SEQ ID NO:14); embodiments in which $(X)_{20\text{-}22}$ comprises the sequence $(X)_{4\text{-}5}$-(Leu or Val)-$(X)_{15\text{-}16}$ (SEQ ID NO:15); and combinations of any of the above embodiments (e.g., $X^1$ comprises a leucine (L) or methionine (M) residue and $X^{10}$ comprises an alanine (A) residue; $X^1$ comprises L or M and $(X)_{20\text{-}22}$ comprises the sequence Gly/Ser-$(X)_{19\text{-}21}$ (SEQ ID NO:13); $(X)_{20\text{-}22}$ comprises the sequence Gly/Ser-$(X)_{2\text{-}3}$-Ala/Thr-$(X)_{16\text{-}17}$; $X^{10}$ comprises an alanine (A) or valine (V) residue and $(X)_{20\text{-}22}$ comprises the sequence Gly/Ser-$(X)_{19\text{-}21}$ (SEQ ID NO:13), etc.). In certain embodiments, the TALE-repeat comprises the RVDs (positions 12 and 13) shown in Tables 1 to 8 and/or the amino acids in position 11 shown in Tables 10 and 11.

The TALE-repeat units of the compositions and methods described herein may be derived from any suitable TALE-protein. Non-limiting examples of TALE proteins include TALE proteins derived from *Ralstonia* spp. or *Xanthamonas* spp. Thus, in some embodiments, the DNA-binding domain comprises one or more one or more naturally occurring and/or engineered TALE-repeat units derived from the plant pathogen *Xanthomonas* (see Boch et al, ibid and Moscou and Bogdanove, ibid). In other embodiments, the DNA-binding domain comprises one or more naturally occurring and/or engineered TALE-repeat units derived from the plant pathogen *Ralstonia solanacearum*, or other TALE DNA binding domain from the TALE protein family. The TALE DNA binding domains as described herein (comprising at least one TALE repeat unit) can include (i) one or more TALE repeat units not found in nature; (ii) one or more naturally occurring TALE repeat units; (iii) one or more TALE repeat units with atypical RVDs; and combinations of (i), (ii) and/or (iii). In some embodiments, a TALE DNA binding domain of the invention include only non-naturally occurring or atypical repeat units. Furthermore, in polypeptides as described herein comprising two or more TALE-repeat units, the TALE-repeat units (naturally occurring or engineered) may be derived from the same species or alternatively, may be derived from different species.

Several TALE DNA binding proteins have been identified and can be found in a standard GenBank search, including: AAB00675.1, (13.5 TALE repeats), AAB69865.1 (13.5 repeats), AAC43587.1 (17.5 repeats), AAD01494.1 (12.5 repeats), AAF98343.1 (25.5 repeats), AAG02079.2 (25.5 repeats), AAN01357.1 (8.5 repeats), AAO72098 (17.5 repeats), AAQ79773.2 (5.5 repeats), AAS46027.1 (28.5 repeats), AAS58127.2 (13.5 repeats), AAS58128.2 (17.5 repeats), AAS58129.3 (18.5 repeats), AAS58130.3 (9.5 repeats), AAT46123.1 (22.5 repeats), AAT46124.1 (26.5 repeats), AAW59491.1 (5.5 repeats), AAW59492.1 (16.5 repeats), AAW59493.1 (19.5 repeats), AAW77510.1 (5.5 repeats), AAY43358 (21.5 repeats), AAY43359.1 (11.5 repeats), AAY43360.1 (14.5 repeats), AAY54166.1 (19.5 repeats), AAY54168.1 (16.5 repeats), AAY54169.1 (12.5 repeats), AAY54170.1 (23.5 repeats), ABB70129.1 (21.5 repeats), ABB70183.1 (22.5 repeats), ABO77779.1 (17.5 repeats), etc. TALE type proteins have also been found in the bacterium *Ralstonia solanacearum*. Examples of TALE type proteins from *Ralstonia* include ABO27069.1 (10.5 repeats), ABO27070.1 (11.5 repeats), ABO27071.1 (7.5 repeats), ABO27072.1 (3.5 repeats), etc.

The DNA-binding polypeptides comprising TALE-repeat domains as described herein may also include additional TALE polypeptide sequences, for example N-terminal (N-cap) sequences and, optionally, C-terminal (C-cap) sequences flanking the repeat domains. N-cap sequences may be naturally or non-naturally occurring sequences of any length sufficient to support the function (e.g., DNA-binding, cleavage, activation, etc.) of the DNA-binding polypeptide and fusion proteins comprising these TALE-repeat domain-containing DNA-binding polypeptides. In certain embodiments, the protein comprises an N-cap sequence comprising a fragment (truncation) of a region of a TALE protein N-terminal to the repeat domain (e.g., an N-cap sequence comprising at least 130 to 140 residues (e.g., 131, 132, 133, 134, 135, 136, 137, 138, 139 or 140 residues) of a TALE polypeptide N-terminal of the repeat domain). In other embodiments, the TALE-repeat domain polypeptides as described herein the protein comprises a C-cap sequence comprising a fragment (truncated) region of a TALE protein C-terminal to the repeat domain (e.g., an C-cap sequence comprising C-20 to C+28, C-20 to C+55, or C-20 to C+63). In certain embodiments, the C-cap sequence comprises a half-repeat (C-20 to C-1). The TALE DNA-binding polypeptides as described herein may include N-cap, C-cap sequences or both N-cap and C-cap sequences.

Artificial TALE proteins and TALE fusion proteins can be produced to bind to a novel sequence using natural or engineered TALE repeat units (see Boch et al, ibid and Morbitzer et al, (2010) *Proc. Natl. Acad. Sci. USA* 107(50): 21617-21622). See, also e.g., WO 2010/079430. When this novel target sequence was inserted upstream of a reporter gene in plant cells, the researchers were able to demonstrate activation of the reporter gene. Artificial TALE fusions comprising the FokI cleavage domain can also cleave DNA in living cells (see Christian et al, ibid, Li et al (2011a) and (2011b) ibid, Cernak et al (2011) *Nucl. Acid. Res.* epub doi:10.1093/nar/gcr218; U.S. Patent Publication No. 20110301073.

An engineered TALE protein and TALE fusion protein can have a novel binding specificity, compared to a naturally-occurring TALE protein. Engineering methods include, but are not limited to, rational design and various types of selection. Rational design includes, for example, using databases comprising nucleotide sequences for modules for single or multiple TALE repeats. Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In naturally occurring TALE proteins, only a limited repertoire of potential dipeptide motifs are typically employed. Thus, as described herein, TALE related domains containing all possible mono- and di-peptide sequences have been constructed and assembled into candidate TALE proteins. Thus, in certain embodiments, one or more TALE-repeat units of the DNA-binding protein comprise atypical RVDs, for example as shown in Tables 1 to 6.

Additionally, in naturally occurring TALE proteins, the repeat units often show little variability within the framework sequence (i.e. the residue(s) not involved in direct DNA contact (non-RVD residues). This lack of variability may be due to a number of factors including evolutionary relationships between individual TALE repeat units and protein folding requirements between adjacent repeats. Between differing phytopathogenic bacterial genera however the framework sequences can vary. For example, the TALE repeat sequences in the *Xanthomonas campestris* pv *vesicatoria*, the protein AvrBs3 has less than 40% homology with brg11 and hpx17 repeat units from *Ralstonia solanacearum* (see Heuer et al (2007) *Appl Environ Micro* 73 (13): 4379-4384). The TALE repeat may be under stringent functional selection in each bacterium's natural environment, e.g., from the sequence of the genes in the host plant that the TALE regulates. Thus, as described herein, variants in the TALE framework (e.g., within the TALE repeat unit or sequences outside the repeat units such as N-cap and C-cap sequences) may be introduced by targeted or random mutagenesis by various methods know in the art, and the resultant TALE fusion proteins screened for optimal activity. In certain embodiments, position 11 of one or more of the TALE repeats comprises an amino acid as shown in Tables 10 and 11 (e.g., altered as compared to a wild-type residue at position 11).

Multi TALE repeat modules may also be useful not only for assembling the DNA binding domains (comprising at least one TALE repeat unit) as described above, but also may be useful for the assembly of mini-TALE multimers (i.e. 3 or more repeat units, including trimers, tetramers, pentamers, hexamers etc.), wherein spanning linkers that also functioned as capping regions between the mini-TALE DNA binding domains would allow for base skipping and may result in higher DNA binding specificity. The use of linked mini-TALE DNA binding domains would relax the requirement for strict functional modularity at the level of individual TALE repeats and allows for the development of more complex and/or specific DNA recognition schemes wherein amino acids from adjacent motifs within a given module might be free to interact with each other for cooperative recognition of a desired DNA target sequence. Mini-TALE DNA binding domains could be linked and expressed using a suitable selection system (i.e. phage display) with randomized dipeptide motifs (or any other identified key positions) and selected based on their nucleic acid binding characteristics. Alternatively, multi-TALE repeat modules may be used to create an archive of repeat modules to allow for rapid construction of any specific desired TALE-fusion protein.

Selection of target sites and methods for design and construction of fusion proteins (and polynucleotides encoding same) are known to those of skill in the art and described in detail in U.S. Patent Application Publication Nos. 20050064474; 20060188987, and 20110301073, incorporated by reference in their entireties herein.

Artificial fusion proteins linking TALE DNA binding domains to zinc finger DNA binding domains may also be produced. These fusions may also be further linked to a desired functional domain.

In addition, as disclosed in these and other references, TALE DNA binding domains and/or zinc finger domains may be linked together using any suitable linker sequences, including for example, linkers of 5 or more amino acids in length (e.g., TGEKP (SEQ ID NO:16), TGGQRP (SEQ ID NO:17), TGQKP (SEQ ID NO:18), and/or TGSQKP (SEQ ID NO:19)), although it is likely that sequences that can function as capping sequence (N-cap and C-cap sequences) would be required at the interface between the TALE repeat domain and the linker. Thus, when linkers are used, linkers of five or more amino acids can be used in conjunction with the cap sequences to join the TALE DNA binding domains to a desired fusion partner domain. See, also, U.S. Pat. Nos. 6,479,626; 6,903,185; and 7,153,949 for exemplary linker sequences 6 or more amino acids in length. In addition, linkers between the TALE repeat domains and the fused functional protein domains can be constructed to be either flexible or positionally constrained (rigid) to allow for the most efficient genomic modification. See, also, Example 1. Linkers of varying lengths and compositions may be tested.

Fusion Proteins

Fusion proteins comprising DNA-binding proteins (e.g., TALE-fusion proteins) as described herein and a heterologous regulatory or functional domain (or functional fragment thereof) are also provided. Common domains include, e.g., transcription factor domains (activators, repressors, co-activators, co-repressors), nuclease domains, silencer domains, oncogene domains (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases), DNA targeting enzymes such as transposons, integrases, recombinases and resolvases and their associated factors and modifiers, nuclear hormone receptors, nucleases (cleavage domains or half-domains) and ligand binding domains. Other fusion proteins may include reporter or selection markers. Examples of reporter domains include GFP, GUS and the like. Reporters with specific utility in plant cells include GUS.

Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Barik, *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO J.* 18, 6439-6447). Additional exemplary activation domains include, Oct 1, Oct-2A, Sp1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al. (2000) *Mol. Endocrinol.* 14:329-347; Collingwood et al. (1999) *J. Mol. Endocrinol.* 23:255-275; Leo et al. (2000) *Gene* 245:1-11; Manteuffel-Cymborowska (1999) *Acta Biochim. Pol.* 46:77-89; McKenna et al. (1999) *J. Steroid Biochem. Mol. Biol.* 69:3-12; Malik et al. (2000) *Trends Biochem. Sci.* 25:277-283; and Lemon et al. (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al. (2000) *Gene* 245:21-29; Okanami et al. (1996) *Genes Cells* 1:87-99; Goff et al. (1991) *Genes Dev.* 5:298-309; Cho et al. (1999) *Plant Mol. Biol.* 40:419-429; Ulmason et al. (1999) *Proc. Natl. Acad. Sci. USA* 96:5844-5849; Sprenger-Haussels et al. (2000) *Plant J.* 22:1-8; Gong et al. (1999) *Plant Mol. Biol.* 41:33-44; and Hobo et al. (1999) *Proc. Natl. Acad. Sci. USA* 96:15,348-15,353.

It will be clear to those of skill in the art that, in the formation of a fusion protein (or a nucleic acid encoding same) between a DNA-binding domain as described herein and a functional domain, either an activation domain or a molecule that interacts with an activation domain is suitable as a functional domain Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in co-owned U.S. Patent Applications 2002/0115215 and 2003/0082552 and in co-owned WO 02/44376.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al. (1999) *Cell* 99:451-454; Tyler et al. (1999) *Cell* 99:443-446; Knoepfler et al. (1999) *Cell* 99:447-450; and Robertson et al. (2000) *Nature Genet.* 25:338-342. Additional exemplary repression domains include, but are not limited to, ROM2 and AtHD2A. See, for example, Chem et al. (1996) *Plant Cell* 8:305-321; and Wu et al. (2000) *Plant J.* 22:19-27.

In certain embodiments, the target site bound by the TALE-fusion protein is present in an accessible region of cellular chromatin Accessible regions can be determined as described, for example, in co-owned International Publication WO 01/83732. If the target site is not present in an accessible region of cellular chromatin, one or more accessible regions can be generated as described in co-owned WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al. (1987) *Cell* 48:261-270; Pina et al. (1990) *Cell* 60:719-731; and Cirillo et al. (1998) *EMBO J.* 17:244-254.

The fusion molecule may be formulated with a pharmaceutically acceptable carrier, as is known to those of skill in the art. See, for example, Remington's Pharmaceutical Sciences, 17th ed., 1985; and co-owned WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in co-owned U.S. Pat. No. 6,534,261 and US Patent Application Publication No. 2002/0160940.

Functional domains that are regulated by exogenous small molecules or ligands may also be selected. For example, RheoSwitch® technology may be employed wherein a functional domain only assumes its active conformation in the presence of the external RheoChem™ ligand (see for example US 20090136465). Thus, the TALE-fusion protein may be operably linked to the regulatable functional domain wherein the resultant activity of the TALE-fusion protein is controlled by the external ligand.

In certain embodiments, the TALE DNA-binding proteins, or fragments thereof, are used as nucleases via fusion (N- and/or C-terminal to the TALE-repeat domain, N-cap and/or C-cap sequences) of a TALE DNA-binding domain to at least one nuclease (cleavage domain, cleavage half-domain). The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more TALE DNA-binding domains, which may or may not be engineered.

Exemplary Type IIS restriction enzymes, whose cleavage domains are separable from the binding domain, include Fok I and BfiI (see Zaremba et al, (2004) *J Mol Biol.* 336(1): 81-92). FokI enzyme is active as a dimer (see Bitinaite et al. (1998) *Proc. Natl. Acad. Sci. USA* 95: 10,570-10,575). For targeted double-stranded cleavage and/or targeted replacement of cellular sequences using TALE repeat domain-Fok I fusions (or variants thereof further comprising a C-cap and an N-cap), two fusion proteins, each comprising a FokI cleavage half-domain, can be used to reconstitute a catalytically active cleavage domain. Alternatively, a single polypeptide molecule containing a TALE-repeat domain and two Fok I cleavage half-domains can also be used. Another preferred Type IIS restriction enzyme is BfiI (see Zaremba et al, (2004) *J Mol Biol.* 336(1):81-92). The cleavage domain of this enzyme may be separated from its DNA binding domain and operably linked to a TALE DNA binding domain to create a TALEN.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

To enhance cleavage specificity, in certain embodiments, the cleavage domain comprises one or more engineered cleavage half-domain (also referred to as dimerization domain mutants) that minimize or prevent homodimerization, as described, for example, in U.S. Pat. No. Publication Nos. 20050064474; 20060188987; 20080131962; 20090311787; 20090305346; 20110014616, and 20110201055, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Additional engineered cleavage half-domains of Fok I form an obligate heterodimers can also be used in the fusion proteins described herein. The first cleavage half-domain includes mutations at amino acid residues at positions 490 and 538 of Fok I and the second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., Example 1 of U.S. Patent Publication No. 2008/0131962, the disclosure of which is incorporated by reference in its entirety for all purposes.

The engineered cleavage half-domains described herein are obligate heterodimer mutants in which aberrant cleavage is minimized or abolished. See, e.g., Example 1 of WO 07/139,898. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See, U.S. Patent Publication No. 2011/0201055). The nuclease pairing of the ELD FokI variant with KKR FokI variant is referred to as "eHiFi". In addition, the FokI nuclease domain variants including mutations known as "Sharkey" or "Sharkey' (Sharkey prime)" mutations may be used (see Guo et al, (2010) *J. Mol. Biol.* doi:10.1016/j.jmb.2010.04.060).

Engineered cleavage half-domains described herein can be prepared using any suitable method, for example, by site-directed mutagenesis of wild-type cleavage half-domains (Fok I) as described in U.S. Patent Publication Nos. 20050064474, 20070134796; 20080131962; 2011/0201055.

In certain embodiments, amino acids extending approximately 383 through 454, and subsets thereof, of the FokI cleavage domain are deleted, where the numbering is relative to that of the native FokI protein. The invention also provides compositions and methods for altering the FokI sequence from approximately amino acids 373 to 383, numbered relative to the native FokI protein. The deletions result in a more active FokI nuclease domain as compared to a FokI domain without the deletions.

TALE-fusion polypeptides and nucleic acids can be made using routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)). In addition, essentially any nucleic acid can be custom ordered from any of a variety of commercial sources. Similarly, peptides and antibodies can be custom ordered from any of a variety of commercial sources.

Two alternative methods are typically used to create the coding sequences required to express newly designed DNA-binding peptides. One protocol is a PCR-based assembly procedure that utilizes overlapping oligonucleotides. These oligonucleotides contain substitutions primarily, but not limited to, positions 12 and 13 on the repeated domains making them specific for each of the different DNA-binding domains. Additionally, amino acid substitutions may be made at positions 4, 11 and 32 Amino acid substitutions may also be made at positions 2, 3, 4, 21, 23, 24, 25, 27, 30, 31, 33, 34 and/or 35 within one repeat unit. In some embodiments, the repeat unit contains a substitution in one position, and in others, the repeat unit contains from 2 to 18 amino acid substitutions. In some embodiments, the nucleotide sequence of the repeat units may be altered without altering the amino acid sequence.

Any suitable method of protein purification known to those of skill in the art can be used to purify TALE-fusion proteins of the invention (see Ausubel, supra, Sambrook, supra). In addition, any suitable host can be used, e.g., bacterial cells, insect cells, yeast cells, mammalian cells, and the like.

Thus, fusion molecules are constructed by methods of cloning and biochemical conjugation that are well known to those of skill in the art. Fusion molecules comprise a DNA-binding domain and a functional domain (e.g., a transcriptional activation or repression domain) Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion. The fusion proteins as described herein may include one or more functional domains at the N- and/or C-terminus of the DNA-binding polypeptides as described herein.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al. (2000) *Proc. Natl. Acad. Sci. USA* 97:3930-3935.

Delivery

The TALE-fusion proteins, polynucleotides encoding same and compositions comprising the proteins and/or polynucleotides described herein may be delivered to a target cell by any suitable means, including, for example, by injection of mRNA encoding the TALE-fusion protein. See, Hammerschmidt et al. (1999) *Methods Cell Biol.* 59:87-115.

Methods of delivering proteins comprising engineered transcription factors are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

TALE-protein fusions as described herein may also be delivered using vectors containing sequences encoding one or more of the TALE-protein fusions. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more TALE-protein fusions encoding sequences. Thus, when one or more TALE-protein fusions (e.g., a pair of TALENs) are introduced into the cell, the TALE-protein fusions may be carried on the same vector or on different vectors. When multiple vectors are used, each vector may comprise a sequence encoding one or multiple TALE-protein fusions.

Conventional viral and non-viral based gene transfer methods can be used to introduce nucleic acids encoding engineered TALE-protein fusions in cells (e.g. mammalian cells) whole organisms or target tissues. Such methods can also be used to administer nucleic acids encoding TALE-protein fusions to cells in vitro. In certain embodiments, nucleic acids encoding TALE protein fusions are administered for in vivo or ex vivo uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology Doerfler and Bohm* (eds.) (1995); and Yu et al., *Gene Therapy* 1:13-26 (1994).

Non-viral vector delivery systems include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids. Viral vector delivery systems include DNA and RNA viruses, which have either episomal or integrated genomes after delivery to the cell. Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one ami of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7) p. 643).

Suitable cells include but are not limited to eukaryotic cells and/or prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with the TALE-fusions. Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells, neuronal stem cells, mesenchymal stem cells, muscle stem cells and skin stem cells.

Stem cells that have been modified may also be used in some embodiments. For example, stem cells that have been made resistant to apoptosis may be used as therapeutic compositions where the stem cells also contain the TALE-fusion proteins of the invention. Resistance to apoptosis may come about, for example, by knocking out BAX and/or BAK using BAX- or BAK-specific TALENs in the stem cells, or those that are disrupted in a caspase, again using caspase-6 specific TALENs for example.

Methods for introduction of DNA into hematopoietic stem cells are disclosed, for example, in U.S. Pat. No. 5,928,638. Vectors useful for introduction of transgenes into hematopoietic stem cells, e.g., CD34$^+$ cells, include adenovirus Type 35.

Vectors suitable for introduction of polynucleotides as described herein include described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/054985. As noted above, the disclosed methods and compositions can be used in any type of cell. Progeny, variants and derivatives of animal cells can also be used.

DNA constructs may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al (1987) *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) *Science* 233:496-498, and Fraley et al (1983) *Proc. Nat'l. Acad. Sci. USA* 80:4803.

In addition, gene transfer may be achieved using non-*Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al (1985) *Science* 227:1229-1231). Generally, the *Agrobacterium* transformation system is used to engineer dicotyledonous plants (Bevan et al (1982) *Ann. Rev. Genet* 16:357-384; Rogers et al (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al (1984) *EMBO J* 3:3039-3041; Hooykass-Van Slogteren et al (1984) *Nature* 311:763-764; Grimsley et al (1987) *Nature* 325:1677-179; Boulton et al (1989) *Plant Mol. Biol.* 12:31-40; and Gould et al (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

Organisms

The methods and compositions described herein are applicable to any organism in which it is desired to regulate gene expression and/or alter the organism through genomic modification, including but not limited to eukaryotic organisms such as plants, animals (e.g., mammals such as mice, rats, primates, farm animals, rabbits, etc.), fish, and the like. Eukaryotic (e.g., yeast, plant, fungal, piscine and mammalian cells such as feline, canine, murine, bovine, ovine, and porcine) cells can be used. Cells from organisms containing one or more homozygous KO loci as described herein or other genetic modifications can also be used.

Exemplary mammalian cells include any cell or cell line of the organism of interest, for example oocytes, K562 cells, CHO (Chinese hamster ovary) cells, HEP-G2 cells, BaF-3 cells, Schneider cells, COS cells (monkey kidney cells expressing SV40 T-antigen), CV-1 cells, HuTu80 cells, NTERA2 cells, NB4 cells, HL-60 cells and HeLa cells, 293 cells (see, e.g., Graham et al. (1977) *J. Gen. Virol.* 36:59), and myeloma cells like SP2 or NS0 (see, e.g., Galfre and Milstein (1981) *Meth. Enzymol.* 73(B):3 46). Peripheral blood mononucleocytes (PBMCs) or T-cells can also be used, as can embryonic and adult stem cells. For example, stem cells that can be used include embryonic stem cells (ES), induced pluripotent stem cells (iPSC), mesenchymal stem cells, hematopoietic stem cells, liver stem cells, skin stem cells and neuronal stem cells.

Exemplary target plants and plant cells include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); vegetative crops for consumption (e.g. soybean and other legumes, squash, peppers, eggplant, celery etc), flowering plants (e.g., petunia, rose, chrysanthemum), conifers and pine trees (e.g., pine fir, spruce); poplar trees (e.g. *P. tremula* × *P. alba*); fiber crops (cotton, jute, flax, bamboo) plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*. The term plant cells include isolated plant cells as well as whole plants or portions of whole plants such as seeds, callus, leaves, roots, etc. The present disclosure also encompasses seeds of the plants described above wherein the seed has the transgene or gene construct and/or has been modified using the compositions and/or methods described herein. The present disclosure further encompasses the progeny, clones, cell lines or cells of the transgenic plants described above wherein said progeny, clone, cell line or cell has the transgene or gene construct. Algae are being increasingly utilized for manufacturing compounds of interest, i.e. biofuels, plastics, hydrocarbons etc. Exemplary algae species include microalgae including diatoms and cyanobacteria as well as *Botryococcus braunii, Chlorella, Dunaliella tertiolecta, Gracileria, Pleurochrysis carterae, Sorgassum* and *Ulva*.

Assays for Determining Regulation of Gene Expression by TALE Fusion Proteins

A variety of assays can be used to determine the level of gene expression regulation by TALE-fusion proteins. The activity of a particular TALE-fusion proteins can be assessed using a variety of in vitro and in vivo assays, by measuring, e.g., protein or mRNA levels, product levels, enzyme activity, tumor growth; transcriptional activation or repression of a reporter gene; second messenger levels (e.g., cGMP, cAMP, IP3, DAG, Ca.sup.2+); cytokine and hormone production levels; and neovascularization, using, e.g., immunoassays (e.g., ELISA and immunohistochemical assays with antibodies), hybridization assays (e.g., RNase protection, northerns, in situ hybridization, oligonucleotide array studies), colorimetric assays, amplification assays, enzyme activity assays, tumor growth assays, phenotypic assays, and the like.

TALE-fusion proteins are typically first tested for activity in vitro using cultured cells, e.g., 293 cells, CHO cells, VERO cells, BHK cells, HeLa cells, COS cells, plant cell lines, plant callous cultures and the like. Preferably, human cells are used. The TALE-fusion protein is often first tested using a transient expression system with a reporter gene, and then regulation of the target endogenous gene is tested in cells and in animals, both in vivo and ex vivo. The TALE fusion proteins can be recombinantly expressed in a cell, recombinantly expressed in cells transplanted into an animal or plant, or recombinantly expressed in a transgenic animal or plant, as well as administered as a protein to an animal, plant or cell using delivery vehicles described herein. The cells can be immobilized, be in solution, be injected into an animal, or be naturally occurring in a transgenic or non-transgenic animal.

Modulation of gene expression is tested using one of the in vitro or in vivo assays described herein. Samples or assays are treated with a TALE-fusion protein and compared to control samples without the test compound, to examine the extent of modulation.

The effects of the TALE-fusion proteins can be measured by examining any of the parameters described above. Any suitable gene expression, phenotypic, or physiological change can be used to assess the influence of a TALE-fusion protein. When the functional consequences are determined using intact cells or animals, one can also measure a variety of effects such as tumor growth, neovascularization, hormone release, transcriptional changes to both known and uncharacterized genetic markers (e.g., northern blots or oligonucleotide array studies), changes in cell metabolism such as cell growth or pH changes, and changes in intracellular second messengers such as cGMP.

Preferred assays for TALE-fusion protein mediated regulation of endogenous gene expression can be performed in vitro. In one preferred in vitro assay format, TALE-fusion protein mediated regulation of endogenous gene expression in cultured cells is measured by examining protein production using an ELISA assay. The test sample is compared to control cells treated with an empty vector or an unrelated TALE-fusion protein that is targeted to another gene.

In another embodiment, TALE-fusion protein-mediated regulation of endogenous gene expression is determined in vitro by measuring the level of target gene mRNA expression. The level of gene expression is measured using amplification, e.g., using PCR, LCR, or hybridization assays, e.g., northern hybridization, RNase protection, dot blotting. RNase protection is used in one embodiment. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using the target gene promoter operably linked to a reporter gene such as luciferase, green fluorescent protein, CAT, or beta-gal. The reporter construct is typically co-transfected into a cultured cell. After treatment with the TALE-fusion proteins of choice, the amount of reporter gene transcription, translation, or activity is measured according to standard techniques known to those of skill in the art.

Another example of a preferred assay format useful for monitoring TALE-fusion protein mediated regulation of endogenous gene expression is performed in vivo. This assay is particularly useful for examining TALE-fusions that inhibit expression of tumor promoting genes, genes involved in tumor support, such as neovascularization (e.g., VEGF), or that activate tumor suppressor genes such as p53. In this assay, cultured tumor cells expressing the TALE-fusions of choice are injected subcutaneously into an immune compromised mouse such as an athymic mouse, an irradiated mouse, or a SCID mouse. After a suitable length of time, preferably 4-8 weeks, tumor growth is measured, e.g., by volume or by its two largest dimensions, and compared to the control. Tumors that have statistically significant reduction (using, e.g., Student's T test) are said to have inhibited growth. Alternatively, the extent of tumor neovascularization can also be measured. Immunoassays using endothelial cell specific antibodies are used to stain for vascularization of the tumor and the number of vessels in the tumor. Tumors that have a statistically significant reduction in the number of vessels (using, e.g., Student's T test) are said to have inhibited neovascularization.

Transgenic and non-transgenic plants or animals as described above are also used as a preferred embodiment for examining regulation of endogenous gene expression in vivo. Transgenic organisms typically express the TALE-fusions of choice. Alternatively, organisms that transiently express the TALE-fusions of choice, or to which the TALE fusion proteins have been administered in a delivery vehicle, can be used. Regulation of endogenous gene expression is tested using any one of the assays described herein.

Nucleic Acids Encoding TALE-Fusion Proteins

Conventional viral and non-viral based gene transfer methods can be used to introduce nucleic acids encoding engineered TALE domain fusions in mammalian cells, in whole organisms or in target tissues. Such methods can be used to administer nucleic acids encoding TALE domain fusions to cells in vitro. Preferably, the nucleic acids encoding TALE domain fusions are administered for in vivo or ex vivo uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds) (1995); and Yu et al., *Gene Therapy* 1:13-26 (1994).

The use of RNA or DNA viral based systems for the delivery of nucleic acids encoding engineered TALE domain fusions takes advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of TALE domain fusions could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long teen expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., *J. Virol.* 66:2731-2739 (1992); Johann et al., *J. Virol.* 66:1635-1640 (1992); Sommerfelt et al, *Virol.* 176:58-59 (1990); Wilson et al., *J. Virol.* 63:2374-2378 (1989); Miller et al., *J. Virol.* 65:2220-2224 (1991); PCT/US94/05700).

In applications where transient expression of the TALE domain fusions is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, Human Gene Therapy 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol Cell. Biol.* 4:2072-2081 (1984); Hermonat & Muzyczka, *Proc Natl Acad Sci USA* 81:6466-6470 (1984); and Samulski et al., *J. Virol.* 63:03822-3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048-305 (1995); Kohn et al., *Nat. Med.* 1:1017-102 (1995); Malech et al., *Proc Natl Acad Sci USA* 94:22 12133-12138 (1997)). PA317/pLASN was the first therapeutic vector used in a gene therapy trial. (Blaese et al., *Science* 270:475480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative to gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) are predominantly used for colon cancer gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer include Rosenecker et al, *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998); U.S. Patent Publication No. 2008/0159996.

Packaging cells are used to form virus particles that are capable of infecting a host cell. Such cells include 293 cells, which package adenovirus, and psi2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome, which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc Natl Acad Sci USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus, expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a TALE fusion nucleic acid (gene or cDNA), and re-infused back into the subject organism (e.g., patient). Various cell types suitable for ex vivo transfection are well known to those of skill in the art (see, e.g., Freshney et al., Culture of Animal Cells, A Manual of Basic Technique (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-.gamma and TNF-alpha are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panb cells), GR-1 (granulocytes), and Tad (differentiated antigen presenting cells) (see Inaba et al., *J. Exp. Med.* 176:1693-1702 (1992)). Exemplary stem cells include human embryonic stem cells (hES), induced pluripotent stem cells (iPSC), hematopoietic stem cells, mesenchymal stem cells, neuronal stem cells, and muscle stem cells.

Vectors (e.g., retroviruses, adenoviruses, liposomes, etc.) containing therapeutic TALE domain fusion nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., Remington's Pharmaceutical Sciences, 17th ed., 1989).

Pharmaceutical Compositions and Administration

TALE-fusions and expression vectors encoding TALE fusions can be administered directly to the patient for modulation of gene expression and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, hemophilia, hemoglobinopathies and the like. Examples of microorganisms that can be inhibited by TALE fusion protein gene therapy include pathogenic bacteria, e.g., chlamydia, rickettsial bacteria, mycobacteria, staphylococci, streptococci, pneumococci, meningococci and conococci, klebsiella, proteus, serratia, pseudomonas, legionella, diphtheria, salmonella, bacilli, cholera, tetanus, botulism, anthrax, plague, leptospirosis, and Lyme disease bacteria; infectious fungus, e.g., Aspergillus, Candida species; protozoa such as sporozoa (e.g., *Plasmodia*), rhizopods (e.g., Entamoeba) and flagellates (*Trypanosoma, Leishmania, Trichomonas, Giardia,* etc.); viral diseases, e.g., hepatitis (A, B, or C), herpes virus (e.g. VZV, HSV-1, HSV-6, HSV-II, CMV, and EBV), HIV, Ebola, adenovirus, influenza virus, flaviviruses, echovirus, rhinovirus, coxsackie virus, comovirus, respiratory syncytial virus, mumps virus, rotavirus, measles virus, rubella virus, parvovirus, vaccinia virus, HTLV virus, dengue virus, papillomavirus, poliovirus, rabies virus, and arboviral encephalitis virus, etc.

Administration of therapeutically effective amounts is by any of the routes normally used for introducing TALE-fusions into ultimate contact with the tissue to be treated. The TALE-fusions are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

Regulation of Gene Expression in Plants

TALE-fusions can be used to engineer plants for traits such as increased disease resistance, modification of structural and storage polysaccharides, flavors, proteins, and fatty acids, fruit ripening, yield, color, nutritional characteristics, improved storage capability, drought or submergence/flood tolerance, and the like. In particular, the engineering of crop species for enhanced oil production, e.g., the modification of the fatty acids produced in oilseeds, is of interest. See, e.g., U.S. Pat. No. 7,262,054; and U.S. Patent Publication Nos. 2008/0182332 and 20090205083.

Seed oils are composed primarily of triacylglycerols (TAGs), which are glycerol esters of fatty acids. Commercial production of these vegetable oils is accounted for primarily by six major oil crops (soybean, oil palm, rapeseed, sunflower, cotton seed, and peanut.) Vegetable oils are used predominantly (90%) for human consumption as margarine, shortening, salad oils, and flying oil. The remaining 10% is used for non-food applications such as lubricants, oleochemicals, biofuels, detergents, and other industrial applications.

The desired characteristics of the oil used in each of these applications varies widely, particularly in terms of the chain length and number of double bonds present in the fatty acids making up the TAGs. These properties are manipulated by the plant in order to control membrane fluidity and temperature sensitivity. The same properties can be controlled using TALE domain fusions to produce oils with improved characteristics for food and industrial uses.

The primary fatty acids in the TAGs of oilseed crops are 16 to 18 carbons in length and contain 0 to 3 double bonds. Palmitic acid (16:0 [16 carbons: 0 double bonds]), oleic acid (18:1), linoleic acid (18:2), and linolenic acid (18:3) predominate. The number of double bonds, or degree of saturation, determines the melting temperature, reactivity, cooking performance, and health attributes of the resulting oil.

The enzyme responsible for the conversion of oleic acid (18:1) into linoleic acid (18:2) (which is then the precursor for 18:3 formation) is DELTA12-oleate desaturase, also referred to as omega-6 desaturase. A block at this step in the fatty acid desaturation pathway should result in the accumulation of oleic acid at the expense of polyunsaturates.

In one embodiment proteins containing TALE domain(s) are used to regulate expression of the FAD2-1 gene in soybeans. Two genes encoding microsomal DELTA.6 desaturases have been cloned recently from soybean, and are referred to as FAD2-1 and FAD2-2 (Heppard et al., *Plant Physiol.* 110:311-319 (1996)). FAD2-1 (delta 12 desaturase) appears to control the bulk of oleic acid desaturation in the soybean seed. TALE-fusions can thus be used to modulate gene expression of FAD2-1 in plants. Specifically, TALE domain fusions can be used to inhibit expression of the FAD2-1 gene in soybean in order to increase the accumulation of oleic acid (18:1) in the oil seed. Moreover, TALE-fusions can be used to modulate expression of any other plant gene, such as delta-9 desaturase, delta-12 desaturases from other plants, delta-15 desaturase, acetyl-CoA carboxylase, acyl-ACP-thioesterase, ADP-glucose pyrophosphorylase, starch synthase; cellulose synthase, sucrose synthase, senescence-associated genes, heavy metal chelators, fatty acid hydroperoxide lyase, polygalacturonase, EPSP synthase, plant viral genes, plant fungal pathogen genes, and plant bacterial pathogen genes.

Functional Genomics Assays

TALE-fusions also have use in assays to determine the phenotypic consequences and function of gene expression. The recent advances in analytical techniques, coupled with focused mass sequencing efforts have created the opportunity to identify and characterize many more molecular targets than were previously available. This new information about genes and their functions will speed along basic biological understanding and present many new targets for therapeutic intervention. In some cases analytical tools have not kept pace with the generation of new data. An example is provided by recent advances in the measurement of global differential gene expression. These methods, typified by gene expression microarrays, differential cDNA cloning frequencies, subtractive hybridization and differential display methods, can very rapidly identify genes that are up or down-regulated in different tissues or in response to specific stimuli. Increasingly, such methods are being used to explore biological processes such as, transformation, tumor progression, the inflammatory response, neurological disorders etc. One can now very easily generate long lists of differentially expressed genes that correlate with a given physiological phenomenon, but demonstrating a causative relationship between an individual differentially expressed gene and the phenomenon is difficult. Until now, simple methods for assigning function to differentially expressed genes have not kept pace with the ability to monitor differential gene expression.

Using conventional molecular approaches, over expression of a candidate gene can be accomplished by cloning a full-length cDNA, subcloning it into a mammalian expression vector and transfecting the recombinant vector into an appropriate host cell. This approach is straightforward but labor intensive, particularly when the initial candidate gene is represented by a simple expressed sequence tag (EST). Under expression of a candidate gene by "conventional" methods is yet more problematic. Antisense methods and methods that rely on targeted ribozymes are unreliable, succeeding for only a small fraction of the targets selected. Gene knockout by homologous recombination works fairly well in recombinogenic stem cells but very inefficiently in somatically derived cell lines. In either case large clones of syngeneic genomic DNA (on the order of 10 kb) should be isolated for recombination to work efficiently.

The TALE-fusion technology can be used to rapidly analyze differential gene expression studies. Engineered TALE domain fusions can be readily used to up or down-regulate any endogenous target gene. Very little sequence information is required to create a gene-specific DNA binding domain. This makes the TALE domain fusions technology ideal for analysis of long lists of poorly characterized differentially expressed genes. One can simply build a TALE-based DNA-binding domain for each candidate gene, create chimeric up and down-regulating artificial transcription factors and test the consequence of up or down-regulation on the phenotype under study (transformation, response to a cytokine etc.) by switching the candidate genes on or off one at a time in a model system.

This specific example of using engineered TALE domain fusions to add functional information to genomic data is merely illustrative. Any experimental situation that could benefit from the specific up or down-regulation of a gene or genes could benefit from the reliability and ease of use of engineered TALE-fusions.

Additionally, greater experimental control can be imparted by TALE domain fusions than can be achieved by more conventional methods. This is because the production and/or function of engineered TALE-fusions can be placed under small molecule control. Examples of this approach are provided by the Tet-On system, the ecdysone-regulated system and a system incorporating a chimeric factor including a mutant progesterone receptor. These systems are all capable of indirectly imparting small molecule control on any endogenous gene of interest or any transgene by placing the function and/or expression of a ZFP regulator under small molecule control.

Transgenic Organisms

A further application of the TALE-fusion technology is manipulating gene expression and/or altering the genome to produce transgenic animals or plants. As with cell lines, over-expression of an endogenous gene or the introduction of a heterologous gene to a transgenic animal, such as a transgenic mouse, is a fairly straightforward process. Similarly, production of transgenic plants is well known. The TALE domain fusions technology described herein can be used to readily generate transgenic animals and plants.

The use of engineered TALE domain fusions to manipulate gene expression can be restricted to adult animals using the small molecule regulated systems described in the previous section. Expression and/or function of a TALE domain-based repressor can be switched off during development and switched on at will in the adult animals. This approach relies on the addition of the TALE-fusions expressing module only; homologous recombination is not required. Because the TALE domain fusions repressors are trans dominant, there is no concern about germline transmission or homozygosity. These issues dramatically affect the time and labor required to go from a poorly characterized gene candidate (a cDNA or EST clone) to a mouse model. This ability can be used to rapidly identify and/or validate gene targets for therapeutic intervention, generate novel model systems and permit the analysis of complex physiological phenomena (development, hematopoiesis, transformation, neural function etc.). Chimeric targeted mice can be derived according to Hogan et al., Manipulating the Mouse Embryo:

A Laboratory Manual, (1988); Teratocarcinomas and Embryonic Stem Cells: A Practical Approach, Robertson, ed., (1987); and Capecchi et al., *Science* 244:1288 (1989).

Genetically modified animals may be generated by deliver of the nucleic acid encoding the TALE fusion into a cell or an embryo. Typically, the embryo is a fertilized one cell stage embryo. Delivery of the nucleic acid may be by any of the methods known in the art including micro injection into the nucleus or cytoplasm of the embryo. TALE fusion encoding nucleic acids may be co-delivered with donor nucleic acids as desired. The embryos are then cultured as in known in the art to develop a genetically modified animal.

In one aspect of the invention, genetically modified animals in which at least one chromosomal sequence encoding a gene or locus of interest has been edited are provided. For example, the edited gene may become inactivated such that it is not transcribed or properly translated. Alternatively, the sequence may be edited such that an alternate form of the gene is expressed (e.g. insertion (knock in) or deletion (knock out) of one or more amino acids in the expressed protein). In addition, the gene of interest may comprise an inserted sequence such as a regulatory region. The genetically modified animal may be homozygous for the edited sequence or may be heterozygous. In some embodiments, the genetically modified animal may have sequence inserted (knocked in) in a 'safe harbor' locus such as the Rosa26, HPRT, CCR5 or AAVS1 (PPP1R12C) loci. These knock in animals may be additionally edited at other chromosomal loci. In some embodiments, the sequences of interest are inserted into the safe harbor without any selection markers, and/or without a promoter and so rely on the endogenous promoter to drive expression. In some aspects, the genetically modified animal may be "humanized" such that certain genes specific to the host species animal are replaced with the human homolog. In this way, genetically modified animals are produced with a human gene expressed (e.g. Factor IX) to allow for the development of an animal model system to study the human gene, protein or disease. In some embodiments, the gene of interest may further comprise a recombinase recognition site such as loxP or FRT for recognition of the cognate recombinase Cre and FLP, respectively, which can flank the inserted gene(s) of interest. Genes may be inserted containing the nuclease sites such that crossing the genetically modified animal with another genetically modified animal expressing the cognate recombinase (e.g. Cre) will result in progeny that lack the inserted gene.

Applications

The disclosed methods and compositions find use, for example, in increasing the specificity and/or activity of TALE proteins and TALE fusion proteins Enhancement of the activity of a TALE protein increases its applicability to use in a variety of settings. Activity may be increased by (i) modification of the cleavage domain, for example to have a faster cleavage rate; (ii) an increase in binding specificity, for example a stronger bond between TALEN and target site so that association of one or more of the nucleases with the target occurs more quickly or lasts longer, allowing more time for the cleavage to occur; (iii) modification (design) of the DNA binding domains, for example by use of multiple (e.g., 3, 4, 5, 6, 7, 8, 9, 10 or more) non-canonical or atypical RVDs, alteration of position 11 of one or more repeat units, development of more robust and active R0-R1 pairs and/or by developing R1/2 repeats that are able to interact with more targets. It will be apparent that increased activity of the TALE fusions means that less nuclease expression vector needs to be introduced into a cell, which is useful for example in cell types that are typically difficult to transfect or transduce (such as primary cells or stem cells) and/or in large pool of cells.

The increased specificity provided by the methods and compositions described herein is also helpful in many settings as well. In many applications (e.g., therapeutic or agricultural settings), it is important for cleavage by an engineered nuclease to occur only at the desired locus, and to not have any off-target cutting as this may lead to unintended damage of non-targeted genes and potentially adverse effects, such as a removal of growth control of a cell. Likewise, increased specificity of an engineered transcription factor provides tighter regulation where only the desired gene is turned on or off. Specificity can be increased, for example, by identification of DNA binding domains that are more likely to recognize only their cognate and targeted sequences without recognizing other even closely related targets. In agricultural settings, increased specificity of engineered nucleases means that desired outcomes such as trait stacking could be more easily achieved since the nuclease could be designed to only cleave at one specific location, and not at any other related sequences. Plants have much larger genomes that mammalian cells (10-100×) and often have more duplicated genes and multi-gene families. Thus, increasing the specificity of a nuclease will allow the protein to distinguish between these various gene copies with more accuracy.

Utility can also be enhanced by increasing the ability of the TALE proteins to recognize more targets. Currently, most TALE proteins preferentially recognize a "T" nucleotide base at both the 5' and 3' ends of the target sequence. Thus, when designing TALE proteins, a useable site (with terminal Ts) typically must be found and used. The ability to engineer a TALE DNA binding domain to either specifically recognize an A, C, T or G, or to bind DNA, yet be neutral about the nucleotide on the 5' or 3' ends of the target sequence greatly expands the repertoire of targets for TALE proteins.

Thus, the methods and compositions of the invention are used to enhance the activity and/or specificity of TALE proteins useful for genome modification.

EXAMPLES

Example 1

Identification of Multimer RVDs with Enhanced Activity

Figure 2:
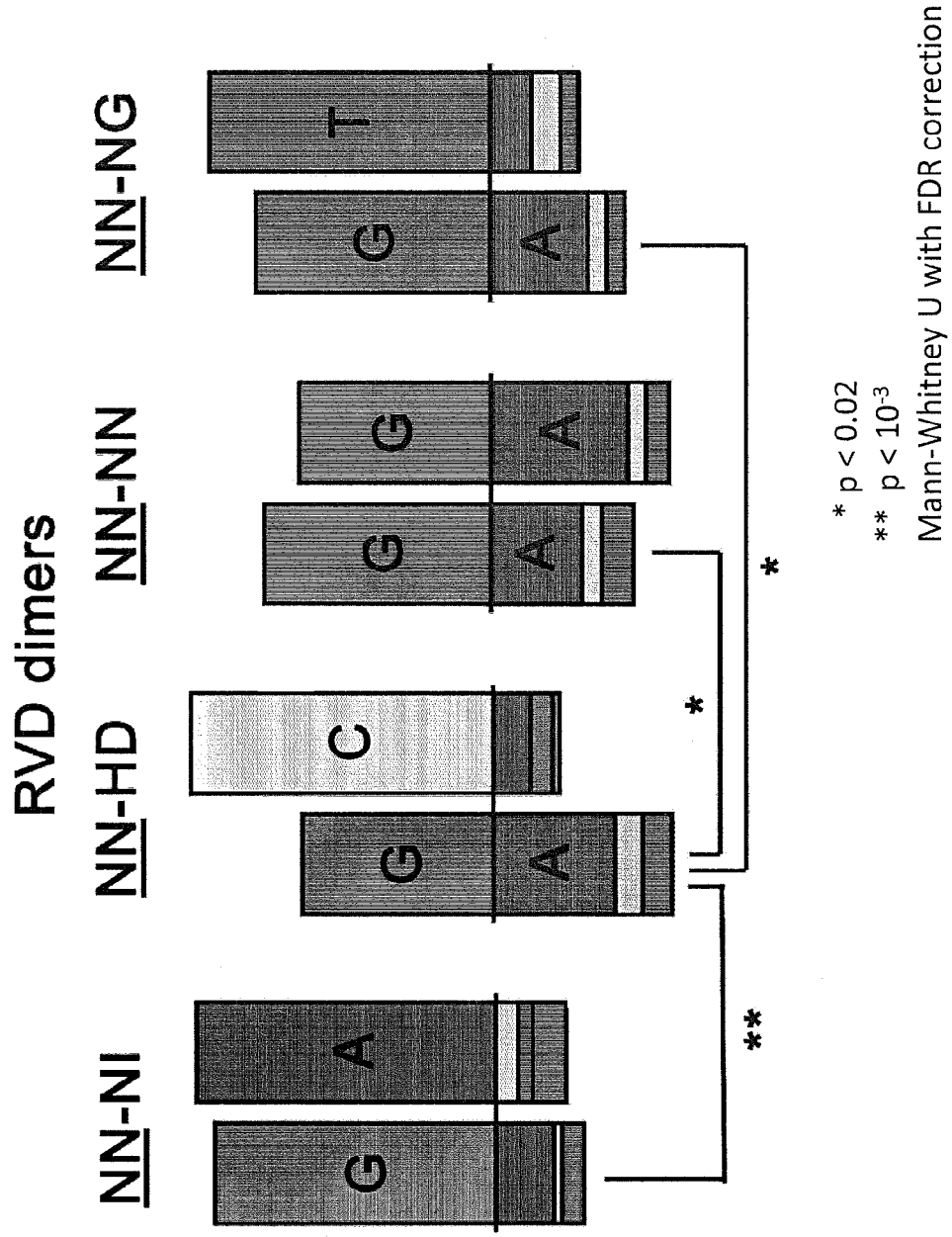
FIG. 2 shows mathematical analysis of base preference of the 'NN' RVD with different neighbors. Base specificity of pairs of repeat units within larger TALEN DNA binding domains were analyzed for NN specificity according to neighbor. The data indicates that the variance of NN specificity is statistically significant from one dimer to another.

Several engineered TALENs were constructed using the canonical RVDs for target base recognition, and we found that the position of the RVD within the repeat array influenced its base preference. By way of example, a SELEX analysis of TALEN SBS101146 (see co-owned US Patent Publication 20110301073 for methodology and see below in Table 1) found that the RVD "NN", which typically recognizes G, showed more or less selectivity for G depending on where the NN-containing repeat unit was in the array (FIG. 1). A numerical comparison of the base preference for NN showed that these neighbor effects can be significant (FIG. 2). Additional examples of the variable behavior of the NN and NG RVDs were demonstrated (FIG. 3) using a number of the engineered TALENs shown below in Table 1. This type of data indicated that TALE repeat units are influenced by their surroundings, and the variant binding behavior can potentially have an effect on the specificity and affinity of the TALEN for its target. Therefore, we sought to develop more robust RVDs.

plished by using DNA fragments encoding TALE monomers for each position that have single-stranded DNA overhangs that only allow them to ligate together in the intended

TABLE 1

Engineered TALENs

| SBS Target number | Target gene | Target sequence 5'-3' | RVD sequences (N->C) |
|---|---|---|---|
| 101146 | hPITX3 | gtCAGACGCTGGCACTcc (SEQ ID NO: 91) | HD-NI-NN-NI-HD-NN-HD-NG-NN-NN-HD-NI-HD-NG (SEQ ID NO: 98) |
| 101082 | cgFUT8 | gtGTATCTGGCCACTGATga (SEQ ID NO: 92) | NN-NG-NI-NG-HD-NG-NN-NN-HD-HD-NI-HD-NG-NN-NI-NG (SEQ ID NO: 99) |
| 101089 | EGFP | ctGAAGGGCATCGACTtc (SEQ ID NO: 93) | NN-NI-NI-NN-NN-NN-HD-NI-NG-HD-NN-NI-HD-NG (SEQ ID NO: 100) |
| 101051 | hCXCR4 | ctGAGCCCATTTCCTcg (SEQ ID NO: 94) | NN-NI-NN-HD-HD-HD-NI-NG-NG-NG-HD-HD-NG (SEQ ID NO: 101) |
| 101034 | hCCR5 | ctCTTCAGCCTTTTGCAGTtt (SEQ ID NO: 95) | HD-NG-NG-HD-NI-NN-HD-HD-NG-NG-NG-NG-NN-HD-NI-NN-NG (SEQ ID NO: 102) |
| 101041 | hCCR5 | ctTCATTACACCTGCAGCTct (SEQ ID NO: 96) | NG-HD-NI-NG-NG-NI-HD-NI-HD-HD-NG-NN-HD-NI-NN-HD-NG (SEQ ID NO: 103) |
| 102204 | hCCR5 | ctTCATTACACCTGCAGCTct (SEQ ID NO: 96) | QG-ND-HI-KG-VA-CI-ND-HI-KD-KD-QG-HN-RD-HI-HN-ND-NG (SEQ ID NO: 104) |
| 101047 | hCCR5 | ttCTTCCAGAATTGATACTga (SEQ ID NO: 97) | HD-NG-NG-HD-HD-NI-NN-NI-NI-NG-NG-NN-NI-NG-NI-HD-NG (SEQ ID NO: 105) |
| 102109 | hCCR5 | ttCTTCCAGAATTGATACTga (SEQ ID NO: 97) | RD-AA-QG-AD-KD-HI-AN-KI-KI-RG-RG-FN-CI-KG-HI-AD-KG (SEQ ID NO: 106) |

Our strategy for constructing new TALE proteins relies on the use of TALE repeat tetramers as the fundamental unit of assembly and design. Therefore, as our initial step towards the generation of TALE fusion proteins with improved activity and specificity, we sought to first develop component tetramers that exhibited improved binding to their cognate 4-bp target sequences. To accomplish this, we assembled a tetramer library specific for each 4-bp subsite within the "L538" and "R557" target sequences (FIG. 4A), in which several alternative RVDs were used for recognition of each possible base. We then screened randomly chosen constructs via ELISA to identify those tetramers exhibiting the highest affinity for the relevant DNA target site. We chose this approach to allow the use of a variety of RVDs for base recognition (in contrast to natural TALEs, which predominantly use just one RVD for binding each base type) and to allow the construction of TALE fusion proteins that accommodate context dependent interaction between neighboring repeat units and results in proteins with superior activity.

Tetramer Library Construction

TALE tetramer libraries were constructed using a subset of all the possible 400 RVDs as follows: For recognition of an adenine, A, in the target DNA, repeat units with HI, CI, or KI RVDs were chosen. For C, repeat units with ND, AD, KD and RD were used, while for G, the KN, EN, HN, SN, AN, CN, GN, FN, AK and CK RVD containing repeat units were utilized. For recognition of T, repeat units with HG, KG, MG, QG, RG, AA, QA and VA RVDs were used.

Figure 4A:
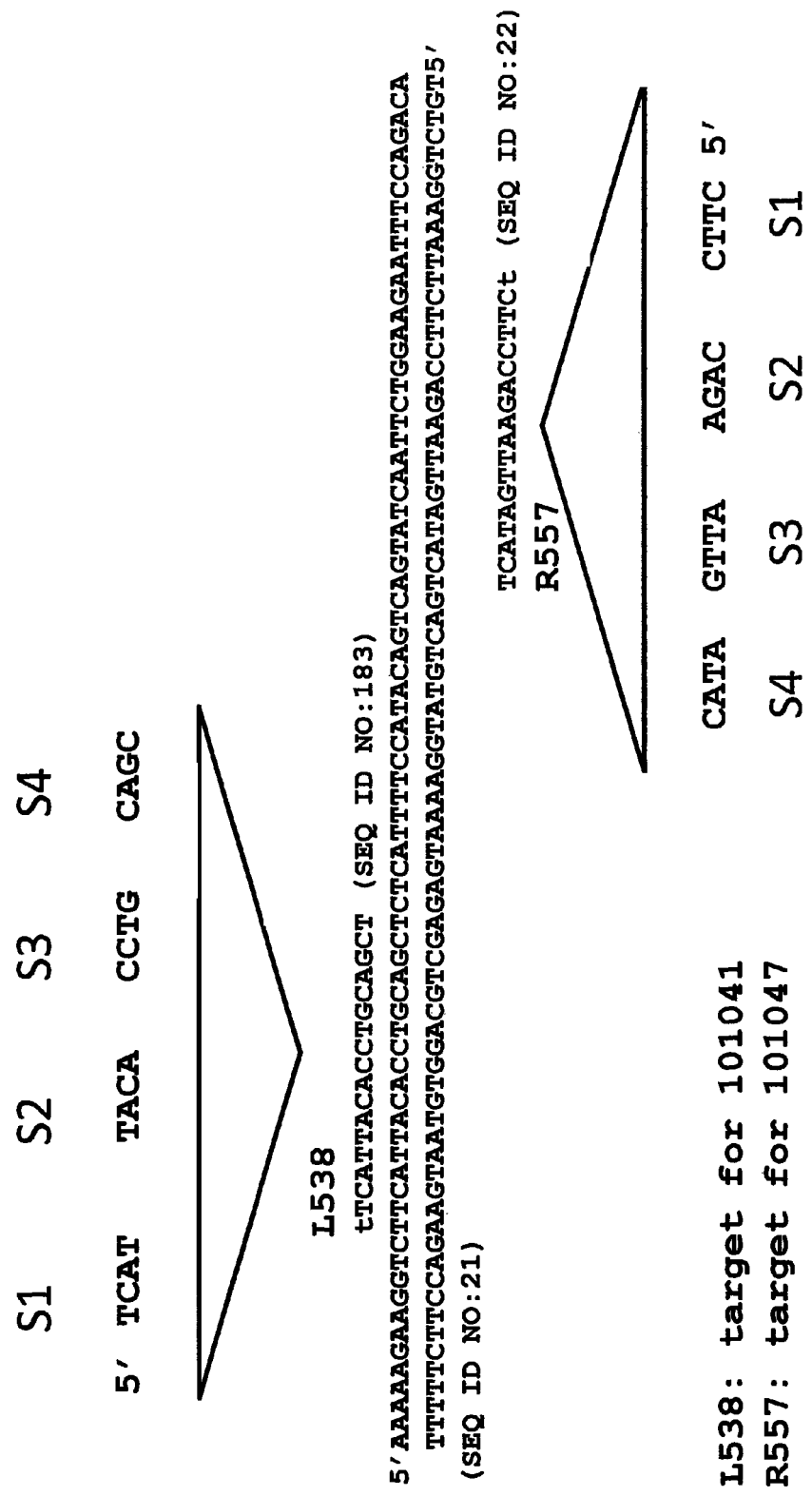
FIG. 4A depicts the DNA sequence of the CCR5 gene and the target sites for the two TALENs proteins, 101041 and 101047, used for modification of CCR5 (the "L538" and "R557" targets, respectively). Above or below each binding site is the sequence of its four component DNA 4-bp subsites targeted in this study (labeled S1 to S4). The 16 bases of the target sites for 101041 and 101047 comprised of these 4-bp DNA sites are underlined. In addition to the four component tetramers, each site contains an additional 5' T and 3' T. The non-underlined lowercase T at the 5' of each binding site is specified by the TALE N-cap while the non-underlined uppercase T at the 3' end of each binding site is specified by the NG RVD in the C-terminal half repeat of each TALEN.
Figure 4B:
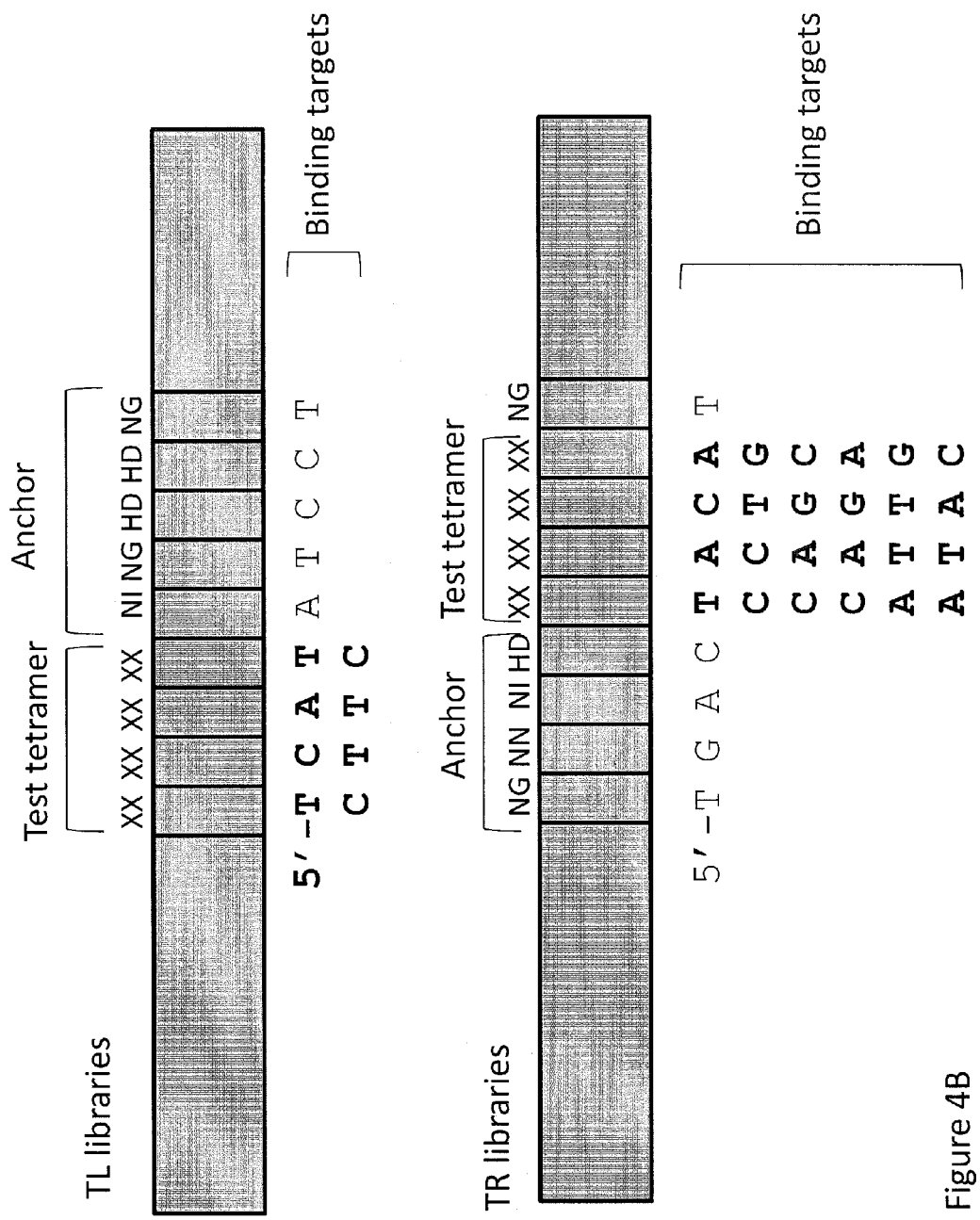
FIG. 4B is an overview of the library TALEs used for ELISA studies. Tetramer libraries specific for each of the 4 bp subsites indicated in panel 4A were linked to the invariant "anchor" tetramers as shown and depicts the location of the anchor portions of the library proteins. RVDs labeled as 'XX' were mixtures of RVDs capable of specifying the cognate base of the 4-bp DNA site being targeted. Libraries were created in the TL context for each of the 4-bp DNA sites TCAT and CTTC and in the "TR" context for the remaining 4 bp subsites. In this experiment, a mixture of HI, CI, and KI RVDs was used when targeting an A, a mixture of ND, AD, KD, and RD were used when targeting a C, a mixture of KN, EN, HN, SN, AN, CN, GN, FN, AK and CK RVDs was used when targeting a G, and a mixture of HG, KG, MG, QG, RG, AA, QA and VA RVDs was used when targeting a T. A number of individual clones from each shotgun library were screened for binding to a double-stranded DNA target site comprising the targeted 4-bp DNA site and the appropriate adjacent bases bound by the anchor TALE tetramer. Tetramer clones with the best binding properties were combined to created TALENs capable of enhanced targeting of the binding sites of TALENs 101041 (target site shown in SEQ ID NO:96) and 10147 (target site shown in SEQ ID NO:97).

Eight sequence-specific tetramer libraries were constructed (one for each of the 4 bp subsites highlighted in FIG. 4A). In each library, an RVD mixture was chosen for each repeat position (i.e., as the first, second, third or fourth repeat) that matched the targeted base. This was accomplished by using DNA fragments encoding TALE monomers for each position that have single-stranded DNA overhangs that only allow them to ligate together in the intended positions within the four repeat block. For example, for the 4 bp target TCAT in the L538 target, sequences encoding monomers intended to recognize T at the 5' end of the TCAT will encode RVD candidates that recognize T (e.g. HG, KG, MG, QG, RG, AA, QA and VA) and have single-stranded DNA overhangs designed to ligate only in position 1 of the four repeat block. Similarly, DNA fragments encoding monomers intended to target C (e.g. ND, AD, KD and RD) and have single-stranded DNA overhangs designed to ligate only in position 2 of the four repeat block, DNA fragments encoding monomers intended to target A in the TCAT encode RVD candidates that recognize A (e.g. HI, CI, or KI) have single-stranded DNA overhangs designed to ligate only in position 3 of the four repeat block, and DNA fragments encoding monomers intended to target the 3' T of TCAT (e.g. HG, KG, MG, QG, RG, AA, QA and VA) have single-stranded DNA overhangs designed to ligate only in position 4 of the four repeat block. These four mixtures of monomers are then ligated together in the proper order followed by ligation into the vector shown as TL library in FIG. 4B. The remaining seven of the tetramer libraries are assembled using a similar scheme except that six of them (targeting the 4 bp sequences TACA, CCTG, CAGC, CAGA, ATTG, and ATAC) are ligated into the vector shown as TR library in FIG. 4B.

Once the tetramer library had been constructed and screened, constructs that bind each 4-bp target site well were then used to build TALENs specific for the human CCR5 gene (see Stephens J C et al, (1998) *Am J Hum Gen* 62(6): 1507-15). The region in the CCR5 gene and the specific target sites for the TALENs are shown below, including the 101041 TALEN target site (SEQ ID NO:20); the double-stranded substrate (SEQ ID NO:21) and the 101047 TALEN target site (SEQ ID NO:22):

```
101041          5'TCATTACACCTGCAGCT
5'AAAAAGAAGGTCTTCATTACACCTGCAGCTCTCATTTTCCATACAGTCAGTATCAATTCTGGAAGAATTTCCAGACATT
  TTTTTCTTCCAGAAGTAATGTGGACGTCGAGAGTAAAAGGTATGTCAGTCATAGTTAAGACCTTCTTAAAGGTCTGTAA5'
101047                                              TCATAGTTAAGACCTTC 5'
```

Figure 5:
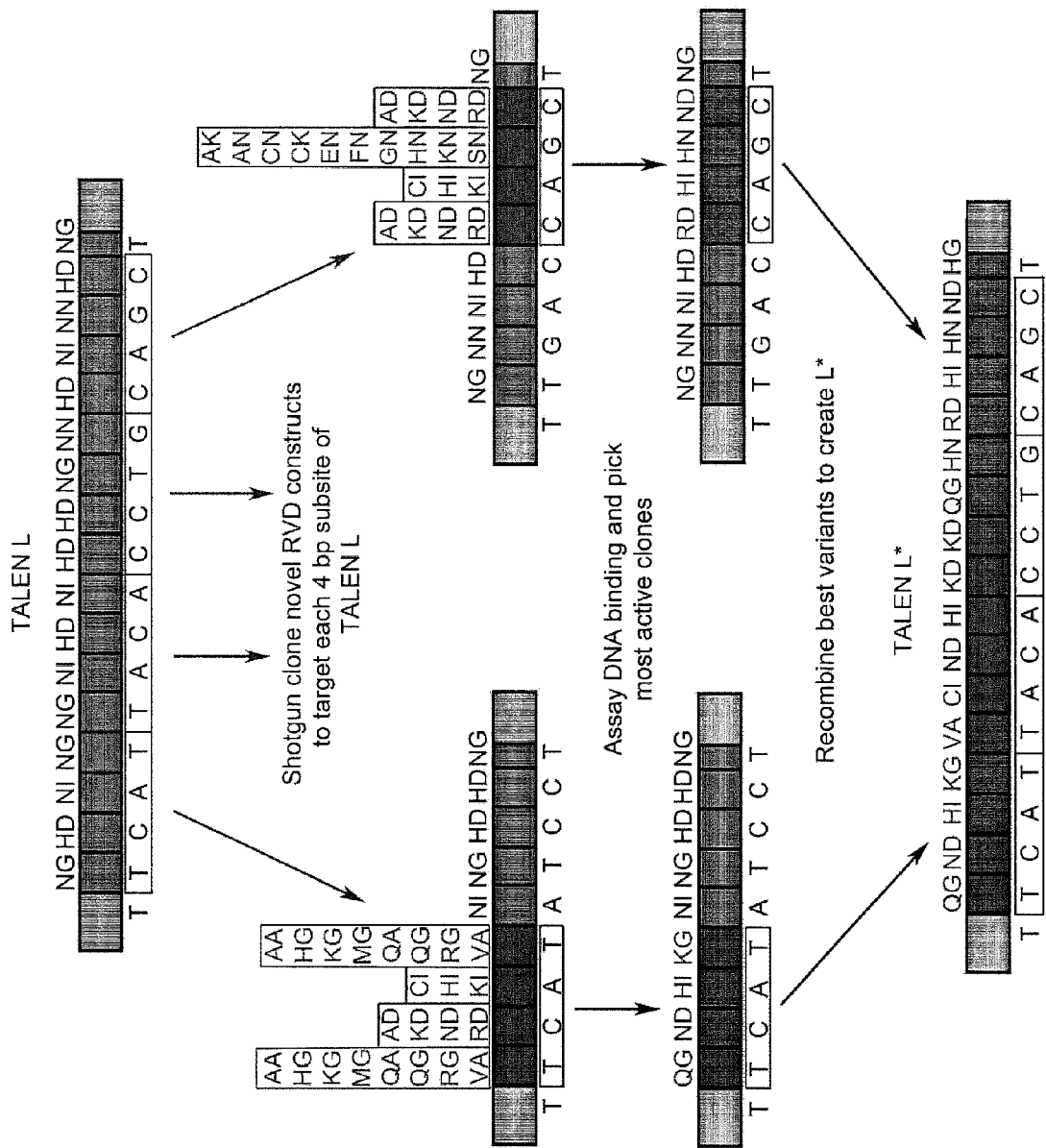
FIG. 5 is a diagrammatic depiction of the process used to design a TALEN 'L*' (SBS 102204) comprising all non-canonical RVDs which bind the same target sequence as TALEN (SBS101041).

An overview diagram of this process is shown in FIG. 5. TALENs that bind the L538 and R557 targets were built as described previously (see co-owned U.S. Patent Publication No. 20110301073). Thus for the TALENs that bind these two sites, the tetramer building blocks were derived in the library as shown below where the complexity at each tetramer is shown below the 4 bp DNA target:

```
L538 target:  TCAT TACA CCTG CAGC T
Complexity:    768  288 1280  480

R557 target:  CTTC CAGA ATTG ATAC T
Complexity:   1024  360 1920  288
```

Library complexity for any given tetramer is based upon how many RVDs were possible for a given base. For example, a library made for a 4 bp DNA target containing a G includes members with 10 potential RVDs just for the G position, and also includes all the potential RVDs for each of the other three bases in all possible combinations.

Analysis of Tetramer Binding

To test the ability of the candidate tetramers to bind to their targets, they were assembled into two libraries. The TL library contained TALEs with a mixture of tetramers linked to the N-terminal side of the anchor of five repeat units with canonical (typical) RVDs NI-NG-HD-HD-NG specifying an ATCCT target. In the TL library, two sets of tetramer libraries were constructed, one in which the tetramer library targeted the TCAT target, and one where the tetramer library targeted the CTTC target. The TR library was constructed such that the tetramer mixtures were linked to the C-terminus of the anchor TALE repeats specifying a TGAC target where the anchor was again specified by the canonical RVDs (NG-NN-NI-HD in this example. The TR library also contained an additional anchor RVD (NG), encoded in the portion of the vector encoding the half repeat in the TALE C-cap. The tetramers tested in this library were intended to bind to TCAT, CCTG, CAGC, CAGA, ATTG, and ATAC (FIG. 4A). Both the TL and TR constructs used the TALEN backbone described previously (N+137 N cap, N+63 C cap, see co-owned U.S. Patent Publication 20110301073).

The proteins were then assembled, made with in vitro transcription and translation (TNT) kit (Promega) and tested for binding to the target oligonucleotides by ELISA. The results are shown in Table 2 below:

TABLE 2

ELISA results from tetramer shotgun cloning

| Library Target | RVDs at each position | | | | AFU | Norm |
|---|---|---|---|---|---|---|
| | 1 | 2 | 3 | 4 | | |
| TL_TCAT | QG | KD | KI | AA | 477 | 2.34 |
| TL_TCAT | QG | AD | HI | KG | 460 | 2.26 |
| TL_TCAT | HG | RD | HI | HG | 427 | 2.09 |
| TL_TCAT | QG | ND | KI | RG | 410 | 2.01 |
| TL_TCAT | RG | ND | KI | HG | 395 | 1.94 |
| TL_TCAT | RG | RD | HI | AA | 315 | 1.54 |
| TL_TCAT | KG | AD | CI | HG | 304 | 1.49 |
| TL_TCAT | KG | ND | KI | QA | 278 | 1.36 |
| TL_TCAT | KG | KD | KI | VA | 267 | 1.31 |
| TL_TCAT | QG | RD | HI | QG | 232 | 1.14 |

TABLE 2-continued

ELISA results from tetramer shotgun cloning

| Library Target | RVDs at each position | | | | AFU | Norm |
|---|---|---|---|---|---|---|
| | 1 | 2 | 3 | 4 | | |
| TL_TCAT | RG | ND | KI | QA | 212 | 1.04 |
| TL_TCAT | QG | ND | HI | KG | 169 | 0.83 |
| TL_TCAT | VA | RD | KI | HG | 164 | 0.80 |
| TL_TCAT | VA | KD | HI | RG | 145 | 0.71 |
| TL_TCAT | RG | KD | KI | KG | 117 | 0.57 |
| TL_TCAT | HG | KD | KI | MG | 97 | 0.48 |
| TL_TCAT | HG | AD | CI | QG | 95 | 0.46 |
| TL_TCAT | VA | ND | HI | HG | 44 | 0.22 |
| TL_TCAT | QG | RD | CI | QG | 36 | 0.18 |
| TL_TCAT | RG | ND | CI | MG | 35 | 0.17 |
| TL_TCAT | VA | KD | CI | RG | 28 | 0.14 |
| TL_TCAT | KG | KD | CI | AA | 20 | 0.10 |
| TL_TCAT | AA | KD | KI | MG | 11 | 0.05 |
| *TL_TCAT* | *NG* | *HD* | *NI* | *NG* | *204* | *1.00* |
| TR_TACA | RG | HI | RD | KI | 1265 | 1.62 |
| TR_TACA | VA | CI | ND | HI | 1226 | 1.57 |
| TR_TACA | HG | HI | ND | HI | 1166 | 1.50 |
| TR_TACA | VA | HI | ND | KI | 1077 | 1.38 |
| TR_TACA | RG | CI | ND | HI | 1010 | 1.30 |
| TR_TACA | HG | HI | RD | HI | 968 | 1.24 |
| TR_TACA | KG | HI | KD | HI | 910 | 1.17 |
| TR_TACA | VA | HI | RD | HI | 887 | 1.14 |
| TR_TACA | AA | HI | RD | KI | 859 | 1.10 |
| TR_TACA | KG | CI | ND | KI | 771 | 0.99 |
| TR_TACA | KG | HI | ND | HI | 722 | 0.93 |
| TR_TACA | AA | HI | KD | KI | 717 | 0.92 |
| TR_TACA | KG | CI | KD | HI | 669 | 0.86 |
| TR_TACA | RG | KI | AD | HI | 647 | 0.83 |
| TR_TACA | RG | KI | ND | KI | 638 | 0.82 |
| TR_TACA | QA | HI | AD | HI | 589 | 0.76 |
| TR_TACA | KG | HI | RD | CI | 555 | 0.71 |
| TR_TACA | HG | KI | KD | KI | 551 | 0.71 |
| TR_TACA | KG | KI | KD | KI | 503 | 0.65 |
| TR_TACA | VA | KI | RD | HI | 503 | 0.65 |
| TR_TACA | VA | KI | KD | KI | 429 | 0.55 |
| TR_TACA | AA | HI | AD | HI | 380 | 0.49 |
| TR_TACA | KG | KI | KD | CI | 370 | 0.48 |
| *TR_TACA* | *NG* | *NI* | *HD* | *NI* | *779* | *1.00* |
| TR_CCTG | AD | RD | HG | HN | 1331 | 1.30 |
| TR_CCTG | ND | KD | HG | HN | 1089 | 1.07 |
| TR_CCTG | ND | ND | QA | HN | 868 | 0.85 |
| TR_CCTG | ND | ND | HG | KN | 855 | 0.84 |
| TR_CCTG | ND | KD | RG | HN | 853 | 0.84 |
| TR_CCTG | ND | KD | KG | HN | 807 | 0.79 |
| TR_CCTG | KD | KD | QG | HN | 712 | 0.70 |
| TR_CCTG | RD | RD | KG | HN | 683 | 0.67 |
| TR_CCTG | KD | KD | QA | HN | 555 | 0.54 |
| TR_CCTG | ND | RD | VA | HN | 551 | 0.54 |
| TR_CCTG | AD | ND | AA | HN | 365 | 0.36 |
| TR_CCTG | RD | ND | KG | KN | 326 | 0.32 |
| TR_CCTG | ND | RD | KG | CN | 312 | 0.31 |
| TR_CCTG | AD | KD | QA | HN | 277 | 0.27 |
| TR_CCTG | KD | ND | QG | HN | 197 | 0.19 |
| TR_CCTG | KD | KD | KG | CN | 135 | 0.13 |
| TR_CCTG | ND | AD | KG | HN | 116 | 0.11 |
| TR_CCTG | KD | ND | KG | CK | 53 | 0.05 |
| TR_CCTG | KD | ND | AA | FN | 34 | 0.03 |
| TR_CCTG | KD | ND | HG | CK | 29 | 0.03 |
| TR_CCTG | ND | KD | KG | CK | 28 | 0.03 |
| TR_CCTG | AD | KD | RG | CN | 25 | 0.02 |
| TR_CCTG | RD | ND | AA | HN | 24 | 0.02 |
| *TR_CCTG* | *HD* | *HD* | *NG* | *NN* | *1020* | *1.00* |
| TR_CAGC | RD | HI | HN | ND | 987 | 1.52 |
| TR_CAGC | RD | HI | GN | ND | 261 | 0.40 |
| TR_CAGC | KD | HI | CK | ND | 69 | 0.11 |
| TR_CAGC | AD | HI | HN | RD | 44 | 0.07 |

TABLE 2-continued

ELISA results from tetramer shotgun cloning

| Library Target | RVDs at each position | | | | AFU | Norm |
|---|---|---|---|---|---|---|
| | 1 | 2 | 3 | 4 | | |
| TR_CAGC | AD | HI | AN | ND | 37 | 0.06 |
| TR_CAGC | KD | KI | CN | ND | 26 | 0.04 |
| TR_CAGC | KD | KI | CK | ND | 25 | 0.04 |
| TR_CAGC | ND | KI | KN | ND | 16 | 0.03 |
| TR_CAGC | ND | KI | KN | ND | 15 | 0.02 |
| TR_CAGC | KD | HI | AN | RD | 14 | 0.02 |
| TR_CAGC | RD | KI | SN | KD | 14 | 0.02 |
| TR_CAGC | KD | HI | AK | ND | 13 | 0.02 |
| TR_CAGC | KD | HI | CN | KD | 12 | 0.02 |
| TR_CAGC | AD | HI | CK | ND | 12 | 0.02 |
| TR_CAGC | RD | KI | CK | RD | 4 | 0.01 |
| TR_CAGC | RD | KI | AK | KD | 4 | 0.01 |
| TR_CAGC | AD | HI | SN | KD | 3 | 0.00 |
| TR_CAGC | KD | HI | GN | RD | 2 | 0.00 |
| TR_CAGC | AD | HI | SN | RD | 1 | 0.00 |
| TR_CAGC | ND | KI | FN | AD | 0 | 0.00 |
| TR_CAGC | KD | CI | AN | KD | −1 | 0.00 |
| *TR_CAGC* | *HD* | *NI* | *NN* | *HD* | *649* | *1.00* |
| TL_CTTC | RD | RG | RG | KD | 241 | 13.76 |
| TL_CTTC | RD | RG | KG | AD | 144 | 8.22 |
| TL_CTTC | RD | HG | KG | ND | 128 | 7.32 |
| TL_CTTC | ND | HG | RG | ND | 127 | 7.27 |
| TL_CTTC | ND | KG | HG | ND | 110 | 6.29 |
| TL_CTTC | RD | RG | KG | ND | 103 | 5.90 |
| TL_CTTC | ND | KG | HG | KD | 90 | 5.12 |
| TL_CTTC | KD | QG | HG | RD | 87 | 4.99 |
| TL_CTTC | KD | QG | HG | ND | 82 | 4.66 |
| TL_CTTC | ND | AA | RG | AD | 74 | 4.23 |
| TL_CTTC | RD | HG | RG | KD | 69 | 3.95 |
| TL_CTTC | ND | RG | KG | ND | 65 | 3.72 |
| TL_CTTC | ND | AA | QG | ND | 48 | 2.74 |
| TL_CTTC | KD | AA | QG | ND | 47 | 2.70 |
| TL_CTTC | RD | HG | RG | ND | 41 | 2.36 |
| TL_CTTC | ND | KG | AA | ND | 39 | 2.23 |
| TL_CTTC | RD | MG | KG | ND | 32 | 1.80 |
| TL_CTTC | RD | VA | RG | RD | 25 | 1.41 |
| TL_CTTC | RD | AA | QG | AD | 23 | 1.30 |
| TL_CTTC | RD | AA | HG | RD | 19 | 1.11 |
| TL_CTTC | ND | VA | KG | RD | 18 | 1.01 |
| TL_CTTC | KD | QA | HG | RD | 15 | 0.84 |
| TL_CTTC | RD | RG | MG | ND | 3 | 0.16 |
| TR_CAGA | KD | HI | HN | KI | 1280 | 1.33 |
| TR_CAGA | KD | HI | FN | HI | 1251 | 1.30 |
| TR_CAGA | ND | HI | HN | KI | 1234 | 1.28 |
| TR_CAGA | KD | HI | KN | CI | 1013 | 1.05 |
| TR_CAGA | RD | HI | HN | HI | 895 | 0.93 |
| TR_CAGA | AD | KI | HN | HI | 850 | 0.88 |
| TR_CAGA | KD | CI | HN | HI | 800 | 0.83 |
| TR_CAGA | KD | KI | KN | HI | 738 | 0.77 |
| TR_CAGA | KD | HI | AN | KI | 681 | 0.71 |
| TR_CAGA | RD | HI | SN | KI | 560 | 0.58 |
| TR_CAGA | ND | KI | KN | HI | 532 | 0.55 |
| TR_CAGA | RD | KI | HN | KI | 397 | 0.41 |
| TR_CAGA | ND | KI | FN | HI | 352 | 0.37 |
| TR_CAGA | RD | HI | EN | HI | 331 | 0.34 |
| TR_CAGA | KD | HI | AN | CI | 322 | 0.33 |
| TR_CAGA | KD | HI | SN | KI | 315 | 0.33 |
| TR_CAGA | RD | CI | HN | KI | 242 | 0.25 |
| TR_CAGA | ND | HI | CN | KI | 183 | 0.19 |
| TR_CAGA | RD | CI | HN | CI | 136 | 0.14 |
| TR_CAGA | RD | HI | CN | CI | 83 | 0.09 |
| TR_CAGA | RD | KI | AN | KI | 66 | 0.07 |
| TR_CAGA | AD | HI | GN | HI | 38 | 0.04 |
| TR_ATTG | CI | MG | KG | HN | 1187 | 1.22 |
| TR_ATTG | CI | KG | QG | HN | 1085 | 1.12 |
| TR_ATTG | CI | KG | MG | HN | 1050 | 1.08 |
| TR_ATTG | KI | HG | QA | HN | 976 | 1.00 |
| TR_ATTG | HI | AA | VA | HN | 965 | 0.99 |
| TR_ATTG | CI | HG | HG | CN | 845 | 0.87 |
| TR_ATTG | CI | KG | AA | HN | 774 | 0.80 |
| TR_ATTG | KI | RG | QG | AN | 674 | 0.69 |
| TR_ATTG | KI | KG | MG | AN | 595 | 0.61 |
| TR_ATTG | KI | RG | KG | EN | 592 | 0.61 |
| TR_ATTG | KI | MG | HG | HN | 591 | 0.61 |
| TR_ATTG | CI | HG | RG | KN | 545 | 0.56 |
| TR_ATTG | KI | RG | RG | FN | 396 | 0.41 |
| TR_ATTG | HI | KG | VA | AK | 385 | 0.40 |
| TR_ATTG | KI | KG | HG | CK | 352 | 0.36 |
| TR_ATTG | HI | KG | QA | SN | 327 | 0.34 |
| TR_ATTG | HI | AA | RG | GN | 171 | 0.18 |
| TR_ATTG | KI | QG | VA | CN | 161 | 0.17 |
| TR_ATTG | HI | QA | RG | GN | 152 | 0.16 |
| TR_ATTG | KI | QA | MG | AN | 136 | 0.14 |
| TR_ATTG | CI | RG | HG | CK | 135 | 0.14 |
| TR_ATTG | HI | RG | MG | HN | 0 | 0.00 |
| TR_ATTG | CI | KG | HG | FN | 0 | 0.00 |
| TR_ATAC | CI | VA | HI | ND | 1611 | 1.40 |
| TR_ATAC | HI | VA | CI | ND | 1563 | 1.36 |
| TR_ATAC | KI | HG | HI | ND | 1481 | 1.29 |
| TR_ATAC | HI | HG | HI | ND | 1418 | 1.23 |
| TR_ATAC | CI | KG | HI | AD | 1363 | 1.19 |
| TR_ATAC | CI | HG | HI | AD | 1341 | 1.17 |
| TR_ATAC | KI | QA | CI | ND | 1291 | 1.12 |
| TR_ATAC | CI | KG | CI | ND | 1290 | 1.12 |
| TR_ATAC | KI | RG | KI | ND | 1288 | 1.12 |
| TR_ATAC | CI | KG | HI | RD | 1273 | 1.11 |
| TR_ATAC | HI | KG | HI | KD | 1161 | 1.01 |
| TR_ATAC | KI | RG | CI | KD | 1056 | 0.92 |
| TR_ATAC | KI | RG | HI | ND | 1043 | 0.91 |
| TR_ATAC | CI | RG | HI | KD | 970 | 0.84 |
| TR_ATAC | KI | RG | KI | KD | 842 | 0.73 |
| TR_ATAC | CI | QG | CI | ND | 841 | 0.73 |
| TR_ATAC | KI | AA | HI | AD | 837 | 0.73 |
| TR_ATAC | CI | HG | CI | KD | 822 | 0.72 |
| TR_ATAC | KI | VA | HI | KD | 802 | 0.70 |
| TR_ATAC | CI | HG | KI | ND | 666 | 0.58 |
| TR_ATAC | HI | QA | KI | ND | 561 | 0.49 |
| TR_ATAC | KI | MG | HI | RD | 541 | 0.47 |

In this table, "AFU" is the background-corrected binding value (in arbitrary fluorescence units after subtracting the background signal). "Norm" is the background corrected value divided by the background corrected value for the cognate control with canonical RVDs at each position.

These results demonstrate that in this assay, several of the novel tetramers have higher activity (shown in bold) than the corresponding tetramer made of canonical RVDs (shown in underlined italics).

Analysis of Tetramer Activity in a TALEN

Following the identification of the most active novel tetramers by ELISA above (Table 1), several tetramers were chosen and assembled into CCR5 specific TALENs. In these experiments, the tetramers were combinatorially assembled into the relative positions within both CCR5 TALEN partners to allow the assembly of all possible tetramer combinations for a specific target. The tetramers chosen based on the ELISA results and used for the combinatorial assemblies as shown below in Table 3:

TABLE 3

Tetramers used for combinatorial assembly of CCR5-targeted TALENs

| Assembly group | Tetramers used for assembly |
|---|---|

Tetramers used for assembly of TALENs for L538 target: 5' TCATTACACCTGCAGCT 3'

| Group 1^ | QG KD KI AA | RG HI RD KI | KD KD KG CN | KD HI AN RD |
|---|---|---|---|---|
| | QG AD HI KG | KG HI KD HI | AD KD RG CN | KD HI CN KD |
| | KG KD KI VA | VA HI RD HI | KD KD KG FN | RD HI CN KD |
| | QG RD HI QG | AA HI RD KI | KD KD RG CN | RD HI CN RD |
| Group 2^ | QG KD KI AA | RG HI RD KI | AD RD HG HN | RD HI HN ND |
| | QG AD HI KG | VA CI ND HI | ND KD HG HN | RD HI GN ND |
| | HG RD HI HG | HG HI ND HI | ND ND HG KN | KD HI CK ND |
| | QG ND KI RG | VA HI ND KI | KD KD QG HN | |
| | __T C A T__ | __T A C A__ | __C C T G__ | __C A G C__ |
| | Target 4bp sequences | | | |

Tetramers used for assembly of TALENs for R557 target: 5' CTTCCAGAATTGATACT 3'

| Group 3^ | RD RG RG KD | KD HI FN HI | KI RG QG AN | CI KG HI AD |
|---|---|---|---|---|
| | RD RG KG AD | KD HI AN KI | KI KG MG AN | CI KG HI RD |
| | RD VA RG RD | KD HI AN CI | KI RG RG FN | HI KG HI KD |
| | RD AA QG AD | | HI KG VA AK | KI RG CI KD |
| Group 4^ | RD RG RG KD | KD HI HN KI | CI MG KG HN | CI VA HI ND |
| | RD RG KG AD | KD HI FN HI | KI HG QA HN | HI VA CI ND |
| | RD HG KG ND | ND HI HN KI | HI AA VA HN | KI HG HI ND |
| | ND HG RG ND | KD HI KN CI | CI HG HG CN | CI KG HI AD |
| | __C T T C__ | __C A G A__ | __A T T G__ | __A T A C__ |
| | Target 4bp sequences | | | |

^Group 1 used the RVD "KG" in the final half repeat, while Group 2 used "HG".
^Group 3 used the RVD "KG" in the final half repeat, while Group 4 used "HG".

In these experiments, all the TALENs from each tetramer group were assembled, and then 42 representative candidates of each group were tested by the Cel-I assay in four conditions, condition 1 ("c1"): All combinations of Group 1 paired with the 101047 canonical partner; condition 2 ("c2"): All combinations of Group 2 paired with the 101047 canonical partner; condition 3 ("c3"): All combinations of Group 3 paired with the 101041 canonical partner; and condition 4 ("c4"): All combinations of Group 4 paired with the 101041 canonical partner. The results are shown in Tables 4 to 7 below. The results have been sorted such that the most active TALEN pairs are at the top. The lane identities correspond to the lanes on the gels shown in FIG. 6.

TABLE 4

Nuclease results from Condition 1

| Condition | T1-TCAT | T2-TACA | T3-CCTG | T4-CAGC | Half-G | Lane | % NHEJ |
|---|---|---|---|---|---|---|---|
| 1 | QG-KD-KI-AA | VA-HI-RD-HI | KD-KD-RG-CN | KD-HI-CN-KD | KG | 10 | 36.6 |
| 1 | QG-AD-RI-KG | VA-HI-RD-HI | AD-KD-RG-CN | KD-HI-AN-RD | KG | 21 | 35.7 |
| 1 | QG-AD-HI-KG | VA-HI-RD-HI | KD-KD-RG-CN | RD-HI-CN-RD | KG | 2 | 34.6 |
| 1 | QG-KD-KI-AA | KG-HI-KD-HI | KD-KD-RG-CN | KD-HI-CN-KD | KG | 4 | 34.3 |
| 1 | QG-KD-KI-AA | VA-HI-RD-HI | KD-KD-KG-CN | KD-HI-CN-KD | KG | 35 | 32.9 |
| 1 | QG-KD-KI-AA | KG-HI-KD-HI | KD-KD-KG-CN | KD-HI-AN-RD | KG | 38 | 32.8 |
| 1 | QG-RD-HI-QG | VA-HI-RD-HI | KD-KD-KG-CN | KD-HI-AN-RD | KG | 12 | 32.4 |
| 1 | QG-RD-HI-QG | VA-HI-RD-HI | KD-KD-KG-CN | KD-HI-CN-KD | KG | 9 | 28.7 |
| 1 | QG-RD-HI-QG | KG-HI-KD-HI | AD-KD-RG-CN | RD-HI-CN-RD | KG | 37 | 27.7 |
| 1 | QG-RD-HI-QG | KG-HI-KD-HI | KD-KD-RG-CN | RD-HI-CN-RD | KG | 22 | 27.2 |
| 1 | QG-RD-HI-QG | AA-HI-RD-KI | KD-KD-RG-CN | KD-HI-AN-RD | KG | 42 | 26.0 |
| 1 | KG-KD-KI-VA | VA-HI-RD-HI | KD-KD-KG-CN | KD-HI-AN-RD | KG | 11 | 25.3 |
| 1 | QG-KD-KI-AA | KG-HI-KD-HI | KD-KD-KG-FN | RD-HI-CN-RD | KG | 24 | 25.3 |
| 1 | QG-RD-HI-QG | RG-HI-RD-KI | KD-KD-RG-CN | KD-HI-CN-RD | KG | 31 | 25.0 |
| 1 | QG-AD-HI-KG | VA-HI-RD-HI | KD-KD-KG-FN | RD-HI-CN-KD | KG | 5 | 24.4 |
| 1 | QG-KD-KI-AA | VA-HI-RD-HI | KD-KD-KG-CN | KD-HI-CN-KD | KG | 34 | 22.5 |
| 1 | KG-KD-KI-VA | VA-HI-RD-HI | KD-KD-RG-CN | KD-HI-AN-RD | KG | 18 | 22.2 |
| 1 | QG-KD-KI-AA | KG-HI-KD-HI | KD-KD-KG-FN | KD-HI-CN-KD | KG | 33 | 20.9 |
| 1 | QG-KD-KI-AA | AA-HI-RD-KI | KD-KD-KG-CN | RD-HI-CN-KD | KG | 30 | 20.6 |
| 1 | KG-KD-KI-VA | KG-HI-KD-HI | KD-KD-KG-FN | KD-HI-CN-KD | KG | 39 | 20.3 |
| 1 | QG-KD-KI-AA | VA-HI-RD-HI | KD-KD-RG-CN | RD-HI-CN-KD | KG | 28 | 20.1 |
| 1 | KG-KD-KI-VA | RG-HI-RD-KI | KD-KD-RG-CN | RD-HI-CN-RD | KG | 19 | 18.5 |
| 1 | QG-KD-KI-AA | RG-HI-RD-KI | KD-KD-KG-FN | RD-HI-CN-RD | KG | 14 | 18.3 |
| 1 | KG-KD-KI-VA | KG-HI-KD-HI | KD-KD-RG-CN | KD-HI-AN-RD | KG | 1 | 17.3 |
| 1 | QG-KD-KI-AA | VA-HI-RD-HI | AD-KD-RG-CN | KD-HI-CN-KD | KG | 17 | 16.9 |
| 1 | KG-KD-KI-VA | VA-HI-RD-HI | KD-KD-KG-FN | RD-HI-CN-RD | KG | 25 | 16.7 |
| 1 | QG-KD-KI-AA | RG-HI-RD-KI | KD-KD-KG-FN | KD-HI-CN-KD | KG | 8 | 13.1 |

TABLE 4-continued

Nuclease results from Condition 1

| Condition | T1-TCAT | T2-TACA | T3-CCTG | T4-CAGC | Half-G | Lane | % NHEJ |
|---|---|---|---|---|---|---|---|
| 1 | QG-RD-HI-QG | AA-HI-RD-KI | AD-KD-RG-CN | KD-HI-CN-KD | KG | 13 | 13.1 |
| 1 | QG-KD-KI-AA | KG-HI-KD-HI | RD-KD-KG-CN | RD-HI-CN-RD | KG | 20 | 11.8 |
| 1 | QG-AD-HI-KG | RG-HI-RD-KI | KD-KD-RG-CN | KD-HI-AN-RD | KG | 3 | 8.2 |
| 1 | QG-RD-HI-QG | RG-HI-RD-KI | RD-KD-KG-FN | RD-HI-CN-KD | KG | 41 | 8.2 |
| 1 | QG-NG-KI-AA | VA-HI-RD-HI | KD-KD-KG-FN | KD-HI-AN-RD | KG | 15 | 4.2 |
| 1 | QG-AD-HI-KG | VA-HI-RD-HI | AD-KD-RG-CN | KD-HI-CN-KD | KG | 6 | 2.6 |
| 1 | KG-KD-KI-VA | RG-HI-RD-KI | AD-KD-RG-CN | RD-HI-CN-KD | KG | 16 | 0.0 |
| 1 | KG-KD-KI-VA | VA-HI-RD-HI | AD-KD-RG-CN | KD-HI-AN-RD | KG | 26 | 0.0 |
| 1 | KG-KD-KI-VA | AA-HI-RD-KI | AD-KD-RG-CN | KD-HI-CN-KD | KG | 29 | 0.0 |
| 1 | QG-AD-HI-KG | VA-HI-RD-HI | KD-KD-KG-CN | RD-HI-CN-RD | KG | 32 | 0.0 |
| 1 | KG-KD-KI-VA | KG-HI-KD-HI | KD-KD-KG-FN | KD-HI-AN-RD | KG | 40 | 0.0 |

TABLE 5

Nuclease results from Condition 2

| Condition | T1- TCAT | T2- TACA | T3- CCTG | T4-CAGC | Half G | Lane | % NHEJ |
|---|---|---|---|---|---|---|---|
| 2 | QG-ND-KI-RG | VA-CI-ND-HI | ND-KD-HG-HN | KD-HI-CK-ND | HG | 83 | 64.1 |
| 2 | QG-AD-HI-KG | HG-HI-ND-HI | AD-RD-HG-HN | KD-HI-CK-ND | HG | 85 | 59.5 |
| 2 | HG-RD-HI-HG | VA-CI-ND-HI | KD-KD-QG-HN | RD-HI-HN-ND | HG | 46 | 54.5 |
| 2 | QG-AD-HI-KG | HG-HI-ND-HI | AD-RD-HG-HN | RD-HI-HN-ND | HG | 66 | 51.9 |
| 2 | QG-ND-KI-RG | VA-HI-ND-KI | AD-RD-HG-HN | RD-HI-HN-ND | HG | 56 | 51.4 |
| 2 | QG-AD-HI-KG | RG-HI-RD-KI | ND-KD-HG-KN | RD-HI-HN-ND | HG | 52 | 49.9 |
| 2 | QG-AD-HI-KG | RG-HI-RD-KI | AD-RD-HG-HN | KD-HI-CK-ND | HG | 76 | 47.5 |
| 2 | QG-AD-HI-KG | HG-HI-ND-HI | ND-ND-HG-KN | RD-HI-HN-ND | HG | 47 | 46.9 |
| 2 | QG-KD-KI-AA | VA-CI-ND-HI | ND-KD-HG-HN | RD-HI-HN-ND | HG | 54 | 46.7 |
| 2 | QG-AD-HI-KG | VA-CI-ND-HI | ND-KD-HG-HN | RD-HI-HN-ND | HG | 72 | 45.9 |
| 2 | QG-AD-HI-KG | VA-HI-ND-KI | AD-RD-HG-HN | RD-HI-HN-ND | HG | 50 | 44.4 |
| 2 | QG-AD-HI-KG | RG-HI-RD-KI | KD-KD-QG-HN | RD-HI-HN-ND | HG | 49 | 43.4 |
| 2 | QG-AD-HI-KG | VA-HI-ND-KI | ND-KD-HG-HN | RD-HI-HN-ND | HG | 74 | 42.7 |
| 2 | QG-AD-HI-KG | VA-CI-ND-HI | AD-RD-HG-HN | RD-HI-HN-ND | HG | 43 | 42.4 |
| 2 | QG-ND-KI-RG | VA-HI-ND-KI | ND-KD-HG-HN | RD-HI-GN-ND | HG | 71 | 42.1 |
| 2 | HG-RD-HI-HG | VA-CI-ND-HI | ND-KD-HG-HN | RD-HI-HN-ND | HG | 79 | 41.8 |
| 2 | HG-RD-HI-HG | HG-HI-ND-HI | AD-RD-HG-HN | RD-HI-GN-ND | HG | 78 | 41.4 |
| 2 | HG-RD-HI-HG | RG-HI-RD-KI | ND-KD-HG-HN | RD-HI-GN-ND | HG | 55 | 41.3 |
| 2 | QG-KD-KI-AA | VA-HI-ND-KI | AD-RD-HG-HN | RD-HI-HN-ND | HG | 44 | 40.2 |
| 2 | QG-ND-KI-RG | VA-HI-ND-KI | ND-ND-HG-KN | RD-HI-GN-ND | HG | 58 | 39.7 |
| 2 | HG-RD-HI-HG | RG-HI-RD-KI | ND-ND-HG-KN | RD-HI-HN-ND | HG | 77 | 39.6 |
| 2 | QG-RD-HI-HG | VA-HI-ND-KI | ND-KD-HG-HN | RD-HI-GN-ND | HG | 51 | 39.5 |
| 2 | QG-ND-KI-RG | VA-HI-ND-KI | KD-KD-QG-HN | KD-HI-CK-ND | HG | 81 | 38.3 |
| 2 | QG-ND-KI-RG | RG-HI-RD-KI | KD-KD-QG-HN | RD-HI-GN-ND | HG | 86 | 37.9 |
| 2 | QG-KD-KI-AA | RG-HI-RD-KI | AD-RD-HG-HN | RD-HI-GN-ND | HG | 84 | 37.2 |
| 2 | QG-ND-KI-RG | VA-HI-ND-KI | KD-KD-QG-HN | RD-HI-GN-ND | HG | 67 | 37.1 |
| 2 | HG-RD-HI-HG | RG-HI-RD-KI | ND-KD-HG-HN | KD-HI-CK-ND | HG | 63 | 36.9 |
| 2 | HG-RD-HI-HG | VA-CI-ND-HI | AD-RD-HG-HN | KD-HI-CK-ND | HG | 69 | 36.8 |
| 2 | QG-KD-KI-AA | HG-HI-ND-HI | ND-KD-HG-HN | KD-HI-CK-ND | HG | 57 | 35.9 |
| 2 | QG-KD-KI-AA | RG-HI-RD-KI | KD-KD-QG-HN | RD-HI-GN-ND | HG | 48 | 35.1 |
| 2 | QG-KD-KI-AA | RG-HI-RD-KI | ND-KD-HG-HN | RD-HI-GN-ND | HG | 60 | 34.9 |
| 2 | QG-AD-HI-KG | RG-HI-RD-KI | ND-ND-HG-KN | KD-HI-CK-ND | HG | 68 | 33.6 |
| 2 | QG-AD-HI-KG | HG-HI-ND-HI | ND-ND-HG-KN | KD-HI-CK-ND | HG | 80 | 33.4 |
| 2 | QG-KD-KI-AA | HG-HI-ND-HI | ND-ND-HG-KN | KD-HI-CK-ND | HG | 70 | 31.0 |
| 2 | QG-ND-KI-RG | VA-HI-ND-KI | ND-ND-HG-KN | RD-HI-HN-ND | HG | 59 | 30.9 |
| 2 | QG-KD-KI-AA | VA-HI-ND-KI | KD-KD-QG-HN | KD-HI-CK-ND | HG | 73 | 26.7 |
| 2 | QG-ND-KI-RG | VA-HI-ND-KI | AD-RD-HG-HN | RD-HI-GN-ND | HG | 61 | 26.5 |
| 2 | QG-AD-HI-KG | VA-CI-ND-HI | ND-ND-HG-KN | RD-HI-HN-ND | HG | 65 | 26.1 |
| 2 | HG-RD-HI-HG | HG-HI-ND-HI | AD-RD-HG-HN | RD-HI-HN-ND | HG | 75 | 20.5 |
| 2 | QG-ND-KI-RG | HG-HI-ND-HI | ND-KD-HG-HD | RD-HI-GN-ND | HG | 45 | 0.0 |
| 2 | QG-ND-KI-RG | RG-HI-RD-KI | ND-KD-HG-HN | RD-HI-HN-ND | HG | 53 | 0.0 |
| 2 | QG-KD-KI-AA | RG-HI-RD-KI | KD-KD-QG-HN | RD-HI-GN-ND | HG | 62 | 0.0 |
| 2 | QG-KD-KI-AA | HG-HI-ND-HI | AD-RD-HG-HN | KD-HI-CK-ND | HG | 82 | 0.0 |

TABLE 6

Nuclease results from Condition 3

| Condition | T1-CTTC | T2-CAGA | T3-ATTG | T4-ATAC | Half-G | lane | % NHEJ |
|---|---|---|---|---|---|---|---|
| 3 | RD-AA-QG-AD | KD-HI-FN-HI | KI-RG-RG-FN | KI-RG-CI-KD | KG | 5 | 56.3 |
| 3 | RD-AA-QG-AD | KD-HI-AN-KI | KI-RG-RG-FN | CI-KG-HI-AD | KG | 9 | 56.2 |
| 3 | RD-AA-QG-AD | KD-HI-AN-CI | KI-RG-RG-FN | CI-KG-HI-AD | KG | 13 | 54.9 |
| 3 | RD-VA-RG-RD | KD-HI-AN-CI | KI-RG-RG-FN | CI-KG-HI-AD | KG | 2 | 54.2 |
| 3 | RD-VA-RG-RD | KD-HI-FN-HI | KI-RG-QG-AN | HI-KG-HI-KD | KG | 15 | 51.5 |
| 3 | RD-AA-QG-AD | KD-HI-AN-KI | KI-KG-MG-AN | HI-KG-HI-KD | KG | 38 | 50.9 |
| 3 | RD-RG-RG-KD | KD-HI-FN-HI | KI-RG-QG-AN | HI-KG-HI-KD | KG | 26 | 49.3 |
| 3 | RD-RG-KG-AD | KD-HI-FN-HI | KI-KG-MG-AN | CI-KG-HI-RD | KG | 3 | 48.4 |
| 3 | RD-RG-KG-AD | KD-HI-AN-KI | KI-KG-MG-AN | KI-RG-CI-KD | KG | 23 | 48.2 |
| 3 | RD-RG-KG-AD | KD-HI-AN-KI | KI-RG-QG-AN | KI-RG-CI-KD | KG | 7 | 48.1 |
| 3 | RD-VA-RG-RD | KD-HI-AN-CI | KI-RG-RG-FN | CI-KG-HI-AD | KG | 24 | 47.4 |
| 3 | RD-VA-RG-RD | KD-HI-FN-HI | KI-KG-MG-AN | HI-KG-HI-KD | KG | 14 | 45.0 |
| 3 | RD-VA-RG-RD | KD-HI-AN-KI | KI-RG-RG-FN | KI-RG-CI-KD | KG | 37 | 43.6 |
| 3 | RD-AA-QG-AD | KD-HI-FN-HI | KI-KG-MG-AN | KI-RG-CI-KD | KG | 1 | 43.4 |
| 3 | RD-RG-KG-AD | KD-HI-AN-CI | KI-KG-MG-AN | CI-KG-HI-AD | KG | 42 | 43.3 |
| 3 | RD-VA-RG-RD | KD-HI-AN-CI | KI-KG-MG-AN | HI-KG-HI-KD | KG | 32 | 40.7 |
| 3 | RD-AA-QG-AD | KD-HI-AN-CI | KI-RG-QG-AN | CI-KG-HI-RD | KG | 20 | 40.2 |
| 3 | RD-VA-RG-RD | KD-HI-AN-CI | KI-RG-RG-FN | KI-RG-CI-KD | KG | 41 | 39.9 |
| 3 | RD-RG-RG-KD | KD-HI-AN-KI | KI-RG-QG-AN | CI-KG-HI-AD | KG | 4 | 39.7 |
| 3 | RD-RG-RG-KD | KD-HI-AN-CI | KI-RG-RG-FN | CI-KG-HI-AD | KG | 17 | 38.9 |
| 3 | RD-RG-KG-AD | KD-HI-AN-KI | KI-RG-QG-AN | CI-KG-HI-RD | KG | 40 | 38.4 |
| 3 | RD-RG-KG-AD | KD-HI-AN-CI | KI-RG-RG-FN | CI-KG-HI-RD | KG | 22 | 35.9 |
| 3 | RD-RG-RG-KD | KD-HI-FN-HI | KI-KG-MG-AN | KI-RG-CI-KD | KG | 34 | 34.3 |
| 3 | RD-AA-QG-AD | KD-HI-AN-CI | KI-KG-MG-AN | KI-RG-CI-KD | KG | 36 | 33.0 |
| 3 | RD-VA-RG-RD | KD-HI-AN-KI | KI-KG-MG-AN | CI-KG-HI-AD | KG | 39 | 32.9 |
| 3 | RD-RG-RG-KD | KD-HI-FN-HI | KI-RG-RG-FN | CI-KG-HI-RD | KG | 16 | 32.0 |
| 3 | RD-AA-QG-AD | KD-HI-AN-CI | KI-RG-RG-FN | KI-RG-CI-KD | KG | 21 | 31.4 |
| 3 | RD-VA-RG-RD | KD-HI-AN-CI | HI-KG-VA-AK | KI-RG-CI-KD | KG | 25 | 31.2 |
| 3 | RD-RG-KG-AD | KD-HI-AN-KI | KI-RG-RG-FN | KI-RG-CI-KD | KG | 11 | 30.1 |
| 3 | RD-RG-KG-AD | KD-HI-FN-HI | KI-RG-RG-FN | CI-KG-HI-AD | KG | 10 | 28.5 |
| 3 | RD-RG-RG-KD | KD-HI-AN-KI | HI-KG-VA-AK | CI-KG-HI-AD | KG | 33 | 19.6 |
| 3 | RD-AA-QG-AD | KD-HI-AN-CI | HI-KG-VA-AK | CI-KG-HI-RD | KG | 27 | 15.6 |
| 3 | RD-VA-RG-RD | KD-HI-AN-KI | HI-KG-VA-AK | KI-RG-CI-KD | KG | 28 | 14.8 |
| 3 | RD-VA-RG-RD | KD-HI-FN-HI | KI-RG-QG-AN | CI-KG-HI-AD | KG | 31 | 14.5 |
| 3 | RD-VA-RG-RD | KD-HI-AN-CI | HI-KG-VA-AK | KI-RG-CI-KD | KG | 19 | 14.0 |
| 3 | RD-VA-RG-RD | KD-HI-FN-HI | HI-KG-VA-AK | KI-RG-CI-KD | KG | 18 | 13.3 |
| 3 | RD-RG-RG-KD | KD-HI-FN-HI | HI-KG-MG-AN | CI-KG-HI-RD | KG | 12 | 11.6 |
| 3 | RD-RG-RG-KD | KD-HI-AN-KI | KI-RG-RG-FN | HI-KG-HI-KD | KG | 30 | 11.5 |
| 3 | RD-VA-RG-RD | KD-HI-AN-CI | KI-RG-QG-AN | CI-KG-HI-AD | KG | 29 | 9.1 |
| 3 | RD-RG-RG-KD | KD-HI-FN-HI | HI-KI-RG-RG | CI-KG-HI-AD | KG | 6 | 3.0 |
| 3 | RD-RG-RG-KD | KD-HI-AN-KI | KI-KG-MG-AN | CI-KG-HI-RD | KG | 8 | 0.0 |

TABLE 7

Nuclease results from Condition 4

| Condition | T1-CTTC | T2-CAGA | T3-ATTG | T4-ATAC | Half G | Lane | % NHEJ |
|---|---|---|---|---|---|---|---|
| 4 | ND-HG-RG-ND | KD-HI-KN-CI | CI-MG-KG-HN | CI-KG-HI-AD | HG | 56 | 59.5 |
| 4 | ND-HG-RG-ND | ND-HI-HN-KI | HI-AA-VA-HN | HI-VA-CI-ND | HG | 59 | 59.2 |
| 4 | ND-HG-RG-ND | ND-HI-HN-KI | CI-MG-KG-HN | HI-VA-CI-ND | HG | 69 | 58 |
| 4 | ND-HG-RG-ND | KD-HI-FN-HI | CI-HG-HG-CN | KI-HG-HI-ND | HG | 62 | 55.1 |
| 4 | ND-HG-RG-ND | KD-HI-KN-CI | CI-HG-HG-CN | CI-VA-HI-ND | HG | 51 | 54.4 |
| 4 | RD-HG-KG-ND | ND-HI-HN-KI | CI-HG-HG-CN | HI-VA-CI-ND | HG | 58 | 54.3 |
| 4 | ND-HG-RG-ND | ND-HI-HN-KI | CI-MG-KG-HN | CI-VA-HI-ND | HG | 48 | 54.3 |
| 4 | RD-HG-KG-ND | KD-HI-KN-CI | KI-HG-QA-HN | KI-HG-HI-ND | HG | 77 | 51.3 |
| 4 | ND-HG-RG-ND | ND-HI-HN-KI | HI-AA-VA-HN | KI-HG-HI-ND | HG | 50 | 51.3 |
| 4 | RD-RG-KG-AD | KD-HI-FN-HI | CI-MG-KG-HN | HI-VA-CI-ND | HG | 73 | 50.9 |
| 4 | RD-HG-KG-ND | ND-HI-HN-KI | CI-HG-HG-CN | CI-KG-HI-AD | HG | 46 | 50.9 |
| 4 | RD-RG-RG-KD | ND-HI-HN-KI | HI-AA-VA-HN | KI-HG-HI-ND | HG | 49 | 50.4 |
| 4 | ND-HG-RG-ND | ND-HI-HN-KI | HI-AA-VA-HN | KI-HG-HI-ND | HG | 70 | 50 |
| 4 | RD-RG-RG-KD | KD-HI-FN-HI | CI-MG-KG-HN | KI-HG-HI-ND | HG | 87 | 50.0 |
| 4 | RD-RG-KG-AD | ND-HI-HN-KI | KI-HG-QA-HN | HI-VA-CI-ND | HG | 55 | 49.2 |
| 4 | RD-HG-KG-ND | KD-HI-FN-HI | CI-HG-HG-CN | CI-VA-HI-ND | HG | 83 | 48.2 |
| 4 | RD-HG-KG-ND | KD-HI-KN-CI | KI-HG-QA-HN | CI-VA-HI-ND | HG | 79 | 46.3 |
| 4 | RD-RG-KG-AD | KD-HI-KN-CI | KI-HG-QA-HN | KI-HG-HI-ND | HG | 80 | 46.0 |
| 4 | RD-HG-KG-ND | ND-HI-HN-KI | HI-AA-VA-HN | HI-VA-CI-ND | HG | 67 | 45.3 |
| 4 | RD-RG-KG-AD | KD-HI-FN-HI | CI-HG-HG-CN | KI-HG-HI-ND | HG | 66 | 43.5 |
| 4 | RD-HG-KG-ND | KD-HI-FN-HI | KI-HG-QA-HN | CI-KG-HI-AD | HG | 78 | 42.9 |
| 4 | RD-RG-KG-AD | KD-HI-FN-HI | CI-MG-KG-HN | HI-VA-CI-ND | HG | 72 | 42.7 |

TABLE 7-continued

Nuclease results from Condition 4

| Condition | T1-CTTC | T2-CAGA | T3-ATTG | T4-ATAC | Half G | Lane | % NHEJ |
|---|---|---|---|---|---|---|---|
| 4 | RD-HG-KG-ND | KD-HI-HN-KI | CI-HG-HG-CN | CI-KG-HI-AD | HG | 45 | 42.5 |
| 4 | RD-HG-KG-ND | KD-HI-FN-HI | KI-HG-QA-HN | CI-VA-HI-ND | HG | 52 | 41.3 |
| 4 | RD-HG-KG-ND | KD-HI-FN-HI | HI-AA-VA-HN | HI-VA-CI-ND | HG | 57 | 39.9 |
| 4 | ND-HG-RG-ND | KD-HI-FN-HI | KI-HG-QA-HN | HI-VA-CI-ND | HG | 53 | 39.7 |
| 4 | RD-RG-RG-KD | ND-HI-HN-KI | CI-MG-KG-HN | HI-VA-CI-ND | HG | 81 | 39.2 |
| 4 | RD-RG-RG-KD | KD-HI-KN-CI | CI-MG-KG-HN | KI-HG-HI-ND | HG | 47 | 36.6 |
| 4 | RD-RG-RG-KD | ND-HI-HN-KI | HI-AA-VA-HN | CI-VA-HI-ND | HG | 74 | 34.0 |
| 4 | RD-RG-RG-KD | KD-HI-KN-CI | CI-HG-HG-CN | CI-VA-HI-ND | HG | 43 | 33.7 |
| 4 | ND-HG-RG-ND | KD-HI-KN-CI | CI-MG-KG-HN | HI-VA-CI-ND | HG | 60 | 33.5 |
| 4 | RD-RG-KG-AD | KD-HI-HN-KI | KI-HG-QA-HN | CI-VA-HI-ND | HG | 82 | 30.9 |
| 4 | RD-RG-RG-KD | KD-HI-HN-KI | HI-AA-VA-HN | KI-HG-HI-ND | HG | 75 | 29.2 |
| 4 | RD-RG-KG-AD | KD-HI-KN-CI | CI-MG-KG-HN | HI-VA-CI-ND | HG | 88 | 28.9 |
| 4 | ND-HG-RG-ND | KD-HI-FN-HI | KI-HG-QA-HN | CI-VA-HI-ND | HG | 63 | 27.6 |
| 4 | RD-RG-RG-KD | KD-HI-HN-KI | HI-AA-VA-HN | HI-VA-CI-ND | HG | 76 | 26.6 |
| 4 | RD-RG-RG-KD | KD-HI-KN-CI | HI-AA-VA-HN | HI-VA-CI-ND | HG | 65 | 24.8 |
| 4 | RD-RG-RG-KD | KD-HI-HN-KI | KI-HG-QA-HN | CI-KG-HI-AD | HG | 86 | 22.5 |
| 4 | RD-HG-KG-ND | KD-HI-HN-KI | CI-HG-HG-CN | CI-KG-HI-AD | HG | 85 | 20.4 |
| 4 | RD-RG-RG-KD | ND-HI-HN-KI | CI-HG-HG-CN | CI-KG-HI-AD | HG | 44 | 20.2 |
| 4 | RD-RG-RG-KD | KD-HI-FN-HI | CI-MG-KG-HN | CI-KG-HI-AD | HG | 61 | 19.2 |
| 4 | RD-RG-KG-AD | KD-HI-FN-HI | KI-HG-QA-HN | CI-KG-HI-AD | HG | 84 | 12.2 |
| 4 | RD-HG-RG-ND | KD-HI-KN-CI | KI-HG-QA-HN | HI-VA-CI-ND | HG | 68 | 10.0 |
| 4 | RD-RG-KG-AD | KD-HI-HN-KI | CI-HG-HG-CN | KI-HG-HI-ND | HG | 64 | 0.0 |

Control experiments performed with the 101041/101047 pair typically yielded a % NHEJ result in this assay of 45-55%. These results show that the novel tetramers were capable of yielding results that are at least equal to those of the canonical nucleases, and in some cases were superior. Testing of Unique CCR5-Specific TALENs The CCR5 TALENs identified above in combination with the canonical partners are then tested in combination with unique TALEN partners. For these experiments, the sets shown in Table 8 are combined and tested for Cel-I activity, and the results demonstrate that these proteins are highly active.

TABLE 8

Unique tetramer CCR5 TALENs

| L538 Binding site | Tetramer 1 (T1) TCAT | Tetramer 2 (T2) TACA | Tetramer 3 (T3) CCTG | Tetramer 4 (T4) CAGC | Half Repeat G |
|---|---|---|---|---|---|
| Canonical RVDs | NG-HD-NI-NG | NG-NI-HD-NI | HD-HD-NG-NN | HD-NI-NN-HD | NG |
| 1-1 RVDs | QG-KD-KI-AA | VA-HI-RD-HI | KD-KD-RG-CN | KD-HI-CN-KD | KG |
| 1-2 RVDs | QG-AD-RI-KG | VA-HI-RD-HI | AD-KD-RG-CN | KD-HI-AN-RD | KG |
| 1-3 RVDs | QG-AD-HI-KG | VA-HI-RD-HI | KD-KD-RG-CN | RD-HI-CN-RD | KG |
| 1-4 RVDs | QG-KD-KI-AA | KG-HI-KD-HI | KD-KD-RG-CN | KD-HI-AN-RD | KG |
| 1-5 RVDs | QG-KD-KI-AA | VA-HI-RD-HI | KD-KD-KG-CN | KD-HI-CN-KD | KG |
| 1-6 RVDs | QG-KD-KI-AA | KG-HI-KD-HI | KD-KD-KG-CN | KD-HI-AN-RD | KG |
| 1-7 RVDs | QG-RD-HI-QG | VA-HI-RD-HI | KD-KD-KG-CN | KD-HI-AN-RD | KG |
| 1-8 RVDs | QG-RD-HI-QG | VA-HI-RD-HI | KD-KD-KG-CN | KD-HI-CN-KD | KG |
| 2-1 RVDs | QG-ND-KI-RG | VA-CI-ND-HI | ND-KD-HG-HN | KD-HI-CK-ND | HG |
| 2-2 RVDs | QG-AD-HI-KG | HG-HI-ND-HI | AD-RD-HG-HN | KD-HI-CK-ND | HG |
| 2-3 RVDs | HG-RD-HI-HG | VA-CI-ND-HI | KD-KD-QG-HN | RD-HI-HN-ND | HG |
| 2-4 RVDs | QG-AD-HI-KG | HG-HI-ND-HI | AD-RD-HG-HN | RD-HI-HN-ND | HG |
| 2-5 RVDs | QG-ND-KI-RG | VA-HI-ND-KI | AD-RD-HG-HN | RD-HI-HN-ND | HG |

| R557 Binding site | Tetramer 1 (T1) CTTC | Tetramer 2 (T2) CAGA | Tetramer 3 (T3) ATTG | Tetramer 4 (T4) ATAC | Half Repeat G |
|---|---|---|---|---|---|
| Canonical RVDs | HD-NI-NG-HD | HD-NI-NN-NI | NI-NG-NG-NN | NI-NG-NI-HD | NG |
| 3-1 RVDs | RD-AA-QG-AD | KD-HI-FN-HI | KI-RG-RG-FN | KI-RG-CI-KD | KG |
| 3-2 RVDs | RD-AA-QG-AD | KD-HI-AN-KI | KI-RG-RG-FN | CI-KG-HI-AD | KG |
| 3-3 RVDs | RD-AA-QG-AD | KD-HI-AN-CI | KI-RG-RG-FN | CI-KG-HI-AD | KG |
| 3-4 RVDs | RD-VA-RG-RD | KD-HI-AN-CI | KI-RG-RG-FN | CI-KG-HI-RD | KG |
| 3-5 RVDs | RD-VA-RG-RD | KD-HI-FN-HI | KI-RG-QG-AN | HI-KG-HI-KD | KG |
| 3-6 RVDs | RD-AA-QG-AD | KD-HI-AN-KI | KI-KG-MG-AN | HI-KG-HI-KD | KG |
| 3-7 RVDs | RD-RG-RG-KD | KD-HI-FN-HI | KI-RG-QG-AN | HI-KG-HI-KD | KG |
| 3-8 RVDs | RD-RG-KG-AD | KD-HI-FN-HI | KI-KG-MG-AN | CI-KG-HI-RD | KG |
| 4-1 RVDs | ND-HG-RG-ND | KD-HI-KN-CI | CI-MG-KG-HN | CI-KG-HI-AD | HG |
| 4-2 RVDs | ND-HG-RG-ND | ND-HI-HN-KI | HI-AA-VA-HN | HI-VA-CI-ND | HG |
| 4-3 RVDs | RD-HG-KG-ND | ND-HI-HN-KI | CI-MG-KG-HN | HI-VA-CI-ND | HG |
| 4-4 RVDs | ND-HG-RG-ND | KD-HI-FN-HI | CI-HG-HG-CN | KI-HG-HT-ND | HG |
| 4-5 RVDs | ND-HG-RG-ND | KD-HI-KN-CI | CI-HG-HG-CN | CI-VA-HI-ND | HG |

The TALENs shown in Table 8 were then used as pairs to cleave the CCR5 target (e.g., one L538 binding TALEN and one R557 binding TALEN) and the cleavage was measured by the Cel-I assay. The tests were performed three times and the results from each test are presented below in Table 9.

TABLE 9 a: Activity of Novel TALENs, test 1

|  | 3-1 | 3-2 | 3-3 | 3-4 | 3-5 | 3-6 | 3-7 | 3-8 |
|---|---|---|---|---|---|---|---|---|
| 1-1 | 1.1 | 2.5 | 5.7 | 0.8 | 2.4 | 1.6 | 0.0 | 1.7 |
| 1-2 | 1.6 | 5.5 | 8.7 | 1.2 | 3.2 | 2.2 | 1.5 | 5.6 |
| 1-3 | 1.1 | 2.8 | 2.5 | 0.0 | 1.6 | 1.7 | 0.7 | 2.5 |
| 1-4 | 3.1 | 7.7 | 7.8 | 2.2 | 4.4 | 2.6 | 1.6 | 4.8 |
| 1-5 | 1.3 | 2.8 | 4.5 | 0.0 | 2.0 | 1.4 | 0.0 | 2.8 |
| 1-6 | 1.0 | 2.5 | 3.6 | 0.0 | 1.6 | 2.0 | 0.6 | 2.4 |
| 1-7 | 0.5 | 2.1 | 5.5 | 0.0 | 1.8 | 1.4 | 0.8 | 2.0 |
| 1-8 | 0.0 | 0.4 | 1.2 | 0.0 | 0.0 | 2.9 | 0.0 | 0.0 |

|  | 4-1 | 4-2 | 4-3 | 4-6 | 4-7 |  |  |  |
|---|---|---|---|---|---|---|---|---|
| 2-1 | 2.0 | 1.7 | 2.1 | 2.1 | 2.8 | Control (average) |  | 6.6 |
| 2-2 | 12.2 | 6.0 | 7.0 | 6.0 | 5.8 | GFP |  | 0 |
| 2-3 | 7.9 | 7.7 | 8.0 | 8.6 | 7.1 |  |  |  |
| 2-5 | 6.2 | 4.8 | 6.2 | 5.2 | 5.6 |  |  |  |
| 2-6 | 5.9 | 5.3 | 4.6 | 4.1 | 4.9 |  |  |  | b: Activity of Novel TALENs, test 2

|  | 3-1 | 3-2 | 3-3 | 3-4 | 3-5 | 3-6 | 3-7 | 3-8 |
|---|---|---|---|---|---|---|---|---|
| 1-1 | 2.6 | 4.4 | 5.2 | 1.8 | 1.0 | 2.1 | 2.5 | 3.5 |
| 1-2 | 5.6 | 5.7 | 11.3 | 4.7 | 2.8 | 4.9 | 0.7 | NA |
| 1-3 | 3.8 | 8.9 | 8.5 | 1.7 | 3.3 | 4.4 | 3.4 | 4.9 |
| 1-4 | 4.2 | 8.2 | 18.6 | 7.3 | 3.8 | 5.4 | 0.0 | NA |
| 1-5 | 5.1 | 4.6 | 4.4 | 1.7 | 0.8 | 11.2 | 2.4 | 2.5 |
| 1-6 | 3.3 | 3.2 | 3.6 | 1.3 | 3.9 | 4.0 | 0.5 | 2.9 |
| 1-7 | 2.3 | 3.7 | 6.0 | 1.4 | 2.2 | 2.9 | 2.2 | 2.9 |
| 1-8 | 3.1 | 5.3 | NA | 0.8 | NA | 1.4 | 1.3 | 5.9 |

|  | 4-1 | 4-2 | 4-3 | 4-4 | 4-5 |  |  |  |
|---|---|---|---|---|---|---|---|---|
| 2-1 | 2.9 | 2.2 | 6.1 | 5.3 | 1.8 | Control (average) |  | 5.5 |
| 2-2 | 6.0 | 7.8 | 10.7 | 8.1 | 6.7 | GFP |  | 0 |
| 2-3 | 4.1 | 8.6 | 12.0 | 11.7 | 23.3 |  |  |  |
| 2-4 | 2.9 | 2.1 | 4.6 | 3.1 | 1.4 |  |  |  |
| 2-5 | 5.3 | 6.6 | 11.3 | 20.9 | 21.3 |  |  |  | c: Activity of Novel TALENs, test 3

|  | 3-1 | 3-2 | 3-3 | 3-4 | 3-5 | 3-6 | 3-7 | 3-8 |
|---|---|---|---|---|---|---|---|---|
| 1-1 | 4.3 | 9.3 | 9.0 | 5.1 | 1.2 | 7.1 | 4.2 | 3.0 |
| 1-2 | 4.6 | 9.2 | 6.2 | 7.0 | 3.0 | 5.5 | 3.1 | 3.0 |
| 1-3 | 4.8 | 8.5 | 7.0 | 5.5 | 3.2 | 3.5 | 3.5 | 3.4 |
| 1-4 | 5.5 | 8.4 | 16.8 | 8.3 | 4.2 | 9.9 | 0.0 | 2.4 |
| 1-5 | 5.6 | 13.4 | 6.2 | 3.9 | 1.4 | 7.3 | 5.1 | 2.0 |
| 1-6 | 5.5 | 9.9 | 11.5 | 8.2 | 5.3 | 7.1 | 4.0 | 2.7 |
| 1-7 | 5.2 | 8.5 | 7.3 | 7.3 | 2.7 | 4.0 | 2.1 | 1.8 |
| 1-8 | 3.3 | 8.7 | 6.8 | 2.9 | 3.6 | 5.0 | 2.9 | 2.9 |

|  | 4-1 | 4-2 | 4-3 | 4-4 | 4-5 |  |  |  |
|---|---|---|---|---|---|---|---|---|
| 2-1 | 10.6 | 9.3 | 11.9 | 14.1 | 16.1 | Control |  | 14.6 |
| 2-2 | 10.4 | 12.1 | 11.0 | 17.0 | 14.8 | GFP |  | 0 |
| 2-3 | 14.1 | 10.8 | NA | 15.8 | 16.5 |  |  |  |
| 2-4 | 7.9 | 6.7 | 12.5 | 13.8 | 10.9 |  |  |  |
| 2-5 | 9.7 | 14.2 | 11.7 | 15.5 | 9.9 |  |  |  |

The results presented in Table 9 demonstrate that the novel TALENs comprising atypical RVDs are capable of acting with equal or greater activity than those constructed with the canonical RVDs.

To examine the stability and cytotoxicity of the non-canonical RVDs in cells, the TALEN pairs were tested for signal at day 3 and day 10 following introduction of the nucleases into K562 cells by nucleofection. The results (Table 10) demonstrate that the modification signal is stable and the TALENs comprising novel RVDs do not display increased toxicity as compared to TALENs comprising the canonical ones (pair 101041/101047).

TABLE 10

Stability of target modification by TALENs

| TALEN | NHEJ % (3 days) | NHEJ % (10 days) | % of retained modification |
|---|---|---|---|
| GFP | 0 | 0 | NA |
| 1-2:3-1 | 1.6 | 0.3 | 19.1 |
| 1-4:3-1 | 3.1 | 0.7 | 20.9 |
| 1-2:3-2 | 5.5 | 2.0 | 36.9 |
| 1-4:3-2 | 7.7 | 2.9 | 37.6 |
| 1-1:3-3 | 5.7 | 2.0 | 34.3 |
| 1-2:3-3 | 8.7 | 3.3 | 37.8 |
| 1-3:3-3 | 2.5 | 1.2 | 48.5 |
| 1-4:3-3 | 7.8 | 3.3 | 41.6 |
| 1-5:3-3 | 4.5 | 1.9 | 41.5 |
| 1-6:3-3 | 3.6 | 1.4 | 37.5 |
| 1-7:3-3 | 5.5 | 1.6 | 28.6 |
| 1-2:3-8 | 5.6 | 0.8 | 14.3 |
| 1-4:3-8 | 4.8 | 1.6 | 33.5 |
| 2-2:4-1 | 12.2 | 2.3 | 19.0 |
| 2-3:4-1 | 7.9 | 2.5 | 31.4 |
| 2-5:4-1 | 6.2 | 1.7 | 26.7 |
| 2-6:4-1 | 5.9 | 2.1 | 35.0 |
| 2-2:4-2 | 6.0 | 2.1 | 35.6 |
| 2-2:4-3 | 7.0 | 1.7 | 24.6 |
| 2-2:4-6 | 6.0 | 1.7 | 28.7 |
| 2-2:4-7 | 5.8 | 1.4 | 23.4 |
| 101041:101047 | 10.9 | 4.9 | 44.6 |
| 101041:101047 | 3.0 | 0.8 | 27.0 |

Example 2

Comparison of TALENs and Off Target Analysis

Figure 7:
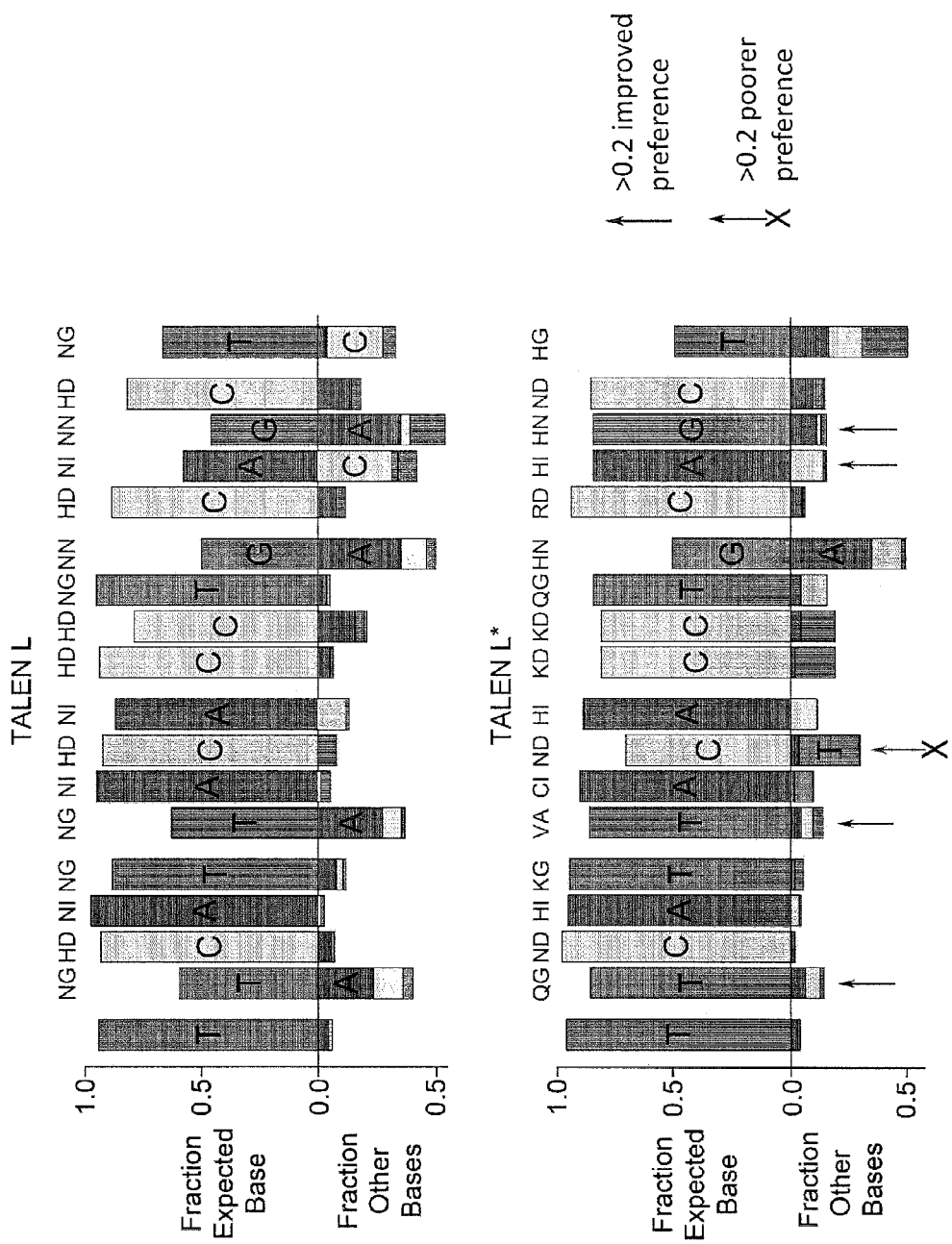
FIG. 7 depicts the SELEX analysis for TALEN 'L' and TALEN 'L*' (target sites shown in SEQ ID NO:141). The results shown that the TALEN L*, comprising all non-canonical RVDs, has increased binding specificity at several positions.
Figure 8:
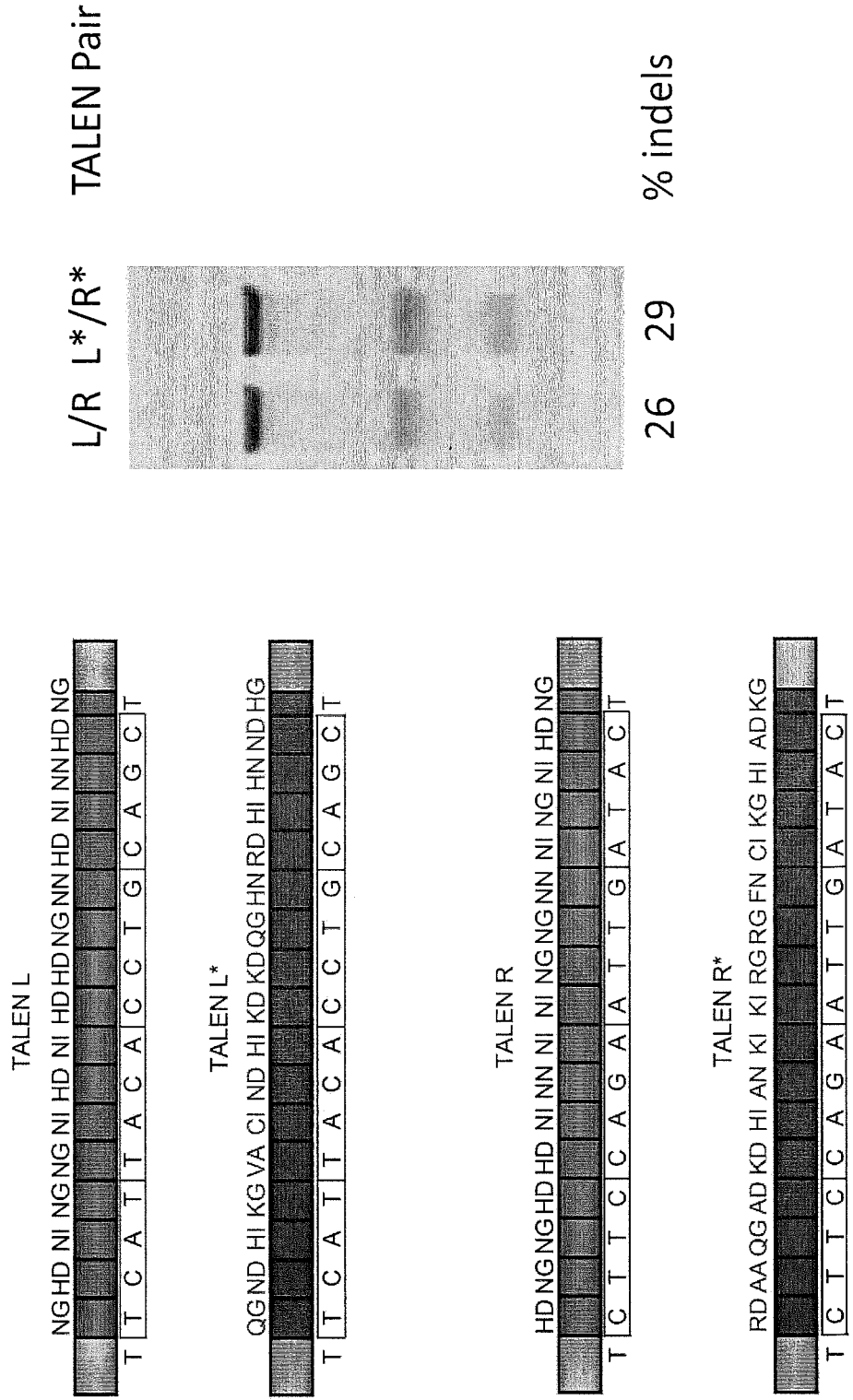
FIG. 8 shows the RVD and target sequences and activity for the TALENs L (SBS101041), L* (SBS102204), R and R* (SEQ ID NOS 141, 141, 139, and 139, respectively). The TALEN pair R and L were remade using noncanonical RVDs to result in R* and L* and the target sequences that these proteins bind to are depicted along with their RVD sequences on the left of the figure. The gel at the right depicts the results of a Cel-I cleavage assay and demonstrates that both pairs are active.

We compared two CCR5 L partners as described above where one partner comprised all canonical RVDs SBS101041) and the other comprised all novel RVDs ('L*', SBS102204) by SELEX (FIG. 7). The use of the novel RVDs resulted in improved specificity of base selection at several positions. Similarly, two CCR5 R partners were made where on used all canonical RVDs ('R', SBS101047) and the other utilized novel RVDs ('R*', SBS102109). The pairs were tested in the Cel I assay (FIG. 8), and were found to have very similar levels of cleavage activity.

Figure 9:
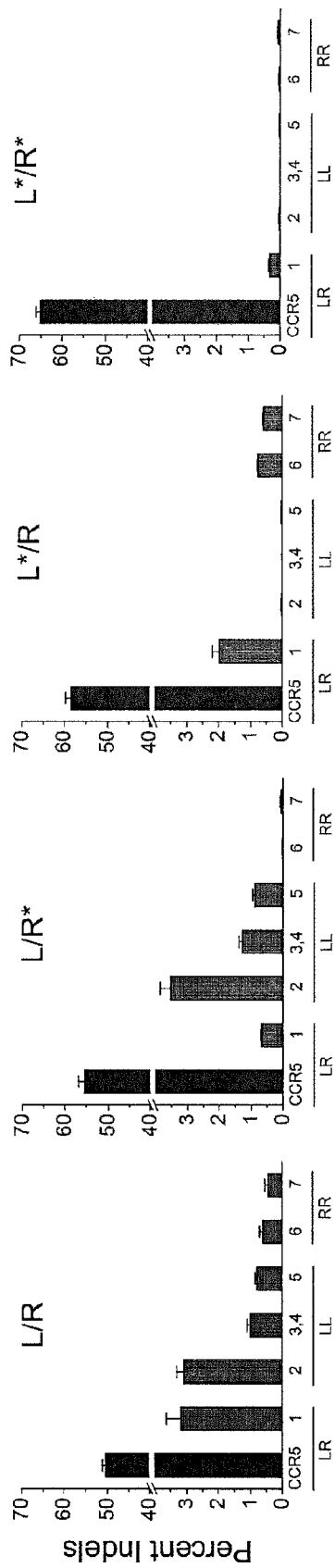
FIG. 9 shows a series of histograms demonstrating activity (percent indels) of the TALEN pairs for both on- and off-target sites in K562 cells. The left most bar of each graph is the activity of the pair on the intended CCR5 target (note the break in the legend on the x-axis). The off-target cleavage activity is shown in groups where the cut is caused by either a heterodimeric pairing ('LR') or a homodimeric pairing ('LL' or 'RR'). The pair transduced is indicated at the top of each graph.

Next, off-target cleavage was examined by searching the human genome for the best matches for targeting by the CCR5 TALEN L and TALEN R proteins, where the analysis included L+R heterodimeric pairs, and L+L and R+R homodimeric pairs. Aside from the intended target, one site was identified with 7 mismatches, and twenty two were identified with 8 mismatches. Each of these loci were analyzed for off target cleavage by deep sequencing of K562 cells treated with the L+R, L*+R, L*+R*, L+R* and eGFP. K562 cells were treated with the TALENs as described previously, and subject to transient hypothermia to enhance activity. The sequencing results of the top 13 off target sites are shown below in Table 11 and in groups in FIG. 9, and demonstrated a reduction in off target activity.

In Table 11, the off-target sites analyzed are identified as 'OT1-OT13' and the type of target site (homodimer (LL or RR) or heterodimer (LR) binding) is also identified as 'site'. The total sequences are shown and the total sequences found containing inserts or deletions (indels). The pairs transduced into the K562 cells are shown across the top, (L/R, L/R*, L*/R, L*/R*, or the GFP plasmid control). Cleavage activity detected at the intended site is also indicated (CCR5). At off-target site 2 (OT2), a 190-fold reduction in off target activity was found.

TABLE 11

Off target sequencing analysis of TALEN pairs

| | | L/R | | | L/R* | | | L*/R | |
|---|---|---|---|---|---|---|---|---|---|
| Locus | site | total | indels | % indels | total | indels | % indels | total | indels |
| CCR5 | LR | 40875 | 20703 | 50.65 | 43215 | 23999 | 55.53 | 49486 | 29027 |
| OT1 | LR | 77384 | 2457 | 3.175 | 102421 | 679 | 0.663 | 104841 | 2062 |
| OT2 | LL | 82212 | 2615 | 3.181 | 74331 | 2632 | 3.541 | 87613 | 19 |
| OT3 | LL | 43559 | 459 | 1.053 | 51501 | 755 | 1.466 | 52579 | 2 |
| OT4 | LL | 43539 | 356 | 0.817 | 50433 | 597 | 1.184 | 51593 | 3 |
| OT5 | LL | 68461 | 552 | 0.806 | 94024 | 822 | 0.874 | 96681 | 27 |
| OT6 | RR | 43415 | 273 | 0.629 | 59950 | 4 | 0.007 | 64682 | 494 |
| OT7 | RR | 73605 | 340 | 0.462 | 81061 | 36 | 0.044 | 96825 | 572 |
| OT8 | LL | 36976 | 246 | 0.665 | 4645 | 29 | 0.624 | 3178 | 4 |
| OT9 | RR | 6579 | 12 | 0.182 | 19452 | 10 | 0.051 | 21794 | 27 |
| OT10 | RR | 11274 | 18 | 0.160 | 1378 | 0 | 0.000 | 932 | 1 |
| OT11 | LR | 82176 | 67 | 0.082 | 46903 | 2 | 0.004 | 38833 | 22 |
| OT12 | LL | 79431 | 31 | 0.039 | 17985 | 6 | 0.033 | 12656 | 0 |
| OT13 | LR | 71502 | 21 | 0.029 | 7432 | 4 | 0.054 | 4300 | 2 |

| | L*/R | L*/R* | | | GFP | | |
|---|---|---|---|---|---|---|---|
| Locus | % indels | total | indels | % indels | total | indels | % indels |
| CCR5 | 58.66 | 51446 | 33558 | 65.23 | 48994 | 1 | 0.002 |
| OT1 | 1.967 | 114213 | 365 | 0.320 | 93871 | 0 | 0.000 |
| OT2 | 0.022 | 89568 | 15 | 0.017 | 81611 | 0 | 0.000 |
| OT3 | 0.003 | 49629 | 3 | 0.005 | 54822 | 1 | 0.002 |
| OT4 | 0.005 | 48349 | 3 | 0.005 | 53729 | 1 | 0.002 |
| OT5 | 0.028 | 92936 | 10 | 0.011 | 106579 | 1 | 0.001 |
| OT6 | 0.764 | 62674 | 15 | 0.024 | 73619 | 0 | 0.000 |
| OT7 | 0.591 | 89077 | 43 | 0.048 | 91085 | 0 | 0.000 |
| OT8 | 0.126 | 4443 | 2 | 0.045 | 25474 | 2 | 0.008 |
| OT9 | 0.124 | 34 | 0 | 0.000 | 60722 | 6 | 0.010 |
| OT10 | 0.107 | 6423 | 1 | 0.016 | 3617 | 0 | 0.000 |
| OT11 | 0.057 | 94060 | 1 | 0.001 | 61402 | 3 | 0.005 |
| OT12 | 0.000 | 9327 | 0 | 0.000 | 68664 | 2 | 0.003 |
| OT13 | 0.047 | 47052 | 26 | 0.055 | 66027 | 1 | 0.002 |

Example 3

Identification of Nuclease Catalytic Domains with Improved Activity

Truncations of the C-terminus of the TALE DNA binding domain in the context of a TALEN have been shown to increase nuclease activity (see, U.S. Patent Publication No. 201103073; Miller et al, ibid). However, truncations of the catalytic domain of the nuclease, derived from the Fok I protein, may also increase activity of a TALEN. Thus, the original sequence of the FokI protein was examined and two sequence variants were identified (shown below). These sequences are highly similar although have differing N-termini and some divergence in the region near the catalytic domain. In the sequences shown below, the regions corresponding to the catalytic nuclease domains used in the engineered nuclease fusions are underlined. The bold 'D' represents the first active site aspartate in each sequence and is shown in uppercase.

```
Swiss-Prot Accession: P14870.1
                                                          (SEQ ID NO: 23)
  1 mflsmvskir tfgwvqnpgk fenlkrvvqv fdrnskvhne vknikiptlv keskiqkelv 61 aimnqhdliy tykelvgtgt sirseapcda iiqatiadqg nkkgyidnws sdgflrwaha 121 lgfieyinks dsfvitdvgl aysksadgsa iekeilieai ssyppairil tlledgqhlt 181 kfdlgknlgf sgesgftslp egilldtlan ampkdkgeir nnwegssdky armiggwldk 241 lglvkqgkke fiiptlgkpd nkefishafk itgeglkvlr rakgstkftr vpkrvyweml 301 atnltdkeyv rtrralilei likagslkie qiqdnlkklg fdevietien dikglintgi 361 fieikgrfyq lkdhilqfvi pnrgvtkqlv kseleekkse lrhklkyvph eyielieiar 421 nstqdrilem kvmeffmkvy gyrgkhlggs rkpDgaiytv gspidygviv dtkaysggyn 481 lpiggademq ryveenqtrn khinpnewwk vypssvtefk flfvsqhfkg nykaqltrln 541 hitncngavl sveelligqe mikagtltle evrrkfnngeinf
```

-continued

```
PDB Accession: 2FOK_A
                                                                (SEQ ID NO: 24)
  1 mvskirtfgw vqnpgkfenl krvvqvfdrn skvhnevkni kiptlvkesk iqkelvaimn 61 qhdliytyke lvgtgtsirs eapcdaiiqa tiadqgnkkg yidnwssdgf lrwahalgfi 121 eyinksdsfv itdvglaysk sadgsaieke ilieaissyp pairiltlle dgqhltkfdl 181 gknlgfsges gftslpegil ldtlanampk dkgeirnnwe gssdkyarmi ggwldklglv 241 kqgkkefiip tlgkpdnkef ishafkitge glkvlrrakg stkftrvpkr vywemlatnl 301 tdkeyvrtrr alileilika gslkiegiqd nlkklgfdev ietiendikg lintgifiei 361 kgrfyqlkdh ilqfvipnrl gkpdlvksel eekkselrhk lkyvpheyie lieiarnstq 421 drilemkvme ffmkvygyrg khlqgsrkpD qaiytvqspi dyqvivdtka ysqgynlpiq 481 qademqryve enqtrnkhin pnewwkvyps svtefkflfv sqhfkqnyka qltrlnhitn 541 cngavlsvee lliqqemika qtltleevrr kfnnqeinf
```

The region that diverges between the two FokI proteins are located near the start of the catalytic domain and are shown underlined in the comparison below. Since the two proteins have different N-terminal ends, the numbering is slightly different:

```
                            (SEQ ID NO: 25)
    P148701 aa 384    QFVIPNRGVTKQLVKSELEEKK (SEQ ID NO: 26)
    2FOK_A aa 380     QFVIPNRLGKPDLVKSELEEKK
```

Deletions are made in the FokI catalytic domain between the attachment point of the TALE DNA binding domain and the first residue of the active site in the nuclease domain (D454 or D450 in the full length sequences above). Shown below are the deletions made in both partners of the 101041/101047 CCR-5 specific TALEN pair. These partial FokI sequences will replace the FokI cleavage domain in the 101041 and 101047 TALEN pair. Deleted 101041 partners are tested with the standard 101047 partner, and deleted 101047 partners are tested with the standard 101041 partner, and CCR-5 specific pairs where both partners have deletions are tested. The targets for these test are those containing a set of gap spacings to allow determine the effect of different gap spacings and different deletions on TALEN activity. The deletion series is as shown (SEQ IDs NOs 27 through 47).

```
LVKSELEEKKSELRHKLKYVPHEYIELIEIARNSTQDRILEMKVMEFFMKVYGYRGKHLGGSRKPD . . .

VKSELEEKKSELRHKLKYVPHEYIELIEIARNSTQDRILEMKVMEFFMKVYGYRGKHLGGSRKPD . . .

KSELEEKKSELRHKLKYVPHEYIELIEIARNSTQDRILEMKVMEFFMKVYGYRGKHLGGSRKPD . . .

SELEEKKSELRHKLKYVPHEYIELIEIARNSTQDRILEMKVMEFFMKVYGYRGKHLGGSRKPD . . .

ELEEKKSELRHKLKYVPHEYIELIEIARNSTQDRILEMKVMEFFMKVYGYRGKHLGGSRKPD . . .

LEEKKSELRHKLKYVPHEYIELIEIARNSTQDRILEMKVMEFFMKVYGYRGKHLGGSRKPD . . .

EEKKSELRHKLKYVPHEYIELIEIARNSTQDRILEMKVMEFFMKVYGYRGKHLGGSRKPD . . .

EKKSELRHKLKYVPHEYIELIEIARNSTQDRILEMKVMEFFMKVYGYRGKHLGGSRKPD . . .

EKKSELRHKLKYVPHEYIELIEIARNSTQDRILEMKVMEFFMKVYGYRGKHLGGSRKPD . . .

KKSELRHKLKYVPHEYIELIEIARNSTQDRILEMKVMEFFMKVYGYRGKHLGGSRKPD . . .

KSELRHKLKYVPHEYIELIEIARNSTQDRILEMKVMEFFMKVYGYRGKHLGGSRKPD . . .

SELRHKLKYVPHEYIELIEIARNSTQDRILEMKVMEFFMKVYGYRGKHLGGSRKPD . . .

ELRHKLKYVPHEYIELIEIARNSTQDRILEMKVMEFFMKVYGYRGKHLGGSRKPD . . .

LRHKLKYVPHEYIELIEIARNSTQDRILEMKVMEFFMKVYGYRGKHLGGSRKPD . . .

RHKLKYVPHEYIELIEIARNSTQDRILEMKVMEFFMKVYGYRGKHLGGSRKPD . . .

HKLKYVPHEYIELIEIARNSTQDRILEMKVMEFFMKVYGYRGKHLGGSRKPD . . .

KLKYVPHEYIELIEIARNSTQDRILEMKVMEFFMKVYGYRGKHLGGSRKPD . . .

LKYVPHEYIELIEIARNSTQDRILEMKVMEFFMKVYGYRGKHLGGSRKPD . . .

KYVPHEYIELIEIARNSTQDRILEMKVMEFFMKVYGYRGKHLGGSRKPD . . .
```

```
-continued
YVPHEYIELIEIARNSTQDRILEMKVMEFFMKVYGYRGKHLGGSRKPD . . .

VPHEYIELIEIARNSTQDRILEMKVMEFFMKVYGYRGKHLGGSRKPD . . .
```

The deletions are tested by either the DNA cleavage assay described in co-owned US U.S. Patent Publication 20110301073 or the Cel-I assays described above. Deletions that allow better alignment of the DNA binding domain-nuclease fusion protein on one strand of the DNA with the partner DNA binding domain-nuclease fusion protein on the opposite domain are identified.

The region adjacent to the junction region typically chosen for fusion to heterologous DNA binding domain is also investigated to improve activity. This region is numbered 373-379 on the P14870.1 FokI domain or position 377-383 on the 2FOK A Fold domain. The region is interrogated with a number of amino acid substitutions and additions as follows:

```
                                      SEQ ID NO: 48
QFVIPNRGVTKQLVKSELEEKK, P14870.1

SEQ ID NO: 49
QFVIPNRLGKPDLVKSELEEKK, 2FOK_A

SEQ ID NO: 50
GVTKQLVSELEEKK

SEQ ID NO: 51
VTKQLVSELEEKK

SEQ ID NO: 52
TKQLVSELEEKK

SEQ ID NO: 53
KQLVSELEEKK

SEQ ID NO: 54
LGKPDLVSELEEKK

SEQ ID NO: 55
GKPDLVSELEEKK

SEQ ID NO: 56
KPDLVSELEEKK

SEQ ID NO: 57
PDLVSELEEKK

SEQ ID NO: 58
DLVSELEEKK
```

These substitutions and alterations are made one by one in a standard TALEN protein such as the 101041 and the substituted protein is tested for activity against the target with the standard 101047 partner. Activity is measured using the ELISA and Cel-I assays and demonstrates that alterations in this region can improve TALEN activity.

Example 4

Development of a TALEN Nickase

Previously, it was observed that a ZFN pair comprising one partner with an active FokI domain and another partner fused to an enzymatically inactive FokI domain resulted in a pair that nicks DNA rather than creating a DSB (see co-owned U.S. patent publication 20100047805). Thus, a TALEN nickase is developed as follows. The TALENs made using the deletions and substitutions described in Example 2 are used in a 101041/101070 CCR5-specific TALEN pair and tested. The appropriate substrate containing the TALEN target sites are generated by PCR amplification of CCR5 sequences flanking CCR5 TALEN binding region to generate a substrate. The substrates are $^{32}$P end-labeled using T4 polynucleotide kinase and incubated with TALENs where one partner includes the catalytically inactivating point mutation D450N (D450N). The mixture of radio-labeled substrate DNA and TALEN proteins is incubated at 37° C. for 2 hr as described previously (Miller et al (2007) *Nat. Biotech.* 25:778-785) with modifications described below.

Cleaved DNA is extracted by phenol/chloroform and either untreated (double-stranded cleavage products) or treated with a DNA denaturing solution (1.0M glyoxal, 10 mM NaH2PO4/Na2HPO4, pH 7.0, 50% DMSO) to generate single-stranded DNA before separation on a 10% Ready™ gel TBE gel (Invitrogen). In this assay, double-stranded cleavage products are efficiently generated only with TALEN pairs comprising two catalytically active Fok I domains. For all TALEN pair combinations in which one of the TALENs is catalytically inactivated by the indicated point mutation, double-stranded breaks in the CCR5 target DNA are not generated.

However, TALEN pairs with one catalytically inactive TALEN induce single-stranded breaks. In particular, the fragment seen when both FokI cleavage half-domains are catalytically active in double-stranded cleavage products is also seen in single-stranded cleavage products treated with TALEN pairs containing one catalytically inactive cleavage domain. Similarly, the fragment seen when both FokI cleavage half-domains are catalytically active in double-stranded cleavage products is also seen in single-stranded cleavage products treated with TALEN pairs containing a catalytically inactive cleavage half-domain. These results demonstrate that the use of dimers of cleavage half-domains in which one cleavage half-domain is catalytically inactivated generates SSBs/nicks in double-stranded DNA.

Example 5

Identification of Improved RVDs for Repeat Units R-1, R0 and R1

The R-1 repeat unit may serve a stabilizing role for the R0 and R1 repeats, it may influence the DNA binding preference of the N-cap, or it may serve as a stabilizer for the whole TALE DNA binding array. To identify R-1 variants with increased activity or altered binding specificity, substitutions are made in the RVD like positions 12 and 13 (indicated in bold underline) as follows, where some naturally occurring sequences for the R-1 repeat from TALE13, *Xanthomonas* and *Ralstonia* are shown for reference (SEQ ID NOs 59 and 60, respectively):

```
                                                 (SEQ ID NO: 86)
ATHEAIVGVGKQWSGARALEALLTVAGELRGPPLQ R-1 TALE13

ATHEDIVGVGKQLSGARALEALLTKAGELRGPPLQ R-1 Xanthomonas

LTRAHIVDIARQRSGDLALQALLPVATALTAAPLR R-1 Ralstonia
```

```
                                                   (SEQ ID NO: 61)
ATHEAIVGVGKQFSGARALEALLTVAGELRGPPLQ R-1

(SEQ ID NO: 62)
ATHEAIVGVGKQHSGARALEALLTVAGELRGPPLQ R-1

(SEQ ID NO: 63)
ATHEAIVGVGKQISGARALEALLTVAGELRGPPLQ R-1

(SEQ ID NO: 64)
ATHEAIVGVGKQKSGARALEALLTVAGELRGPPLQ R-1

(SEQ ID NO: 65)
ATHEAIVGVGKQLSGARALEALLTVAGELRGPPLQ R-1

(SEQ ID NO: 66)
ATHEAIVGVGKQNSGARALEALLTVAGELRGPPLQ R-1

(SEQ ID NO: 67)
ATHEAIVGVGKQQSGARALEALLTVAGELRGPPLQ R-1

(SEQ ID NO: 68)
ATHEAIVGVGKQRSGARALEALLTVAGELRGPPLQ R-1

(SEQ ID NO: 69)
ATHEAIVGVGKQVSGARALEALLTVAGELRGPPLQ R-1

(SEQ ID NO: 70)
ATHEAIVGVGKQYSGARALEALLTVAGELRGPPLQ R-1
```

These novel R-1 variants are incorporated into either the CCR-5 specific TALEN pair 101041/101047 and tested for activity against the cognate target DNA sequence or are incorporated into some of the constructs shown in Example 1 and tested for binding activity and specificity using either the same ELISA DNA binding assay or the SELEX assay described in co-owned U.S. Patent Publication 20110301073. When incorporated into the CCR5-specific TALEN pair 101041/101047, the novel R-1 variants are first incorporated into one partner of the dimer pair (either 101041 or 101047) individually and evaluated for activity, and then both partners of the pair are substituted with the variants. Activity is measured by the Cel-I assay as described above, and indicates an increase in cleavage activity when the R-1 is varied.

The R0 repeat unit typically binds to a T nucleotide in a TALE protein. This requirement for a T at the 5' end of the target sequence in the DNA limits sequences that may be modified by this technology. Thus, R0 repeat units are varied to identify novel RVDs that specifically increase activity when present in the R0 repeat. The candidate R0 RVD variants tested are shown below (where the RVDs are indicated with bold underline), with the R0 repeats from *Xanthomonas* and *Ralstonia* shown for reference (SEQ ID NOs:71 and 72, respectively). The nucleotide shown in parenthesis indicates the target nucleotide for the novel variants where NS indicates that the R0 is non-specific and will bind to all four nucleotides.

```
LDTGQLLKIARRG*GVTAVEAVHAWRNALTGAPLN R0 Xanthomonas

LSASQIATVAQYG*ERPAIQALYRLRRKLTRAPLH R0 Ralstonia (SEQ ID NO: 73)
LDTGQLLKIAKRIGGVTAVEAVHAWRNALTGAPLN R0 (A)

(SEQ ID NO: 74)
LDTGQLLKIAKRDGGVTAVEAVHAWRNALTGAPLN R0 (C)

(SEQ ID NO: 75)
LDTGQLLKIAKRNGGVTAVEAVHAWRNALTGAPLN R0 (G)

(SEQ ID NO: 100)
LDTGQLLKIAKRHGGVTAVEAVHAWRNALTGAPLN R0 (G)

(SEQ ID NO: 76)
LDTGQLLKIAKRSGGVTAVEAVHAWRNALTGAPLN R0 (NS)
```

In the R0 variants, the RVD regions tested have three amino acids inserted. In the original reports of the R0 sequences, some of the proteins had an "*" at position 13 of the RVD and it was thought that in these repeat units, a single amino acid was responsible for interaction with the nucleotide target. However, the data indicates that the glycine or glutamate on the C-terminal side of the RVD containing the "*" might actually be part of the RVD. Thus, in order to avoid this ambiguity, novel R0 variants are tested with three amino acids inserted at the RVD region. The novel R0 variants are tested for activity in the CCR5-specific TALEN pair as described above, and identify novel R0 specific RVDs that improve TALEN activity.

In addition to the separate R-1 and R0 variants described above, the R-1 and R0 variants are tested in combinations. For example, the following variants are tested together as described above:

```
                                                   (SEQ ID NO: 77)
ATHEAIVGVGKQLSGARALEALLTVAGELRGPPLQ R-1

(SEQ ID NO78)
LDTGQLLKIAKRIGGVTAVEAVHAWRNALTGAPLN R0 (A)

(SEQ ID NO: 77)
ATHEAIVGVGKQLSGARALEALLTVAGELRGPPLQ R-1

(SEQ ID NO: 79)
LDTGQLLKIAKRDGGVTAVEAVHAWRNALTGAPLN R0 (C)

(SEQ ID NO: 77)
ATHEAIVGVGKQLSGARALEALLTVAGELRGPPLQ R-1

(SEQ ID NO: 80)
LDTGQLLKIAKRNGGVTAVEAVHAWRNALTGAPLN R0 (G)

(SEQ ID NO: 77)
ATHEAIVGVGKQLSGARALEALLTVAGELRGPPLQ R-1

(SEQ ID NO: 81)
LDTGQLLKIAKRHGGVTAVEAVHAWRNALTGAPLN R0 (G)

(SEQ ID NO: 77)
ATHEAIVGVGKQLSGARALEALLTVAGELRGPPLQ R-1

(SEQ ID NO: 101)
LDTGQLLKIAKRSGGVTAVEAVHAWRNALTGAPLN R0 (NS)
```

The activity assays identify pairs of variants with enhanced activity.

Figure 10A:
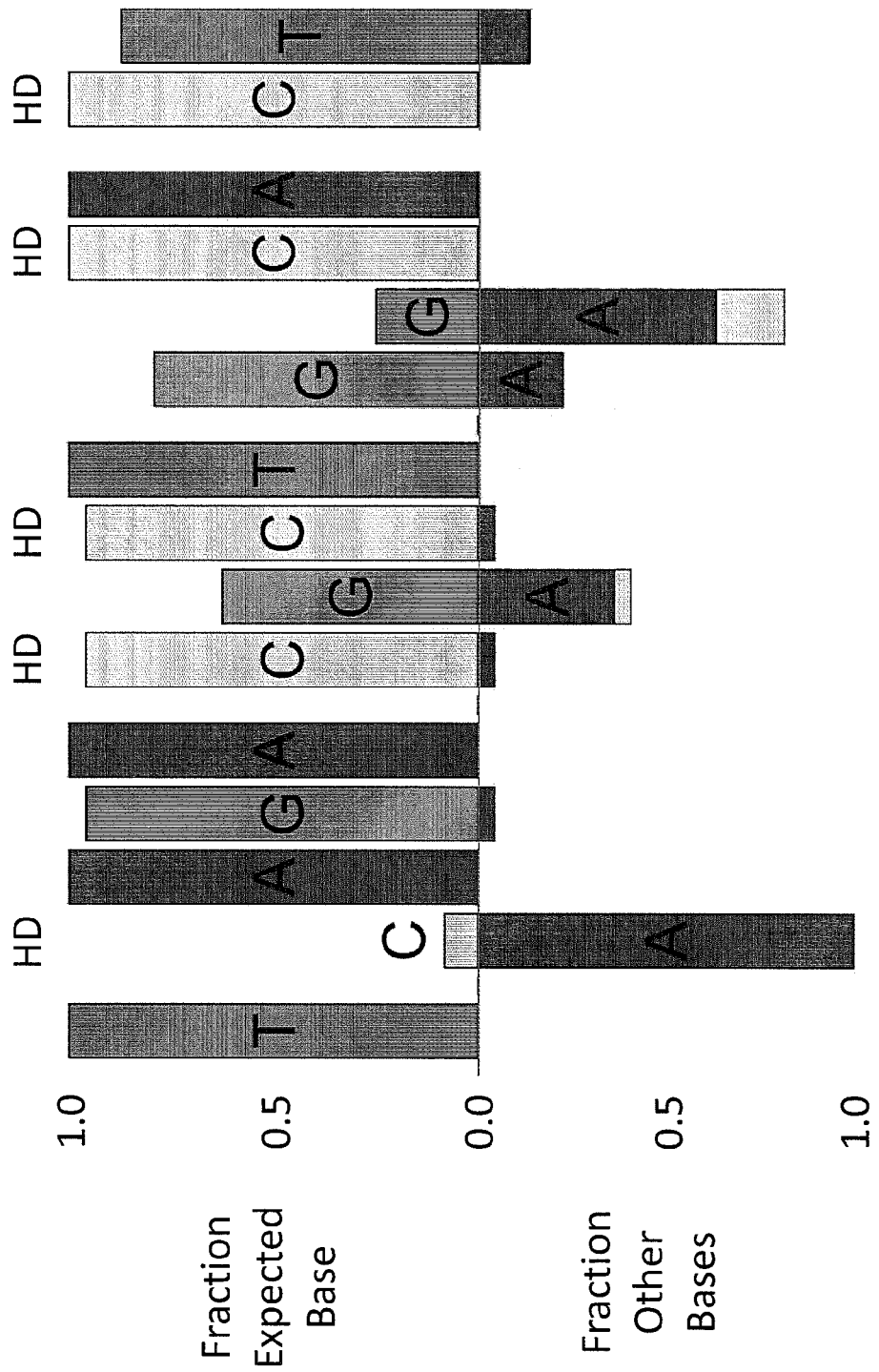
FIG. 10A shows the results for TALEN SBS101146 (target site shown in SEQ ID NO:91)
Figure 10B:
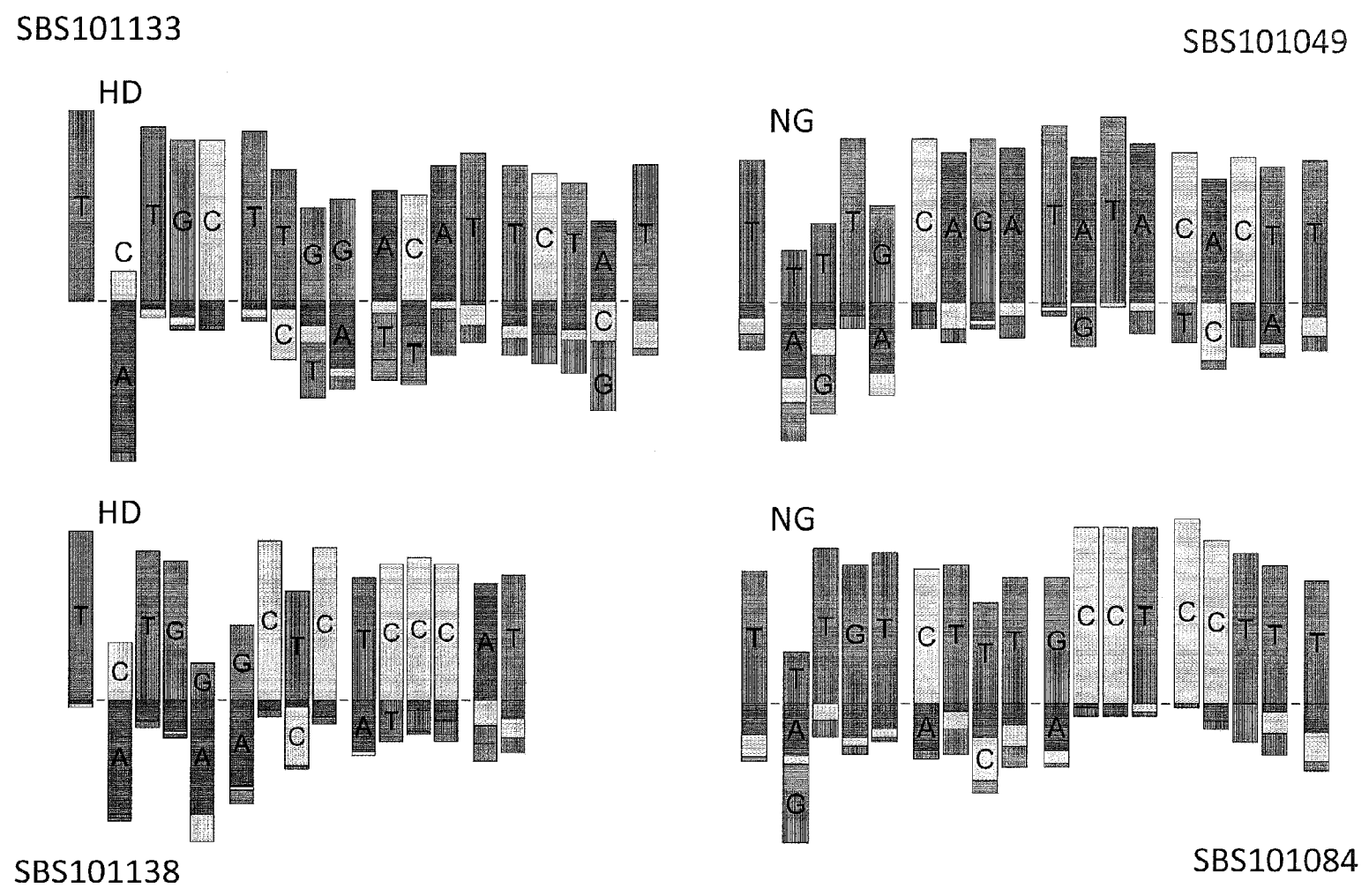
Figure 11:
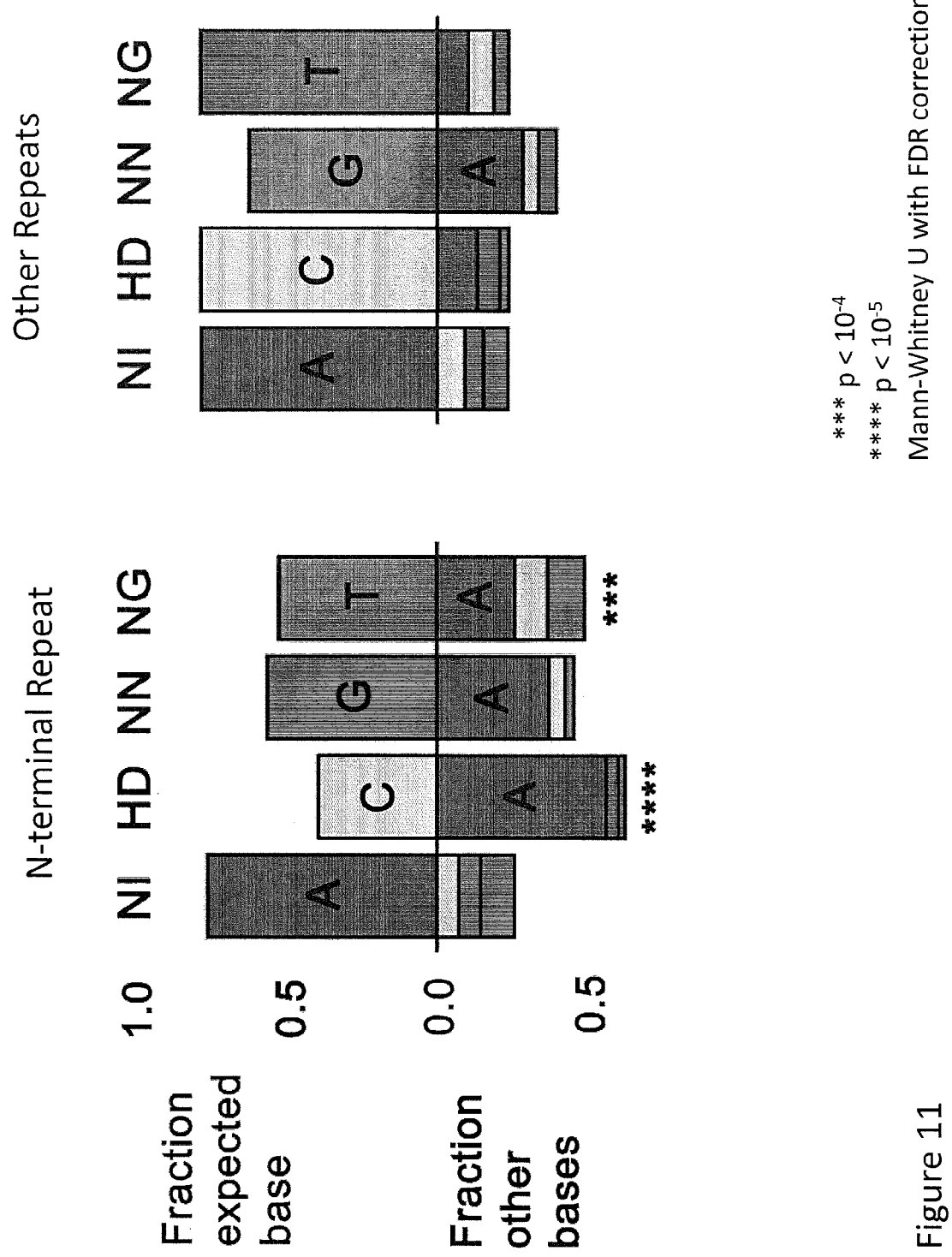
FIG. 11 depicts a mathematical analysis of the variability of the canonical RVDs when located at the R1 position (on left) versus other positions within the TALE DNA binding domain (right).

In some TALENs, the R1 position has unique activity that may be driven by its position and context in the TALE DNA binding domain Several engineered TALENs, made with canonical RVDs, were tested by SELEX which demonstrated that the base preference of NI, HD, NN and NG when the RVD was in the R1 position within a TALE DNA binding domain (FIGS. 10A and 10B) was significantly altered in comparison with when that RVD was in the other repeat domains (e.g. R2-RX) (FIG. 11). The target sequences and the genes are shown below in Table 12a.

TABLE 12a

TALENs engineered with canonical RVDs: Target sequences

| SBS Number | Target gene | Target sequence 5' - 3' | RVD sequences (N->C) |
|---|---|---|---|
| 101146 | hPITX3 | tCAGACGCTGGCACT (SEQ ID NO: 102) | HD-NI-NN-NI-HD-NN-HD-NG-NN-NN-HD-NI-HD-NG |
| 101133 | hOCT4 | tCTGCTTGGACATTCTAT (SEQ ID NO: 103) | HD-NG-NN-HD-NG-NG-NN-NN-NI-HD-NI-NG-NG-HD-NG-NI-NG |
| 101138 | hOCT4 | tCTGGGCTCTCCCAT (SEQ ID NO: 104) | HD-NG-NN-NN-NN-HD-NG-HD-NG-HD-HD-NI-NG |
| 101049 | hCXCR4 | tTTTGCAGATATACACTT (SEQ ID NO: 105) | NG-NG-NG-NN-HD-NI-NN-NI-NG-NI-NG-NI-HD-NI-HD-NG-NG |
| 101084 | cgFUT8 | tTTGTCTTTGCCTCCTTT (SEQ ID NO: 106) | NG-NG-NN-NG-HD-NG-NG-NG-NN-HD-HD-NG-HD-HD-NG-NG-NG |
| 101095 | eGFP | tGCCGTTCTTCTGCTTGT (SEQ ID NO: 107) | NN-RD-HD-NN-NG-NG-HD-NG-HD-NG-NN-HD-NG-NG-NN-NG |
| 101100 | VEGF A | tCGAGCTTCCCCTTCATT (SEQ ID NO: 108) | HD-NN-NI-HD-NG-NG-HD-HD-HD-HD-NG-NG-HD-NI-NG-NG |
| 101115 | GDNF | tTCATTGCCTGCCATGT (SEQ ID NO: 109) | NG-HD-NI-NG-NG-NN-HD-HD-NG-NN-HD-HD-NI-NG-NN-NG |
| 101125 | POU5F1 | ctGACCCTGCCTGCTCCT (SEQ ID NO: 110) | NN-NI-HD-HD-HD-NG-NN-HD-HD-NG-NN-HD-NG-HD-HD-NG |
| 101131 | POU5F1 | tGTCCTCCTCTAACTGCT (SEQ ID NO: 111) | NN-NG-HD-RD-NG-HD-HD-NG-HD-NG-NI-NI-HD-NG-NN-HD-NG |
| 101148 | PITX3 | tGGCCCTTGCAGCCGT (SEQ ID NO: 112) | NN-NN-HD-HD-HD-NG-NG-NN-HD-NI-NN-HD-HD-NN-NG |
| 101187 | RIGM | tTCCTGCCCAGCTCCAT (SEQ ID NO: 113) | NG-HD-HD-NG-NN-HD-HD-HD-NI-NN-HD-NG-HD-HD-NI-NG |
| 101188 | RIGM | tTCAGTGTTGTTCTGGT (SEQ ID NO: 114) | NG-HD-NI-NN-NG-NN-NG-NG-NN-NG-NG-HD-NG-NN-NN-NG (SEQ ID NO: 135) |
| 101242 | LRRK2 | tGCTGTAGTCAGCAATCT (SEQ ID NO: 115) | NN-HD-NG-NN-NG-NI-NN-NG-HD-NI-NN-HD-NI-NI-NG-HD-NG |
| 101245 | LRRK2 | tCCCAATGCTGCCATCAT (SEQ ID NO: 116) | HD-HD-HD-NI-NI-NG-NN-HD-NG-NN-HD-HD-NI-NG-HD-NI-NG |
| 101261 | LRRK2 | tCCCCATTCTACAGCAGT (SEQ ID NO: 117) | HD-HD-HD-HD-NI-NG-NG-HD-NG-NI-HD-NI-NN-HD-NI-NN-NG |
| 101262 | LRRK2 | tTGCAAAGATTGCTGACT (SEQ ID NO: 118) | NG-NN-HD-NI-NI-NI-NN-NI-NG-NG-NN-HD-NG-NN-NI-HD-NG |
| 101027 | CCR5 | tGTGGGCAACATGCT (SEQ ID NO: 119) | NN-NG-NN-NN-NN-HD-NI-NI-HD-NI-NG-NN-HD-NG |
| 101029 | CCR5 | tGGTCATCCTCATCCT (SEQ ID NO: 120) | NN-NN-NG-HD-NI-NG-HD-FID-NG-HD-NI-NG-HD-HD-NG |
| 101045 | CCR5 | tGATACTGACTGTAT (SEQ ID NO: 121) | NN-NI-NG-NI-HD-NG-NN-NI-HD-NG-NN-NG-NI-NG |
| 101053 | CXCR4 | tTCCCTTCTGGGCAGT (SEQ ID NO: 122) | NG-HD-HD-HD-NG-NG-HD-NG-NN-NN-NN-HD-NI-NN-NG |
| 101055 | CXCR4 | tTCATCTTTGCCAACGT (SEQ ID NO: 123) | NG-HD-NI-NG-HD-NG-NG-NG-NN-HD-HD-NI-NI-HD-NN-NG |
| 101056 | CXCR4 | tCACAGATATATCTGT (SEQ ID NO: 124) | HD-NI-HD-NI-NN-NI-NG-NI-NG-NI-NG-HD-NG-NN-NG |
| 101059 | GR | tGTAAGCTCTCCTCCAT (SEQ ID NO: 125) | NN-NG-NI-NI-NN-HD-NG-HD-NG-HD-HD-NG-HD-HD-NI-NG |
| 101061 | GR | tGGGAGGTGGTCCTGTT (SEQ ID NO: 126) | NG-NN-NN-NN-NI-NN-NN-NG-NN-NN-NG-HD-HD-NG-NN-NG-NG |

TABLE 12a-continued

TALENs engineered with canonical RVDs: Target sequences

| SBS Number | Target gene | Target sequence 5' - 3' | RVD sequences (N->C) |
|---|---|---|---|
| 101064 | GR | tAATGACATCCTGAAGCT (SEQ ID NO: 127) | NI-NI-NG-NN-NI-HD-NI-NG-HD-HD-NG-NN-NI-NI-NN-HD-NG |
| 101067 | HBB | tAACGGCAGACTTCT (SEQ ID NO: 128) | NI-NI-HD-NN-NN-HD-NI-NN-NI-HD-NG-NG-HD-NG |
| 101069 | HBB | tGGTGCACCTGACTCCT (SEQ ID NO: 129) | NN-NN-NG-NN-HD-NI-HD-HD-NG-NN-NI-HD-NG-HD-HD-NG |
| 101072 | HBB | tGCCCCACAGGGCAGT (SEQ ID NO: 130) | NN-HD-HD-HD-HD-NI-HD-NI-NN-NN-NN-HD-NI-NN-NG |
| 101073 | HBB | tGCCCCACAGGGCAGT (SEQ ID NO: 131) | NN-HD-HD-HD-NI-HD-NI-NN-NN-NN-HD-NI-NN-NG |
| 101077 | AAVS1 | tCCCCTCCACCCCACAGT (SEQ ID NO: 132) | HD-HD-HD-HD-NG-HD-HD-NI-HD-HD-HD-HD-NI-HD-NI-NN-NG |
| 101079 | AAVS1 | tTTTCTGTCACCAATCCT (SEQ ID NO: 133) | NG-NG-NG-HD-NG-NN-NG-HD-NI-HD-HD-NI-NI-NG-HD-HD-NG |
| 101091 | eGFP | tCCTGGGGCACAAGCT (SEQ ID NO: 134) | PD-HD-NG-NN-NN-NN-NN-HD-NI-HD-NI-NI-NN-HD-NG |
| 101093 | eGFP | tATAGACGTTGTGGCT (SEQ ID NO: 135) | NI-NG-NI-NN-NI-HD-NN-NG-NG-NN-NG-NN-NN-FID-NG |

Thus, to improve activity of the TALENs, the RVDs are substituted in the R1 position with non-canonical candidates to identify RVDs that have superior activity in the R1 context. All 400 possible amino acid combinations may be substituted at any RVD. Preferred RVDs for testing in the R1 position include XI, XD, XN, XK, XH, XG, XA, and XP where X is any residue except proline. Activity and specificity assays, as described above, identify RVDs that enhance the activity of the R1 repeat unit.

This analysis was also used to determine base preferences for the natural canonical RVDs. Shown below in Table 12b are compilations of this data that demonstrate the frequency of RVDs at specific locations within the repeat unit array in the TALE DNA binding domain.

TABLE 12b

Analysis of RVD positional preference

RVD at N-terminus

| RVD | NI | HD | NN | NG |
|---|---|---|---|---|
| N | 3 | 10 | 15 | 11 |
| A | 0.74 | 0.55 | 0.37 | 0.25 |
| C | 0.07 | 0.39 | 0.05 | 0.11 |
| G | 0.11 | 0.02 | 0.55 | 0.12 |
| T | 0.07 | 0.04 | 0.03 | 0.52 |

TABLE 12b-continued

Analysis of RVD positional preference

RVD at other positions

| RVD | NI | HD | NN | NG |
|---|---|---|---|---|
| N | 102 | 183 | 113 | 142 |
| A | 0.78 | 0.11 | 0.26 | 0.09 |
| C | 0.09 | 0.79 | 0.05 | 0.08 |
| G | 0.07 | 0.03 | 0.63 | 0.05 |
| T | 0.06 | 0.07 | 0.06 | 0.79 | all RVDs:

| RVD | NI | HD | NN | NG |
|---|---|---|---|---|
| N | 105 | 193 | 128 | 153 |
| A | 0.78 | 0.13 | 0.28 | 0.10 |
| C | 0.09 | 0.77 | 0.05 | 0.08 |
| G | 0.08 | 0.03 | 0.62 | 0.05 |
| T | 0.06 | 0.07 | 0.06 | 0.77 |

Boxed data indicate the intended bases. Similarly, the analysis revealed that RVD dimers also demonstrated preferences. Shown below in Table 12 c are the results when all 16 canonical dimers are analyzed for preferences. Boxed data again indicates intended DNA bases.

TABLE 12c

Preference for RVD dimers
Average adjacent base preferences for RVD dimers

| RVDs | NI-NI | | NI-HD | | NI-NN | | NI-NG | |
|---|---|---|---|---|---|---|---|---|
| N | 12 | | 30 | | 27 | | 26 | |
| A | 0.74 | 0.76 | 0.79 | 0.07 | 0.81 | 0.25 | 0.78 | 0.05 |
| C | 0.12 | 0.12 | 0.09 | 0.82 | 0.09 | 0.04 | 0.07 | 0.05 |
| G | 0.06 | 0.04 | 0.06 | 0.02 | 0.05 | 0.62 | 0.10 | 0.03 |
| T | 0.08 | 0.08 | 0.05 | 0.10 | 0.05 | 0.09 | 0.05 | 0.87 |

| RVDs | HD-NI | | HD-HD | | HD-NN | | HD-NG | |
|---|---|---|---|---|---|---|---|---|
| N | 51 | | 55 | | 7 | | 54 | |
| A | 0.06 | 0.78 | 0.12 | 0.10 | 0.11 | 0.27 | 0.15 | 0.08 |
| C | 0.82 | 0.11 | 0.80 | 0.80 | 0.85 | 0.02 | 0.75 | 0.08 |
| G | 0.02 | 0.05 | 0.03 | 0.03 | 0.01 | 0.66 | 0.03 | 0.04 |
| T | 0.09 | 0.06 | 0.06 | 0.07 | 0.03 | 0.05 | 0.07 | 0.80 |

| RVDs | NN-NI | | NN-HD | | NN-NN | | NN-NG | |
|---|---|---|---|---|---|---|---|---|
| N | 16 | | 43 | | 25 | | 18 | |
| A | 0.15 | 0.81 | 0.35 | 0.10 | 0.25 | 0.40 | 0.24 | 0.10 |
| C | 0.02 | 0.05 | 0.07 | 0.82 | 0.04 | 0.05 | 0.04 | 0.08 |
| G | 0.78 | 0.09 | 0.51 | 0.02 | 0.65 | 0.52 | 0.67 | 0.04 |
| T | 0.05 | 0.05 | 0.08 | 0.06 | 0.06 | 0.04 | 0.04 | 0.79 |

| RVDs | NG-NI | | NG-HD | | NG-NN | | NG-NG | |
|---|---|---|---|---|---|---|---|---|
| N | 15 | | 42 | | 47 | | 33 | |
| A | 0.05 | 0.75 | 0.09 | 0.16 | 0.07 | 0.20 | 0.13 | 0.12 |
| C | 0.04 | 0.07 | 0.10 | 0.74 | 0.06 | 0.06 | 0.08 | 0.10 |
| G | 0.04 | 0.14 | 0.03 | 0.04 | 0.03 | 0.67 | 0.09 | 0.06 |
| T | 0.87 | 0.04 | 0.78 | 0.06 | 0.84 | 0.07 | 0.71 | 0.72 |

We also found that some RVDs exhibited significantly altered base preference when used with an amino terminal repeat versus other repeat positions (for example, N-terminal vs. non-N-terminal preference for HD, p value is 0.000005; for NG, p value is 0.00006). Some RVDs exhibited base preferences that varied significantly depending on the identity of neighboring RVDs. These are shown below in Table 12d, where all p-values are Mann Whitney U test with FDR correction.

TABLE 12d

Influence of adjacent RVD sequence

| RVD | Adjacent C-terminal RVD | p-value | Adjacent N-terminal RVD | RVD | p-value |
|---|---|---|---|---|---|
| HD | NI vs. NG | 0.0161 | NI vs. NG | HD | 0.0470 |
| NN | HD vs. NI | 0.0003 | NN vs. NG | NN | 0.0137 |
| NN | HD vs. NN | 0.0110 | NI vs. HD | NG | 0.0470 |
| NN | HD vs. NG | 0.0110 | NG vs. NI | NG | 0.0034 |
| NG | NG vs. NI | 0.0043 | | | |

Example 6

Identification of Improved TALE Repeat Units by Varying Position 11

To identify further enhanced TALE repeat units, the amino acids at position 11 of the repeat unit were varied. Position 11 is the position immediately adjacent to the RVD, and thus may have an effect on the binding of the RVD to its target nucleotide. In these experiments, a small subset of RVDs was chosen, and then all possible amino acid substitutions were made at position 11 adjacent to these RVDs were generated. A TALE binding domain was constructed whose binding activity was shown by SELEX and ELISA to be sensitive to a mismatch at the middle position. This protein bound the sequence 5'-TTGACAATCCT-3'(SEQ ID NO:82) and displayed little binding activity against the sequences 5'-TTGACCATCCT-3' (SEQ ID NO:83), 5'-TTGACGATCCT-3' (SEQ ID NO:84), or 5'-TTGACTATCCT-3' (SEQ ID NO:85). These targets are referred to as the CXA targets denoting the middle triplet nucleic acid, where X is either A, C, T or G.

This TALE backbone was then used to characterize the DNA-binding specificity of alternative amino acids in position 11 for the TALE repeat that targets the base at the 6th position. Results from these studies are shown below in Table 13 and demonstrate that this assay identifies several candidate amino acids for position 11 that enhance binding activity as compared to the wild-type position 11.

TABLE 13

Amino acids at position 11 affect binding

| sample | Position | | | Raw Signal | | | | Normalized | | | | Specificity | | | |
|---|---|---|---|---|---|---|---|---|---|---|---|---|---|---|---|
| | 11 | 12 | 13 | A | C | G | T | A | C | G | T | A | C | G | T |
| AKD | A | K | D | 16 | 81 | 5 | 9 | 0.04 | 0.27 | 0.00 | 0.02 | 12 | 83 | 0 | 5 |
| CKD | C | K | D | | | | | | | | | | | | |
| DKD | D | K | D | 7 | 12 | 6 | 8 | 0.01 | 0.03 | 0.00 | 0.01 | | | | |
| EKD | E | K | D | 7 | 9 | 6 | 9 | 0.01 | 0.01 | 0.00 | 0.02 | | | | |
| FKD | F | K | D | 8 | 13 | 6 | 10 | 0.01 | 0.03 | 0.00 | 0.02 | | | | |
| GKD | G | K | D | 13 | 68 | 6 | 13 | 0.03 | 0.22 | 0.00 | 0.03 | 10 | 78 | 1 | 11 |
| HKD | H | K | D | 17 | 101 | 7 | 15 | 0.04 | 0.34 | 0.00 | 0.04 | 10 | 81 | 1 | 9 |
| IKD | I | K | D | 8 | 34 | 8 | 30 | 0.01 | 0.10 | 0.01 | 0.09 | 4 | 49 | 4 | 43 |
| KKD | K | K | D | 78 | 187 | 10 | 52 | 0.25 | 0.64 | 0.02 | 0.17 | 24 | 59 | 2 | 15 |
| LKD | L | K | D | 6 | 19 | 5 | 8 | 0.00 | 0.05 | 0.00 | 0.01 | 6 | 76 | 0 | 19 |
| MKD | M | K | D | 11 | 52 | 5 | 8 | 0.02 | 0.16 | 0.00 | 0.01 | 10 | 83 | 0 | 7 |
| NKD | N | K | D | | | | | | | | | | | | |
| PKD | P | K | D | 8 | 9 | 7 | 9 | 0.01 | 0.01 | 0.01 | 0.01 | | | | |
| QKD | Q | K | D | 78 | 140 | 7 | 30 | 0.26 | 0.48 | 0.01 | 0.09 | 31 | 57 | 1 | 11 |
| RKD | R | K | D | 18 | 46 | 6 | 17 | 0.04 | 0.15 | 0.00 | 0.04 | 19 | 61 | 2 | 19 |
| SKD* | S | K | D | 45 | 147 | 6 | 29 | 0.14 | 0.50 | 0.00 | 0.09 | 19 | 68 | 1 | 12 |
| TKD | T | K | D | 18 | 86 | 6 | 14 | 0.05 | 0.29 | 0.00 | 0.03 | 12 | 78 | 1 | 9 |
| VKD | V | K | D | 11 | 62 | 7 | 12 | 0.02 | 0.20 | 0.01 | 0.03 | 8 | 80 | 2 | 10 |
| WKD | W | K | D | 8 | 20 | 6 | 11 | 0.01 | 0.05 | 0.00 | 0.02 | 11 | 60 | 2 | 27 |
| YKD | Y | K | D | 7 | 20 | 6 | 10 | 0.01 | 0.05 | 0.00 | 0.02 | 8 | 65 | 3 | 23 |
| ARD | A | R | D | 39 | 132 | 9 | 12 | 0.12 | 0.45 | 0.01 | 0.03 | 20 | 74 | 2 | 4 |
| CRD | C | R | D | 41 | 154 | 8 | 17 | 0.12 | 0.52 | 0.01 | 0.04 | 18 | 74 | 2 | 6 |
| DRD | D | R | D | 16 | 28 | 7 | 12 | 0.04 | 0.08 | 0.01 | 0.03 | 26 | 53 | 5 | 17 |
| ERD | E | R | D | | | | | | | | | | | | |
| FRD | F | R | D | | | | | | | | | | | | |
| GRD | G | R | D | 25 | 149 | 5 | 16 | 0.07 | 0.51 | 0.00 | 0.04 | 11 | 82 | 0 | 6 |
| HRD | H | R | D | 45 | 116 | 10 | 18 | 0.14 | 0.39 | 0.02 | 0.05 | 24 | 66 | 3 | 8 |
| IRD | I | R | D | 27 | 104 | 7 | 11 | 0.08 | 0.35 | 0.01 | 0.02 | 17 | 77 | 2 | 5 |
| KRD | K | R | D | 142 | 246 | 16 | 32 | 0.48 | 0.85 | 0.04 | 0.10 | 33 | 58 | 3 | 7 |
| LRD | L | R | D | 14 | 59 | 6 | 10 | 0.03 | 0.19 | 0.00 | 0.02 | 12 | 79 | 1 | 9 |
| MRD | M | R | D | 42 | 142 | 7 | 17 | 0.13 | 0.48 | 0.00 | 0.04 | 20 | 73 | 1 | 7 |
| NRD | N | R | D | 25 | 154 | 6 | 13 | 0.07 | 0.53 | 0.00 | 0.03 | 11 | 84 | 1 | 5 |
| PRD | P | R | D | 17 | 70 | 6 | 10 | 0.04 | 0.23 | 0.00 | 0.02 | 14 | 78 | 1 | 6 |
| QRD | Q | R | D | 49 | 195 | 8 | 15 | 0.16 | 0.67 | 0.01 | 0.04 | 18 | 77 | 1 | 4 |
| RRD | R | R | D | 100 | 163 | 18 | 24 | 0.33 | 0.56 | 0.05 | 0.07 | 33 | 55 | 5 | 7 |
| SRD* | S | R | D | 79 | 264 | 7 | 20 | 0.26 | 0.91 | 0.01 | 0.06 | 21 | 74 | 0 | 5 |
| TRD | T | R | D | 17 | 73 | 7 | 10 | 0.04 | 0.24 | 0.01 | 0.02 | 14 | 78 | 2 | 7 |
| VRD | V | R | D | | | | | | | | | | | | |
| WRD | W | R | D | | | | | | | | | | | | |
| YRD | Y | R | D | 13 | 76 | 5 | 15 | 0.03 | 0.25 | 0.00 | 0.04 | 8 | 80 | 0 | 11 |
| ARI | A | R | I | 121 | 16 | 8 | 9 | 0.41 | 0.04 | 0.01 | 0.02 | 87 | 8 | 2 | 3 |
| CRI | C | R | I | 122 | 19 | 9 | 10 | 0.41 | 0.05 | 0.01 | 0.02 | 84 | 10 | 3 | 4 |
| DRI | D | R | I | | | | | | | | | | | | |
| ERI | E | R | I | 41 | 8 | 6 | 10 | 0.13 | 0.01 | 0.00 | 0.02 | 81 | 5 | 1 | 13 |
| FRI | F | R | I | 60 | 8 | 5 | 8 | 0.19 | 0.01 | 0.00 | 0.01 | 90 | 5 | 0 | 5 |
| GRI | G | R | I | 133 | 12 | 7 | 11 | 0.45 | 0.02 | 0.01 | 0.02 | 89 | 4 | 2 | 5 |
| HRI | H | R | I | 147 | 29 | 11 | 13 | 0.50 | 0.08 | 0.02 | 0.03 | 79 | 13 | 3 | 5 |
| IRI | I | R | I | 66 | 9 | 5 | 8 | 0.22 | 0.01 | 0.00 | 0.01 | 89 | 6 | 0 | 4 |
| KRI | K | R | I | 215 | 86 | 42 | 25 | 0.74 | 0.28 | 0.13 | 0.07 | 60 | 23 | 11 | 6 |
| LRI | L | R | I | 49 | 10 | 6 | 12 | 0.15 | 0.02 | 0.00 | 0.03 | 77 | 8 | 2 | 13 |
| MRI | M | R | I | 163 | 15 | 8 | 15 | 0.56 | 0.03 | 0.01 | 0.04 | 87 | 5 | 2 | 6 |
| NRI | N | R | I | 6 | 7 | 6 | 8 | 0.00 | 0.00 | 0.00 | 0.01 | | | | |
| PRI | P | R | I | 35 | 7 | 6 | 10 | 0.11 | 0.01 | 0.00 | 0.02 | 77 | 5 | 3 | 14 |
| QRI | Q | R | I | 161 | 19 | 8 | 10 | 0.55 | 0.05 | 0.01 | 0.02 | 88 | 8 | 2 | 3 |
| RRI | R | R | I | 155 | 67 | 29 | 22 | 0.53 | 0.22 | 0.08 | 0.06 | 59 | 24 | 9 | 7 |
| SRI* | S | R | I | 151 | 18 | 10 | 11 | 0.51 | 0.04 | 0.02 | 0.02 | 86 | 7 | 3 | 4 |
| TRI | T | R | I | | | | | | | | | | | | |
| VRI | V | R | I | 96 | 14 | 7 | 9 | 0.32 | 0.03 | 0.01 | 0.01 | 86 | 8 | 2 | 4 |
| WRI | W | R | I | 87 | 12 | 7 | 11 | 0.29 | 0.02 | 0.01 | 0.02 | 84 | 7 | 2 | 6 |
| YRI | Y | R | I | 82 | 14 | 8 | 17 | 0.27 | 0.03 | 0.01 | 0.04 | 77 | 9 | 2 | 12 |
| AAK | A | A | K | 12 | 10 | 58 | 19 | 0.02 | 0.02 | 0.19 | 0.05 | 8 | 6 | 67 | 19 |
| CAK | C | A | K | 11 | 7 | 76 | 11 | 0.02 | 0.01 | 0.25 | 0.02 | 7 | 2 | 82 | 8 |
| DAK | D | A | K | | | | | | | | | | | | |
| EAK | E | A | K | 8 | 7 | 11 | 10 | 0.01 | 0.01 | 0.02 | 0.02 | | | | |

TABLE 13-continued

Amino acids at position 11 affect binding

| sample | Position 11 | 12 | 13 | Raw Signal A | C | G | T | Normalized A | C | G | T | Specificity A | C | G | T |
|---|---|---|---|---|---|---|---|---|---|---|---|---|---|---|---|
| FAK | F | A | K | 8 | 6 | 8 | 10 | 0.01 | 0.00 | 0.01 | 0.02 | | | | |
| GAK | G | A | K | 9 | 7 | 31 | 10 | 0.01 | 0.01 | 0.09 | 0.02 | 11 | 4 | 71 | 14 |
| HAK | H | A | K | 11 | 8 | 58 | 24 | 0.02 | 0.01 | 0.19 | 0.07 | 8 | 3 | 65 | 24 |
| IAK | I | A | K | 10 | 7 | 11 | 20 | 0.02 | 0.01 | 0.02 | 0.06 | 17 | 7 | 21 | 55 |
| KAK | K | A | K | 20 | 10 | 84 | 21 | 0.05 | 0.02 | 0.28 | 0.06 | 13 | 4 | 68 | 15 |
| LAK | L | A | K | 7 | 7 | 11 | 13 | 0.01 | 0.01 | 0.02 | 0.03 | | | | |
| MAK | M | A | K | 8 | 8 | 24 | 13 | 0.01 | 0.01 | 0.07 | 0.03 | 8 | 8 | 57 | 27 |
| NAK | N | A | K | 124 | 27 | 12 | 12 | 0.42 | 0.08 | 0.02 | 0.03 | 76 | 14 | 4 | 5 |
| PAK | P | A | K | 12 | 6 | 9 | 10 | 0.02 | 0.00 | 0.01 | 0.02 | | | | |
| QAK | Q | A | K | 21 | 11 | 31 | 10 | 0.05 | 0.02 | 0.09 | 0.02 | 29 | 12 | 49 | 10 |
| RAK | R | A | K | 11 | 6 | 48 | 17 | 0.02 | 0.00 | 0.15 | 0.04 | 9 | 1 | 69 | 20 |
| SAK* | S | A | K | 9 | 6 | 66 | 11 | 0.01 | 0.00 | 0.21 | 0.02 | 5 | 2 | 84 | 10 |
| TAK | T | A | K | 13 | 8 | 29 | 17 | 0.03 | 0.01 | 0.09 | 0.04 | 17 | 6 | 51 | 26 |
| VAK | V | A | K | | | | | | | | | | | | |
| WAK | W | A | K | | | | | | | | | | | | |
| YAK | Y | A | K | 15 | 7 | 20 | 10 | 0.04 | 0.01 | 0.05 | 0.02 | 31 | 5 | 45 | 18 |
| ANN | A | N | N | 182 | 6 | 134 | 12 | 0.62 | 0.00 | 0.45 | 0.03 | 56 | 0 | 41 | 2 |
| CNN | C | N | N | 172 | 6 | 124 | 9 | 0.59 | 0.00 | 0.42 | 0.02 | 57 | 0 | 41 | 2 |
| DNN | D | N | N | 65 | 6 | 74 | 8 | 0.21 | 0.00 | 0.24 | 0.01 | 45 | 1 | 52 | 3 |
| ENN | E | N | N | 63 | 8 | 83 | 23 | 0.20 | 0.01 | 0.27 | 0.07 | 37 | 1 | 50 | 12 |
| FNN | F | N | N | 52 | 6 | 39 | 12 | 0.17 | 0.00 | 0.12 | 0.03 | 53 | 0 | 38 | 8 |
| GNN | G | N | N | 175 | 7 | 125 | 12 | 0.60 | 0.01 | 0.42 | 0.03 | 57 | 1 | 40 | 3 |
| HNN | H | N | N | 236 | 8 | 204 | 11 | 0.81 | 0.01 | 0.70 | 0.02 | 53 | 1 | 45 | 1 |
| INN | I | N | N | 83 | 6 | 94 | 10 | 0.27 | 0.00 | 0.31 | 0.02 | 45 | 1 | 51 | 3 |
| KNN | K | N | N | 209 | 8 | 157 | 13 | 0.72 | 0.01 | 0.54 | 0.03 | 55 | 1 | 41 | 2 |
| LNN | L | N | N | 60 | 6 | 74 | 8 | 0.19 | 0.00 | 0.24 | 0.01 | 43 | 1 | 54 | 3 |
| MNN | M | N | N | 123 | 11 | 126 | 10 | 0.42 | 0.02 | 0.43 | 0.02 | 47 | 2 | 48 | 2 |
| NNN* | N | N | N | 240 | 8 | 207 | 11 | 0.83 | 0.01 | 0.71 | 0.02 | 53 | 1 | 45 | 2 |
| PNN | P | N | N | 36 | 14 | 49 | 11 | 0.11 | 0.03 | 0.15 | 0.02 | 34 | 10 | 49 | 8 |
| QNN | Q | N | N | 178 | 10 | 134 | 14 | 0.61 | 0.02 | 0.46 | 0.03 | 55 | 1 | 41 | 3 |
| RNN | R | N | N | 277 | 7 | 175 | 14 | 0.96 | 0.01 | 0.60 | 0.03 | 60 | 0 | 38 | 2 |
| SNN* | S | N | N | 324 | 7 | 222 | 12 | 1.12 | 0.01 | 0.76 | 0.03 | 58 | 0 | 40 | 1 |
| TNN | T | N | N | 176 | 7 | 126 | 11 | 0.60 | 0.01 | 0.43 | 0.02 | 57 | 1 | 40 | 2 |
| VNN | V | N | N | | | | | | | | | | | | |
| WNN | W | N | N | 51 | 10 | 47 | 12 | 0.16 | 0.02 | 0.15 | 0.03 | 46 | 5 | 42 | 7 |
| YNN | Y | N | N | 34 | 18 | 32 | 8 | 0.10 | 0.05 | 0.10 | 0.01 | 40 | 18 | 38 | 5 |
| SNI | S | N | I | 278 | 22 | 8 | 11 | 0.96 | 0.06 | 0.01 | 0.02 | 91 | 6 | 1 | 2 |
| SHD | S | H | D | 112 | 370 | 8 | 37 | 0.38 | 1.29 | 0.01 | 0.12 | 21 | 72 | 1 | 6 |
| SNN | S | N | N | 324 | 7 | 222 | 12 | 1.12 | 0.01 | 0.76 | 0.03 | 58 | 0 | 40 | 1 |
| SNG | S | N | G | 184 | 47 | 37 | 284 | 0.63 | 0.15 | 0.11 | 0.99 | 34 | 8 | 6 | 53 |
| BLANK | | | | 5 | 5 | 5 | 4 | 0.00 | 0.00 | 0.00 | 0.00 | | | | |
| BLANK | | | | 6 | 6 | 4 | 5 | 0.00 | 0.00 | 0.00 | 0.00 | | | | |

While the behavior of position 11 variants appears to depend on the identity of the residues at positions 12 and 13 (i.e. the behavior is context dependent), general trends in activity can be found in Table 14 which shows the average activity of all constructs in Table 13 that contain the indicated residue at position 11. Note that Serine (S) is typically found in position 11.

TABLE 14

Summary of position 11 variation data

| Amino acid at position 11 | Average Normalized ELISA for all RVDs tested |
|---|---|
| A | 0.35 |
| C | 0.40 |
| D | 0.12 |
| E | 0.11 |
| F | 0.09 |
| G | 0.34 |
| H | 0.42 |
| I | 0.20 |
| K | 0.61 |
| L | 0.13 |
| M | 0.34 |
| N | 0.32 |
| P | 0.10 |
| Q | 0.45 |
| R | 0.40 |
| S | 0.58 |
| T | 0.26 |
| V | 0.26 |
| W | 0.16 |
| Y | 0.14 |

Example 7

Identification of Improved TALEN Activity by Variation of Nuclease Domain

TALEN activity may also be increased by use of an alternate nuclease domain. BfiI is a type IIs restriction enzymes which recognizes and cleaves DNA at fixed positions downstream of its binding site. After digestion, a one base pair 3' nucleotide protruding end is generated (see example below).

```
                              (SEQ ID NO: 87)
5'-ACTGGGNNNNN (SEQ ID NO: 88)
3'-TGACCCNNNN
```

The BfiI protein is 358 amino acids long (NCBI accession number 2C1LA). The DNA fragment encoding the BfiI catalytic domain from amino acids 2 to 196 was synthesized using the mammalian biased codons, and was then cloned in frame with the TALE coding sequence using the BamHI and XhoI sites. An example of TALE-BfiI ORF and its coding sequence is shown below. The TALE region is single underlined while the BfiI catalytic domain is double underlined.

```
TALE101041-BfiI ORF protein sequence
                                                            (SEQ ID NO: 89)
MDYKDHDGDYKDHDIDYKDDDDKMAPKKKRKVGIHRGVPMVDLRTLGYSQQQQEKIKPKVRSTVAQHHEA
LVGHGFTHAHIVALSQHPAALGTVAVKYQDMIAALPEATHEAIVGVGKQWSGARALEALLTVAGELRGPP
LQLDTGQLLKIAKRGGVTAVEAVHAWRNALTGAPLNLTPDQVVAIASNGGGKQALETVQRLLPVLCQDHG
LTPEQVVAIASHDGGKQALETVQRLLPVLCQAHGLTPDQVVAIASNIGGKQALETVQRLLPVLCQAHGLT
PAQVVAIASNGGGKQALETVQRLLPVLCQDHGLTPDQVVAIASNGGGKQALETVQRLLPVLCQDHGLTPE
QVVAIASNIGGKQALETVQRLLPVLCQAHGLTPDQVVAIASHDGGKQALETVQRLLPVLCQAHGLTPAQV
VAIASNIGGKQALETVQRLLPVLCQDHGLTPDQVVAIASHDGGKQALETVQRLLPVLCQDHGLTPEQVVA
IASHDGGKQALETVQRLLPVLCQAHGLTPDQVVAIASNGGGKQALETVQRLLPVLCQAHGLTPAQVVAIA
NNNGGKQALETVQRLLPVLCQDHGLTPDQVVAIASHDGGKQALETVQRLLPVLCQDHGLTPEQVVAIASN
IGGKQALETVQRLLPVLCQAHGLTPDQVVAIANNNGGKQALETVQRLLPVLCQAHGLTPAQVVAIASHDG
GKQALETVQRLLPVLCQDHGLTPEQVVAIASNGGGRPALESIVAQLSRPDPALAALTNDHLVALACLGGR
PALDAVKKGLPHAPALIKRTNRRIPERTSHRVAGSNFFSLHPNVYATGRPKGLIGMLENVWVSNHTPGEG
TLYLISGFSNYNGGVRFYETFTEHINQGGRVIAILGGSTSQRLSSRQVVEELLNRGVEVHIINRKRILHA
KLYGTSNNLGESLVVSSGNFTGPGMSQNIEASLLLDNNTTQSMGFSWNDMISEMLNQNWHIHNMTNATDA
SPGWNLLYDERTTNLTLDETRS TALE101041-BfiI DNA sequence
                                                            (SEQ ID NO: 90)
ATGGACTACAAAGACCATGACGGTGATTATAAAGATCATGACATCGATTACAAGGATGACGATGACAAGA
TGGCCCCCAAGAAGAAGAGGAAGGTGGGCATTCACCGCGGGGTACCTATGGTGGACTTGAGGACACTCGG
TTATTCGCAACAGCAACAGGAGAAAATCAAGCCTAAGGTCAGGAGCACCGTCGCGCAACACCACGAGGCG
CTTGTGGGGCATGGCTTCACTCATGCGCATATTGTCGCGCTTTCACAGCACCCTGCGGCGCTTGGGACGG
TGGCTGTCAAATACCAAGATATGATTGCGGCCCTGCCCGAAGCCACGCACGAGGCAATTGTAGGGGTCGG
TAAACAGTGGTCGGGAGCGCGAGCACTTGAGGCGCTGCTGACTGTGGCGGGTGAGCTTAGGGGGCCTCCG
CTCCAGCTCGACACCGGGCAGCTGCTGAAGATCGCGAAGAGAGGGGGAGTAACAGCGGTAGAGGCAGTGC
ACGCCTGGCGCAATGCGCTCACCGGGGCCCCCTTGAACCTGACCCCAGACCAGGTAGTCGCAATCGCGTC
GAATGGCGGGGAAAGCAAGCCCTGGAAACCGTGCAAAGGTTGTTGCCGGTCCTTTGTCAAGACCACGGC
CTTACACCGGAGCAAGTCGTGGCCATTGCATCACATGACGGTGGCAAACAGGCTCTTGAGACGGTTCAGA
GACTTCTCCCAGTTCTCTGTCAAGCCCACGGGCTGACTCCCGATCAAGTTGTAGCGATTGCGAGCAACAT
CGGAGGGAAACAAGCATTGGAGACTGTCCAACGGCTCCTTCCCGTGTTGTGTCAAGCCCACGGTTTGACG
CCTGCACAAGTGGTCGCCATCGCCTCCAACGGTGGCGGTAAGCAGGCGCTGGAAACAGTACAGCGCCTGC
TGCCTGTACTGTGCCAGGATCATGGACTCACCCCAGACCAGGTAGTCGCAATCGCGTCGAATGGCGGGGG
AAAGCAAGCCCTGGAAACCGTGCAAAGGTTGTTGCCGGTCCTTTGTCAAGACCACGGCCTTACACCGGAG
CAAGTCGTGGCCATTGCATCAAATATCGGTGGCAAACAGGCTCTTGAGACGGTTCAGAGACTTCTCCCAG
TTCTCTGTCAAGCCCACGGGCTGACTCCCGATCAAGTTGTAGCGATTGCGAGCCATGATGGAGGGAAACA
```

-continued

```
AGCATTGGAGACTGTCCAACGGCTCCTTCCCGTGTTGTGTCAAGCCCACGGTTTGACGCCTGCACAAGTG

GTCGCCATCGCCTCCAATATTGGCGGTAAGCAGGCGCTGGAAACAGTACAGCGCCTGCTGCCTGTACTGT

GCCAGGATCATGGGCTGACCCCAGACCAGGTAGTCGCAATCGCGTCGCATGACGGGGGAAAGCAAGCCCT

GGAAACCGTGCAAAGGTTGTTGCCGGTCCTTTGTCAAGACCACGGCCTTACACCGGAGCAAGTCGTGGCC

ATTGCATCACATGACGGTGGCAAACAGGCTCTTGAGACGGTTCAGAGACTTCTCCCAGTTCTCTGTCAAG

CCCACGGGCTGACTCCCGATCAAGTTGTAGCGATTGCGAGCAATGGGGGAGGGAAACAAGCATTGGAGAC

TGTCCAACGGCTCCTTCCCGTGTTGTGTCAAGCCCACGGTTTGACGCCTGCACAAGTGGTCGCCATCGCC

AACAACAACGGCGGTAAGCAGGCGCTGGAAACAGTACAGCGCCTGCTGCCTGTACTGTGCCAGGATCATG

GTTTGACCCCAGACCAGGTAGTCGCAATCGCGTCGCATGACGGGGGAAAGCAAGCCCTGGAAACCGTGCA

AAGGTTGTTGCCGGTCCTTTGTCAAGACCACGGCCTTACACCGGAGCAAGTCGTGGCCATTGCATCAAAT

ATCGGTGGCAAACAGGCTCTTGAGACGGTTCAGAGACTTCTCCCAGTTCTCTGTCAAGCCCACGGGCTGA

CTCCCGATCAAGTTGTAGCGATTGCGAATAACAATGGAGGGAAACAAGCATTGGAGACTGTCCAACGGCT

CCTTCCCGTGTTGTGTCAAGCCCACGGTTTGACGCCTGCACAAGTGGTCGCCATCGCCTCCCACGACGGC

GGTAAGCAGGCGCTGGAAACAGTACAGCGCCTGCTGCCTGTACTGTGCCAGGATCATGGCCTGACACCCG

AACAGGTGGTCGCCATTGCTAGCAACGGGGGAGGACGGCCAGCCTTGGAGTCCATCGTAGCCCAATTGTC

CAGGCCCGATCCCGCGTTGGCTGCGTTAACGAATGACCATCTGGTGGCGTTGGCATGTCTTGGTGGACGA

CCCGCGCTCGATGCAGTCAAAAAGGGTCTGCCTCATGCTCCCGCATTGATCAAAAGAACCAACCGGCGGA

TTCCCGAGAGAACTTCCCATCGAGTCGCGGGATCCCAGCTGGTGAAGAGCGAGCTGGAGGAGAAGAAGTC

CGAGCTGCGGCACAAGCTGAAGTACGTGCCCCACGAGTACATCGAGCTGATCGAGATCGCCAGGAACAGC

ACCCAGGACCGCATCCTGGAGATGAAGGTGATGGAGTTCTTCATGAAGGTGTACGGCTACAGGGGAAAGC

ACCTGGGCGGAAGCAGAAAGCCTGACGGCGCCATCTATACAGTGGGCAGCCCCATCGATTACGGCGTGAT

CGTGGACACAAAGGCCTACAGCGGCGGCTAGAATCTGCCTATCGGCCAGGCCGACGAGATGCAGAGATAC

GTGGAGGAGAACCAGACCCGGAATAAGCACATCAACCCCAACGAGTGGTGGAAGGTGTACCCTAGCAGCG

TGACCGAGTTCAAGTTCCTGTTCGTGAGCGGCCACTTCAAGGGCAACTACAAGGCCCAGCTGACCAGGCT

GAACCACATCACCAACTGCAATGGCGCCGTGCTGAGCGTGGAGGAGCTGCTGATCGGCGGCGAGATGATC

AAAGCCGGCACCCTGACACTGGAGGAGGTGCGGCGCAAGTTCAACAACGGCGAGATCAACTTCAGATCTT

GATAA
```

The BfiI nuclease domain was attached to the CCR5 specific TALE DNA binding domains 101042, 101043, 101047 and 101048 shown below (SEQ ID NOs 136-137 and 139-140, respectively; full-length sequence disclosed as SEQ ID NO: 138):

```
101042              tACACCTGCAGCTCT 101043              tACACCTGCAGCTCTCAT
        AAAAAGAAGGTCTTCATTACACCTGCAGCTCTCATTTTCC

ATACAGTCAGTATCAATTCTGGAAGAATTTCCAGACATTTT

TCTTCCAGAAGTAATGTGGACGTCGAGAGTAAAAGGTATG

TCAGTCATAGTTAAGACCTTCTTAAAGGTCTGT

101047              TCATAGTTAAGACCTTCt

101048              TAGTTAAGACCTTCTt
```

Pairs of BfiI TALENs were transfected into human K562 cells. The target regions in the genome were amplified by PCR and NHEJ events were detected using a standard NextGen sequencing method. The results shown below in Table 15 indicated that, like the FokI nuclease catalytic domain, the BfiI catalytic domain could cleave DNA at specific site when fused with a TALE DNA binding domain. The efficiency of TALE-BfiI nuclease activities can be further improved by optimizing the linker region between TALE and BfiI and by using a shorter or longer BfiI catalytic domain. Alternatively, the BfiI catalytic domain can also be fused to the N-terminal site of a TALE DNA binding domain.

TABLE 15

NHEJ activity determined by deep sequencing

| Left TALEN | Right TALEN | Indel % |
|---|---|---|
| 101042-Bfil | 101047-Bfil | 0.11 |
| 101042-Bfil | 101048-Bfil | 0.17 |
| 101043-Bfil | 101047-Bfil | 0.75 |
| 101043-Bfil | 101048-Bfil | 0.27 |

Examples of the types of Indels generated are shown in the sequence displayed in FIG. 12.

Example 8

Activity of TALEN Activity Using Variant FokI Domains

We compared the nuclease activity of the following TALEN pairs using either the wild-type FokI domain, or the 'eHiFi' FokI domain (ELD FokI variant paired with the KKR FokI variant). The TALENs used were targeted to CCR5, and their binding sites are shown below (SEQ ID NOs: 141-143 and 139, respectively, in order of appearance):

```
101662/101674/            tTCATTACACCTGCAGCT
101202/101041   AAAAAGAAGGTCTTCATTACACCTGCAGCTCTCAT
                TTTCCATACAGTCAGTATCAATTCTGGAAGAATTT
                TTTTCTTCCAGAAGTAATGTGGACGTCGAGAGTAA
                AAGGTATGTCAGTCATAGTTAAGACCTTCTTAA

101664/101676             TGTCAGTCATAGt

101207/101047             TCATAGTTAAGACCTTCt
```

Figures 13A, 13B:
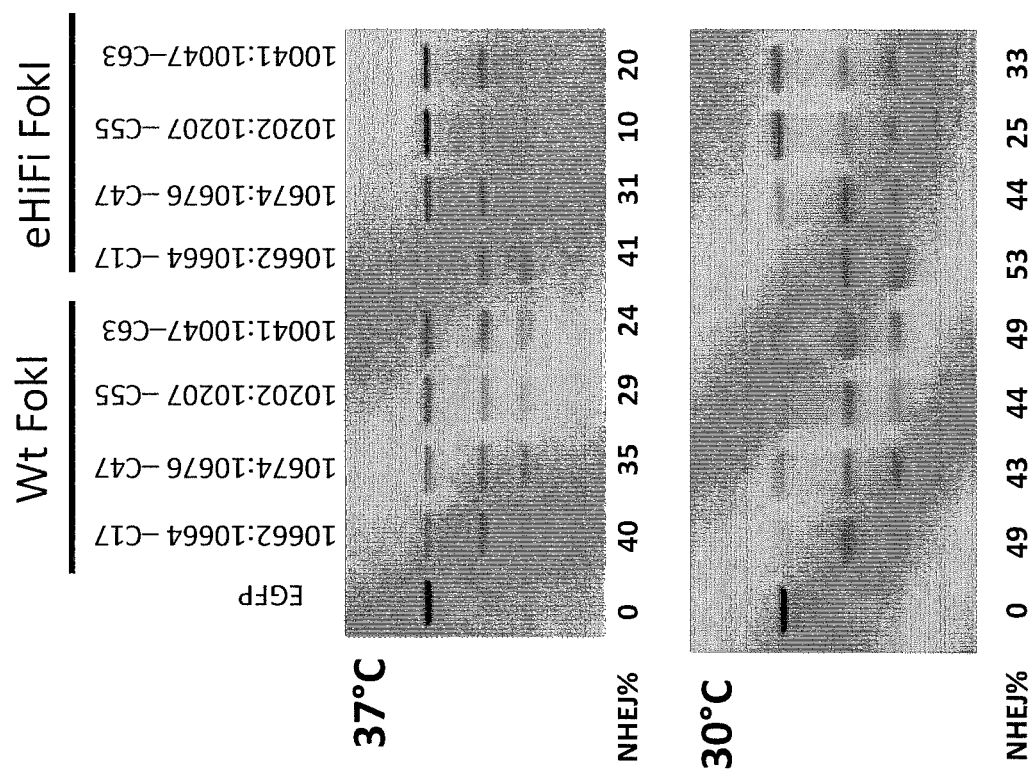
FIG. 13, panels A and B, depict gels obtained from the Cel-I assay. The assay was performed on TALEN samples where the FokI domain was either the wild-type domain or the "eHiFi" variant (see Examples for details). The length of the C-terminal region of the TALE protein is indicated as C17, C47, C55 and C63.

For these pairs, the target sites for 101662, 101674, 101202 and 101041 are all the same, but the C-terminal truncations vary from C+17, C+47, C+55 and C+63 (described above and co-owned US Patent Publication 20110301073). The same pattern is true for 101664 and 101676, and for 101207 and 101047. The TALENs were tested using the Cel-I assay using the standard CCR5 specific target described above. The results are shown in FIGS. 13A and 13B, and demonstrate that at both 30° C. and 37° C., the TALENs made with the eHiFi FokI domains are capable of comparable nuclease activity with the TALENs comprising the wild-type FokI domain. In these experiments, a variety of TALE protein C-terminal truncations were utilized (see co-owned U.S. U.S. Patent Publication 20110301073). The eHiFi FokI nuclease TALENs were active on a variety of TALE DNA binding domains Example 9

Analysis of Base Preference, Comparing RVD Position 12 and Position 13

Figure 14:
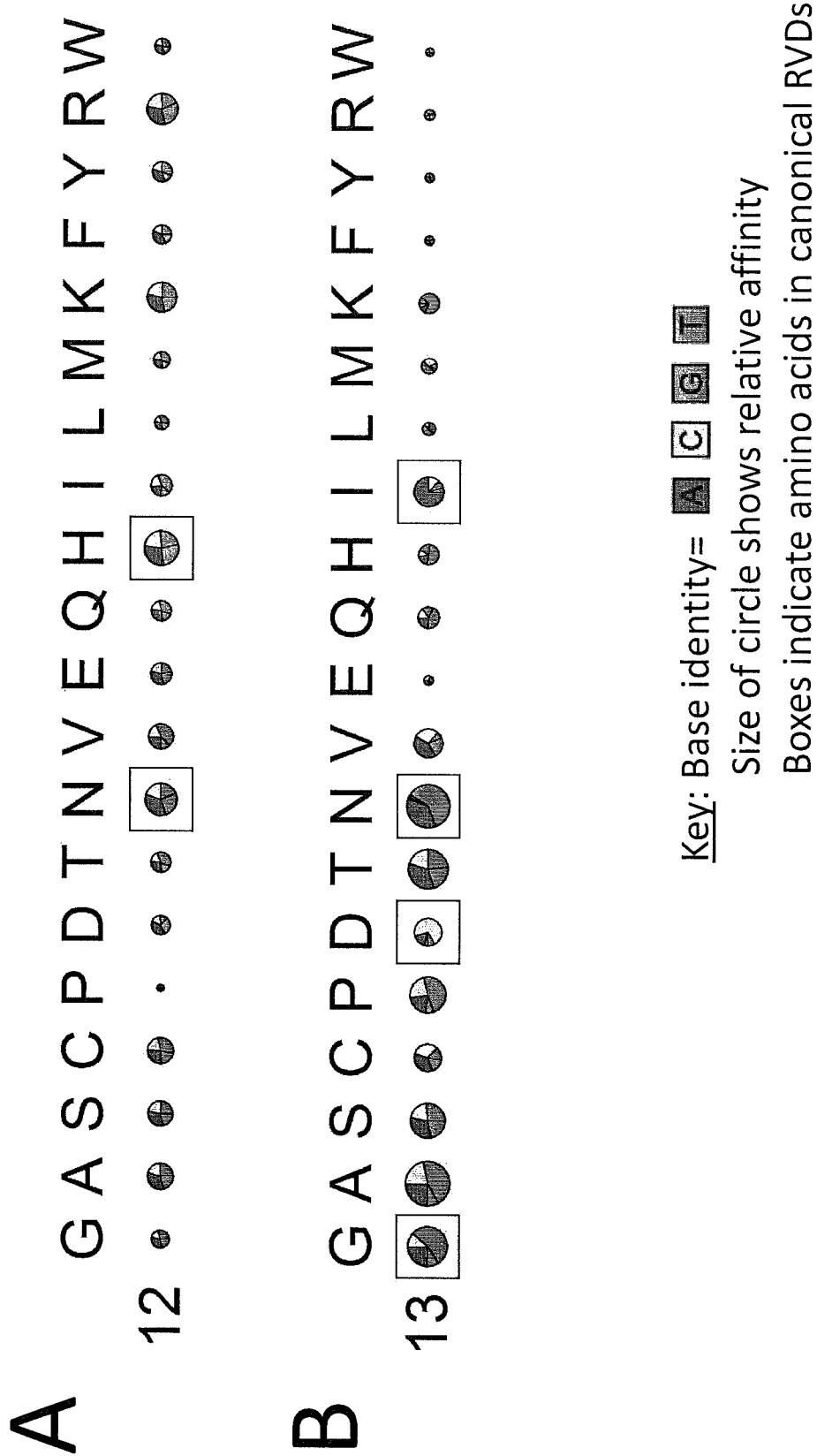
FIG. 14, panels A and B, depicts the base preference and relative affinity for the RVD positions 12 and 13, respectively.

As discussed above, positions 12 and 13 comprise the RVD in a TALE repeat unit, and appear to determine to a large extent what DNA base the repeat unit will interact with. An analysis was carried out (FIG. 14) comparing DNA base preference for each amino acid at position 12 (FIG. 14A) and for each amino acid at position 13 (FIG. 14B). The results demonstrated that position 13 is more selective and has a larger role in affinity and specificity for the binding of the RVD to its cognate DNA base than position 12. Position 13 appears to largely determine base preference. This is most evident for residues G, I, D, and N, which specify T, A, C and G/A, respectively. Residues H and K also tend to specify G albeit with generally weaker affinities and some RVDs containing residues A and P can specify T. Position 12 in contrast, tends to modulate binding strength—in some cases over a more than 50-fold range or relative ELISA signal—with modest or minimal effects on base preference.

Example 10

Activity of CCR5-Specific TALENs in Human CD34+ Cells

TALENs specific for the human CCR5 were designed containing non-canonical RVDs and were tested in human CD34+ cells. The methods used were those described previously (see Holt et al, (2010) *Nat Biotech* 28(8): 839-847). In these experiments, plasmids containing the CCR5-specific TALENs were introduced into K562 cells or fetal liver CD34+ cells using the Amaxa 4D nucleofection protocol according to manufacturer's protocols, where each member of the TALEN pairs was on separate plasmids. 1 μg of each plasmid was used in the nucleofections. The target sites selected in the CCR5 gene are shown below (SEQ ID NOs 141, 138, 143, and 139 from top to bottom), and the TALENs used are shown in Table 16.

Target Sites:

```
L538        tTCATTACACCTGCAGCT
     AAAAAGAAGGTCTTCATTACACCTGCAGCTCTCATTTTCCATACAGTCAGTATCAATTCTGGAAGAATTTCCAGACA

TTTTTCTTCCAGAAGTAATGTGGACGTCGAGAGTAAAAGGTATGTCAGTCATAGTTAAGACCTTCTTAAAGGTCTGT

R551                                  12 bp  TGTCAGTCATAGt

R557                                  18 bp      TCATACTTAAGACCTTCt
```

TABLE 16

CCR5-specific TALEN designs

| Pair | Full Name | Target | RVD | FokI Type | Gap | NHEJ % K562 |
|---|---|---|---|---|---|---|
| 1 | L538-C63-ELD-101041 | tTCATTACACCTGCAGCT (SEQ ID NO: 141) | R0-NG-HD-NI-NG-NG-NI-HD-NI-HD-HD-NG-NN-HD-NI-NN-HD-NG | ELD | 18 bp | 34.4 |
|  | R557-C63-KKR-101047 | tCTTCCAGAATTGATACT (SEQ ID NO: 139) | R0-HD-NG-NG-HD-HD-NI-NN-NI-NI-NG-NG-NN-NI-NG-NI-HD-NG | KKR |  |  |
| 2 | L538NC-C63-ELD-102204 | tTCATTACACCTGCAGCT (SEQ ID NO: 141) | R0-QG-ND-HI-KG-VA-CI-ND-HI-KD-KD-QG-HN-RD-HI-HN-ND-HG | ELD | 18 bp | 40.2 |
|  | R557NC-C63-KKR-102109 | tCTTCCAGAATTGATACT (SEQ ID NO: 139) | R0-RD-AA-QG-AD-KD-HI-AN-KI-KI-RG-RG-FN-CI-KG-HI-AD-KG | KKR |  |  |
| 3 | L538-C17-ELD-101662 | tTCATTACACCTGCAGCT (SEQ ID NO: 141) | R0-NG-HD-NI-NG-NG-NI-HD-NI-HD-HD-NG-NN-HD-NI-NN-HD-NG | ELD | 12 bp | 59.0 |
|  | R551-C17-KKR-101664 | tGATACTGACTGT (SEQ ID NO: 143) | R0-NN-NI-NG-NI-HD-NG-NN-NI-NG-NI-HD-NG | KKR |  |  |
| 4 | L538NC-C17-ELD-102297 | tTCATTACACCTGCAGCT (SEQ ID NO: 141) | R0-QG-ND-HI-KG-VA-CI-ND-HI-KD-KD-QG-HN-RD-HI-HN-ND-HG | ELD | 12 bp | 56.2 |
|  | R551-C17-KKR-101664 | tGATACTGACTGT (SEQ ID NO: 143) | R0-NN-NI-NG-NI-HD-NG-NN-NI-NG-NI-HD-NG | KKR |  |  |

We measured activity using the Cel-I assay as described above and consistently observed significant cleavage (Table 17 below) in both cell types with all TALENs tested.

TABLE 17

Activity of CCR5 specific TALENs in K562 and CD34+ cells

| | | | Exp. 1 | | Exp. 2 | | Exp. 3 | |
|---|---|---|---|---|---|---|---|---|
| Pair # | Full Name | Gap | NHEJ % K562 | NHEJ % CD34 | NHEJ % K562 | NHEJ % CD34 | NHEJ % K562 | NHEJ % CD34 |
| 1 | L538-C63-ELD-101041 R557-C63-KKR-101047 | 18 bp | 31.2 | 22.4 | 49.9 | 45.0 | 51.2 | 18.5 |
| 2 | L538NC-C63-ELD-102204 R557NC-C63-KKR-102109 | 18 bp | 27.8 | 15.8 | 47.1 | 0.0 | 47.7 | 11.4 |
| 3 | L538-C17-ELD-101662 R551-C17-KKR-101664 | 12 bp | 38.0 | 39.7 | 80.5 | 12.4 | 71.9 | 66.9 |
| 4 | L538NC-C17-ELD-102297 R551-C17-KKR-101664 | 12 bp | 41.5 | 46.6 | 76.6 | 22.6 | 71.6 | 56.2 |

The treated CD34+ cells are then tested for engraftment and susceptibility to HIV in vivo using previously described methods (Holt et al (2010) *Nat Biotech* 28(8):893). Briefly, to test if the TALEN-modified cells are capable of multi-lineage engraftment in NSG mice, the TALEN-treated human CD34+ cells are transplanted into 1 day old mice that previously received a low-dose (150 cGy) radiation. Engraftment is successful and results in approximately 40% human CD45+ leukocytes in the peripheral blood at 8 weeks. High levels of human cells are found in the peripheral blood and in the tissues, and CD4+ and CD8+ T cells are present in multiple organs. The bone marrow from the engrafted animals is harvested after 18 weeks and is used to transplant 8-week old recipient mice. Challenge of the transplant recipients 8-12 weeks following transplantation with CCR5-trophic HIV demonstrates protection from HIV infection in the transplanted mice.

Example 11

Using Non-Canonical RVDs to Improve the Activity and Specificity of a Previously Described TALEN Pair that Targets the Human PITX3 Gene Hockemeyer et al. ((2011) *Nat Biotech*, 29:731-734), describe a pair of TALENs, 101236 and 101238, that can introduce indels into the endogenous PITX3 gene in human cells. To exemplify our ability to improve activity and specificity of a TALEN pair, non-canonical and/or atypical RVDs were substituted at a number of positions in the 101238 protein and then the resultant proteins were analyzed. 400 ng of plasmid DNA encoding 101236 was combined with 400 ng of plasmid DNA encoding either 101238, 101238a, 101238b, 101238c, 101238d, or 101238e, and the resulting mixture was transfected into human K562 cells via an Amaxa Shuttle 96-channel electroporator. After transfection, the cells were subjected to the "cold shock" procedure similar to that described in Doyon et al. ((2010) *Nat Meth* (7):459-460), and then the genomic DNA was harvested and the percentage indels in each sample was assayed using the Cel-I assay as described above (Guschin et al., (2010) *Methods Mol Biol.* 649:247-56). The RVDs of 101238, 101238a, 101238b, 101238c, 101238d, and 101238e along with the percentage of indels measured in each sample is given in Table 18. 101238a, 101238b, 101238c, and 101238d have higher activity in combination with 101236 than the original 101238 construct.

constructs were characterized by the SELEX assay using the procedure described above (used to characterize the specificity of TALEN L and TALEN L* in FIG. 7). 101238e did not yield interpretable data with this assay, but the proportion of each base at each position in the SELEX data for the other constructs is shown in Table 19. Large improvements in base preferences at the positions contacted by atypical RVDs RH, NK, and HN were observed for 101238a, 101238b, and 101238c. Positions that showed an increase of at least 0.20 of the portion of the intended base are boxed. Thus, our studies that binding specificity of TALEs can be significantly improved. We estimate that the frequency of repeats with unintended or relaxed base preferences could be reduced by almost half by choosing sites in which the first repeat recognizes "A" and also by preferentially using the NN RVD in its most favorable contexts (see Example 5). Further reductions may be achieved by avoiding targets bearing the "TT" dinucleotide or a small panel of discrete 3-4 base pair sequence motifs.

TABLE 18

Improved TALEN activity

| Construct | RVDs | % Indels |
|---|---|---|
| 101238a | HD-NN-RH-NK-NN-NI-NG-NN-NI-NG-HD-NG-NI-HD | 54 |
| 101238b | HD-NN-RH-HN-NN-NI-NG-NN-NI-NG-HD-NG-NI-HD | 50 |
| 101238c | HD-NN-HN-NK-NN-NI-NG-NN-NI-NG-HD-NG-NI-HD | 44 |
| 101238d | HD-NN-HN-RH-NN-NI-NG-NN-NI-NG-HD-NG-NI-HD | 43 |
| 101238e | HD-NK-NK-NK-NN-NI-NG-NN-NI-NG-HD-NG-NI-HD | 22 |
| 101238 | HD-NN-NN-NN-NN-NI-NG-NN-NI-NG-HD-NG-NI-HD | 34 |

In order to assay the DNA-binding specificity of 101238, 101238a, 101238b, 101238c, 101238d, and 101238e, these

TABLE 19

Increased TALEN specificity

| 101238a | | HD | NN | RH | NK | NN | NI | NG | NN | NI | NG | HD | NG | NI | HD |
|---|---|---|---|---|---|---|---|---|---|---|---|---|---|---|---|
| | A | 0.02 | 0.74 | 0.17 | 0.02 | 0.04 | 0.04 | 1.00 | 0.02 | 0.09 | 0.74 | 0.00 | 0.06 | 0.02 | 0.64 | 0.02 |
| | C | 0.02 | 0.26 | 0.00 | 0.00 | 0.00 | 0.00 | 0.00 | 0.00 | 0.00 | 0.06 | 0.02 | 0.94 | 0.00 | 0.09 | 0.66 |
| | G | 0.00 | 0.00 | 0.83 | 0.98 | 0.96 | 0.96 | 0.00 | 0.00 | 0.91 | 0.19 | 0.00 | 0.00 | 0.02 | 0.28 | 0.00 |
| | T | 0.96 | 0.00 | 0.00 | 0.00 | 0.00 | 0.00 | 0.00 | 0.98 | 0.00 | 0.00 | 0.98 | 0.00 | 0.96 | 0.00 | 0.32 |

| 101238b | | HD | NN | RH | HN | NN | NI | NG | NN | NI | NG | HD | NG | NI | HD |
|---|---|---|---|---|---|---|---|---|---|---|---|---|---|---|---|
| | A | 0.02 | 0.71 | 0.13 | 0.03 | 0.17 | 0.03 | 0.95 | 0.05 | 0.10 | 0.68 | 0.05 | 0.10 | 0.08 | 0.68 | 0.04 |
| | C | 0.04 | 0.29 | 0.02 | 0.02 | 0.00 | 0.00 | 0.00 | 0.02 | 0.00 | 0.13 | 0.02 | 0.90 | 0.02 | 0.14 | 0.48 |
| | G | 0.02 | 0.00 | 0.85 | 0.93 | 0.83 | 0.97 | 0.05 | 0.00 | 0.88 | 0.18 | 0.02 | 0.00 | 0.07 | 0.18 | 0.00 |
| | T | 0.93 | 0.00 | 0.00 | 0.02 | 0.00 | 0.00 | 0.00 | 0.93 | 0.02 | 0.00 | 0.92 | 0.00 | 0.83 | 0.00 | 0.48 |

| 101238c | | HD | NN | HN | NK | NN | NI | NG | NN | NI | NG | HD | NG | NI | HD |
|---|---|---|---|---|---|---|---|---|---|---|---|---|---|---|---|
| | A | 0.02 | 0.75 | 0.20 | 0.10 | 0.03 | 0.12 | 0.83 | 0.05 | 0.08 | 0.60 | 0.02 | 0.13 | 0.15 | 0.64 | 0.04 |
| | C | 0.04 | 0.25 | 0.00 | 0.00 | 0.00 | 0.00 | 0.03 | 0.03 | 0.02 | 0.18 | 0.02 | 0.82 | 0.05 | 0.14 | 0.59 |
| | G | 0.00 | 0.00 | 0.80 | 0.90 | 0.97 | 0.88 | 0.13 | 0.00 | 0.90 | 0.20 | 0.02 | 0.02 | 0.02 | 0.21 | 0.02 |
| | T | 0.95 | 0.00 | 0.00 | 0.00 | 0.00 | 0.00 | 0.00 | 0.92 | 0.00 | 0.02 | 0.95 | 0.03 | 0.78 | 0.02 | 0.36 |

| 101238d | | HD | NN | HN | RH | NN | NI | NG | NN | NI | NG | HD | NG | NI | HD |
|---|---|---|---|---|---|---|---|---|---|---|---|---|---|---|---|
| | A | 0.00 | 0.84 | 0.07 | 0.37 | 0.49 | 0.05 | 0.81 | 0.02 | 0.12 | 0.65 | 0.00 | 0.21 | 0.02 | 0.77 | 0.02 |
| | C | 0.07 | 0.16 | 0.00 | 0.00 | 0.14 | 0.02 | 0.09 | 0.00 | 0.00 | 0.07 | 0.02 | 0.77 | 0.00 | 0.02 | 0.67 |
| | G | 0.02 | 0.00 | 0.91 | 0.60 | 0.35 | 0.93 | 0.09 | 0.05 | 0.86 | 0.28 | 0.00 | 0.00 | 0.02 | 0.21 | 0.00 |
| | T | 0.90 | 0.00 | 0.02 | 0.02 | 0.02 | 0.00 | 0.00 | 0.93 | 0.02 | 0.00 | 0.98 | 0.02 | 0.95 | 0.00 | 0.30 |

| 101238 | | HD | NN | NN | NN | NN | NI | NG | NN | NI | NG | HD | NG | NI | HD |
|---|---|---|---|---|---|---|---|---|---|---|---|---|---|---|---|
| | A | 0.00 | 0.79 | 0.27 | 0.27 | 0.57 | 0.16 | 0.80 | 0.04 | 0.10 | 0.65 | 0.02 | 0.12 | 0.06 | 0.64 | 0.02 |
| | C | 0.11 | 0.19 | 0.02 | 0.04 | 0.00 | 0.00 | 0.02 | 0.02 | 0.04 | 0.06 | 0.02 | 0.86 | 0.00 | 0.13 | 0.45 |
| | G | 0.02 | 0.02 | 0.71 | 0.69 | 0.43 | 0.84 | 0.18 | 0.02 | 0.84 | 0.27 | 0.02 | 0.00 | 0.04 | 0.21 | 0.06 |
| | T | 0.87 | 0.00 | 0.00 | 0.00 | 0.00 | 0.00 | 0.00 | 0.92 | 0.02 | 0.02 | 0.94 | 0.02 | 0.90 | 0.02 | 0.47 |

The complete amino acid sequence of the TALEN pair 101236/101238 is shown below.

```
Complete amino acid sequences of TALENs 101236 and 101238
>101236
                                                          SEQ ID NO: 144
MDYKDHDGDYKDHDIDYKDEDDKMAPKKKRKVGIHRGVPMVDLRTLGYSQQQQEKIKPKVRSTVAQHHEALVGHGFTHAHIVALSQHPA ALGTVAVKYQDMIAALPEATHEAIVGVGKQWSGARALEALLTVAGELRGPPLQLDTGQLLKIAKRGGVTAVEAVHAWRNALTGAPLNLT PDQVVAIASNIGGKQALETVQRLLPVLCQDHGLTPEQVVAIASHDGGKQALETVQRLLPVLCQAHGLTPDQVVAIANNNGGKQALETVQ RLLPVLCQAHGLTPAQVVAIASHDGGKQALETVQRLLPVLCQDHGLTPDQVVAIASHDGGKQALETVQRLLPVLCQDHGLTPDQVVAIA NNNGGKQALETVQRLLPVLCQAHGLTPDQVVAIASNGGGKQALETVQRLLPVLCQAHGLTPAQVVAIANNNGGKQALETVQRLLPVLCQ DHGLTPDQVVAIANNNGGKQALETVQRLLPVLCQDHGLTPEQVVAIASNIGGKQALETVQRLLPVLCQAHGLTPAQVVAIASNIGGKQA LETVQRLLPVLCQDHGLTPDQVVAIASNIGGKQALETVQRLLPVLCQDHGLTPDQVVAIANNNGGKQALETVQRLLPVFCQAHGLTPDQ VVAIANNNGGKQALETVQRLLPVLCQAHGLTPAQVVAIASHDGGKQALETVQRLLPVLCQDHGLTPEQVVAIASHDGGRPALESIVAQL SRPDPALAALTNDHLVALACLGGRPALDAVKKGLPHAPALIKRTNRRIPERTSHRVAGSQLVKSELEEKKSELRHKLKYVPHEYIELIE IARNSTQDRILEMKVMEFFMKVYGYRGKHLGGSRKPDGAIYTVGSPIDYGVIVDTKAYSGGYNLPIGQADEMQRYVEENQTRNKHINPN

EWWKVYPSSVTEFKFLFVSGHFKGNYKAQLTRLNHITNCNGAVLSVEELLIGGEMIKAGTLTLEEVRRKFNNGEINFRS.

>101238
                                                          SEQ ID NO: 145
MDYKDHDGDYKDHDIDYKDDDDKMAPKKKRKVGIHRGVPMVDLRTLGYSQQQQEKIKPKVRSTVAQHHEALVGHGFTHAHIVALSQHPA

ALGTVAVKYQDMIAALPEATHEAIVGVGKQWSGARALEALLTVAGELRGPPLQLDTGQLLKIAKRGGVTAVEAVHAWRNALTGAPLNLT

PDQVVAIASHDGGKQALETVQRLLPVLCQDHGLTPDQVVAIANNNGGKQALETVQRLLPVLCQAHGLTPDQVVAIANNNGGKQALETVQ

RLLPVLCQAHGLTPAQVVAIANNNGGKQALETVQRLLPVLCQDHGLTPDQVVAIANNNGGKQALETVQRLLPVLCQDHGLTPEQVVAIA

SNIGGKQALETVQRLLPVLCQAHGLTPDQVVAIASNGGGKQALETVQRLLPVLCQAHGLTPAQVVAIANNNGGKQALETVQRLLPVLCQ

DHGLTPDQVVAIASNIGGKQALETVQRLLPVLCQDHGLTPEQVVAIASNGGGKQALETVQRLLPVLCQAHGLTPDQVVAIASHDGGKQA

LETVQRLLPVLCQAHGLTPAQVVAIASNGGGKQALETVQRLLPVLCQDHGLTPDQVVAIASNIGGKQALETVQRLLPVLCQDHGLTPEQ

VVAIASHDGGRPALESIVAQLSRPDPALAALTNDHLVALACLGGRPALDAVKKGLPHAPALIKRTNRRIPERTSHRVAGSQLVKSELEE

KKSELRHKLKYVPHEYIELIEIARNSTQDRILEMKVMEFFMKVYGYRGKHLGGSRKPDGAIYTVGSPIDYGVIVDTKAYSGGYNLPIGQ

ADEMQRYVEENQTRNKHINPNEWWKVYPSSVTEFKFLFVSGHFKGNYKAQLTRLNHITNCNGAVLSVEELLIGGEMIKAGTLTLEEVAR

KFNNGEINFRS.
```

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An isolated, non-naturally occurring transcription activator-like effector (TALE) DNA-binding polypeptide comprising a plurality of TALE-repeat units, each TALE-repeat unit comprising a repeat variable di-residue (RVD) region, wherein the TALE DNA-binding polypeptide comprises at least 3 non-canonical RVDs, and wherein the non-canonical RVDs are CI or KI for recognition of an adenine; AD, KD, or RD for recognition of a cytosine; AN, CN, GN, FN, AK or CK for recognition of guanine; and KG, MG, QG, RG, AA, QA or VA for recognition of thymine.

2. The TALE DNA-binding polypeptide of claim 1, wherein the amino acid at position 11 in at least one of the repeat units has been altered as compared to a naturally occurring TALE repeat unit.

3. The TALE DNA-binding polypeptide of claim 2, wherein the amino acid at position 11 is altered to an amino acid selected from the group consisting of an Alanine, Cysteine, Glycine, Histidine, Lysine, Methionine, Asparagine, Glutamine and Arginine.

4. A kit comprising a TALE DNA-binding polypeptide according to claim 1.

5. A fusion protein comprising the TALE DNA-binding polypeptide of claim 1 and a functional domain.

6. The fusion protein of claim 5, wherein the functional domain is selected from the group consisting of a transcriptional activator, a transcriptional repressor, a methyltransferase and a nuclease cleavage domain.

7. The fusion protein according to claim 5, wherein the nuclease cleavage domain comprises a FokI cleavage domain.

8. A dimer comprising the fusion protein of claim 7 and a protein comprising a TALE DNA binding domain polypeptide linked to an inactive FokI catalytic domain.

9. A polynucleotide encoding the TALE DNA-binding polypeptide of claim 1.

10. A polynucleotide encoding the fusion protein of claim 6.

11. An isolated host cell comprising the TALE DNA-binding polypeptide of claim 1.

12. The isolated host cell of claim 11, wherein the cell is a eukaryotic cell.

13. The isolated host cell of claim 12, wherein the cell is a mammalian or plant cell.

14. The isolated host cell of claim 13, wherein the mammalian cell is a stein cell.

15. A method of modulating expression of an endogenous gene in a cell, the method comprising:
    introducing into the cell a fusion protein according to claim 6, wherein the fusion protein binds to a target site in the endogenous gene, and wherein expression of the endogenous gene is modulated by the fusion protein.

16. The method of claim 15, wherein the modulation is selected from the group consisting of gene activation, gene repression and gene inactivation.

17. The method of claim 16, wherein the fusion protein comprises a cleavage domain or cleavage half-domain and the endogenous gene is inactivated by cleavage.

18. The method of claim 15, wherein the fusion protein is introduced as a polynucleotide encoding the fusion protein.

19. A method of modifying a region of interest in a genome of a cell, the method comprising:

introducing into the cell at least one fusion protein according to claim 7, wherein the fusion protein binds to a target site in the genome of the cell and cleaves the genome in the region of interest.

20. The method of claim 19, wherein the modifying comprises introducing a deletion in the region of interest.

21. The method of claim 19, wherein the modifying comprises introducing an exogenous nucleic acid into the region of interest, the method further comprising introducing the exogenous nucleic acid into the cell, wherein the exogenous nucleic acid is integrated into the region of interest by homologous recombination.

22. The method of claim 19, wherein the cell is a eukaryotic cell selected from the group consisting of a plant cell, an animal cell, a fish cell and a yeast cell.

23. The method of claim 19, wherein the fusion protein is introduced as a polynucleotide encoding the fusion protein.

24. A method of making a single-stranded break in a double-stranded DNA target sequence, the method comprising:

binding the dimer according to claim 8 with the double-stranded DNA target sequence.

25. A method of cleaving a double-stranded DNA target, the method comprising:

binding first and second dimers according to claim 8 with the double-stranded DNA target, such that the first and second dimers make first and second single-stranded breaks on complementary strands of the double-stranded DNA target, wherein the first and second single-stranded breaks result in separation of the double-stranded DNA into two fragments, thereby cleaving the double-stranded DNA target.

* * * * *